US012643938B2

(12) United States Patent
Du et al.

(10) Patent No.: US 12,643,938 B2
(45) Date of Patent: Jun. 2, 2026

(54) Fc-CONTAINING MOLECULES EXHIBITING PREDICTABLE, CONSISTENT, AND REPRODUCIBLE GLYCOFORM PROFILES

(71) Applicant: Amgen Inc., Thousand Oaks, CA (US)

(72) Inventors: Zhimei Du, Bellevue, WA (US); Pranhitha Reddy, Seattle, WA (US); Randal B. Bass, Seattle, WA (US); Feng He, Lynnwood, WA (US); William C. Fanslow, III, Normandy Park, WA (US); Yuling Zhang, Bellevue, WA (US); Da Ren, Thousand Oaks, CA (US); Randall R. Ketchem, Snohomish, WA (US)

(73) Assignee: Amgen Inc., Thousand Oaks, CA (US)

( * ) Notice: Subject to any disclaimer, the term of this patent is extended or adjusted under 35 U.S.C. 154(b) by 936 days.

(21) Appl. No.: 17/865,364

(22) Filed: Jul. 14, 2022

(65) Prior Publication Data

US 2023/0235024 A1 Jul. 27, 2023

Related U.S. Application Data

(63) Continuation of application No. 14/916,993, filed as application No. PCT/US2014/054359 on Sep. 5, 2014, now Pat. No. 11,427,627.

(60) Provisional application No. 61/874,222, filed on Sep. 5, 2013.

(51) Int. Cl.
*C07K 16/00* (2006.01)

(52) U.S. Cl.
CPC .......... *C07K 16/00* (2013.01); *C07K 2317/14* (2013.01); *C07K 2317/41* (2013.01); *C07K 2317/52* (2013.01); *C07K 2317/524* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 6,737,056 B1 | 5/2004 | Presta | |
| 8,188,231 B2 | 5/2012 | Lazar et al. | |
| 8,937,158 B2 | 1/2015 | Lazar et al. | |
| 11,427,627 B2 | 8/2022 | Du et al. | |
| 2007/0111281 A1 | 5/2007 | Sondermann et al. | |

FOREIGN PATENT DOCUMENTS

| | | | |
|---|---|---|---|
| EP | 2233500 A1 | 9/2010 | |
| WO | 2004/029207 A2 | 4/2004 | |
| WO | 2006/019447 A1 | 2/2006 | |
| WO | 2008/137382 A1 | 11/2008 | |
| WO | 2011/120134 A1 | 10/2011 | |
| WO | 2012/125559 A1 | 9/2012 | |
| WO | 2013/046704 A2 | 4/2013 | |

OTHER PUBLICATIONS

Li et al., "Crystallizable Fragment Glycoengineering for Therapeutic Antibodies Development", Frontiers in Immunology, (2017), 8:1554, 1-15.
Package Insert Campath® (Alemtuzumab) (pp. 1-11, created Sep. 26, 2003 as indicated in p. 11) (2003).
Iida et al., Two Mechanisms of the Enhanced Antibody-Dependent Cellular Cytotoxicity (ADCC) Efficacy of Non-Fucosylated Therapeutic Antibodies in Human Blood, BMC Cancer (2009), 9:58:1-12.
Lazar et al., Engineered Antibody Fc Variants with Enhanced Effector Function, PNAS (2006), 103:11:4005-4010.
Mizushima et al., Structural Basis for Improved Efficacy of Therapeutic Antibodies on Defucosylation of Their Fc Glycans, Genes to Cells (2011), 16:1071-1080.
Shigeru et al., Two Mechanisms of the Enhanced Antibody-Dependent Cellular Cytotoxicity (ADCC) Efficacy of Non-Fucosylated Therapeutic Antibodies in Human Blood, BMC Cancer (2009), 9:58:1-12.

*Primary Examiner* — Chun W Dahle
(74) *Attorney, Agent, or Firm* — Alla Brukman

(57) ABSTRACT

The present invention relates to variant Fc-containing molecules, such as antibodies and Fc-fusion molecules, having glycosylation characteristics favorable to large-scale production of therapeutic molecules containing such variant Fc.

16 Claims, 16 Drawing Sheets

Specification includes a Sequence Listing.

| Variants | $k_a$ (1/Ms) | $k_d$ (1/s) | $K_d$ (pM) |
|---|---|---|---|
| wt | $1.22 \times 10^5$ | $7.12 \times 10^{-6}$ * | 58.7 |
| S239D | $1.64 \times 10^5$ | $7.12 \times 10^{-6}$ * | 43.7 |
| S239E | $1.23 \times 10^5$ | $7.12 \times 10^{-6}$ * | 58.2 |
| V264D | $1.29 \times 10^5$ | $7.12 \times 10^{-6}$ * | 55.5 |
| D265A | $1.25 \times 10^5$ | $7.12 \times 10^{-6}$ * | 57.3 |
| S239D-V264D | $1.25 \times 10^5$ | $7.12 \times 10^{-6}$ * | 57.3 |
| S239D-D265A | $1.28 \times 10^5$ | $7.12 \times 10^{-6}$ * | 55.9 |

Fc-CONTAINING MOLECULES EXHIBITING PREDICTABLE, CONSISTENT, AND REPRODUCIBLE GLYCOFORM PROFILES

CROSS-REFERENCE TO RELATED APPLICATIONS

This application is a continuation of U.S. patent application Ser. No. 14/916,993, filed Mar. 4, 2016 and issued as U.S. Pat. No. 11,427,627, which is a National Stage application under 35 U.S.C. § 371 of International Patent Application No. PCT/US2014/054359, having an international filing date of Sep. 5, 2014, which claims the benefit of U.S. Provisional Patent Application No. 61/874,222, filed Sep. 5, 2013, each of which is hereby incorporated by reference in its entirety.

SEQUENCE LISTING

The present application contains a Sequence Listing, which has been submitted electronically in ASCII format and is hereby incorporated by reference in its entirety. The ASCII copy of the Sequence Listing, which was created on Mar. 14, 2023, is named 17865364_2_1.xml and is 81,808 bytes in size.

BACKGROUND OF THE INVENTION

In the biopharmaceutical industry, therapeutic glycoproteins, such as recombinant monoclonal antibodies (mAb), are predominantly produced in mammalian cell culture systems. Antibodies including human and recombinant mAb are N-linked glycosylated at a highly conserved residue, Asn297, in the Fc CH2 domain. N-linked glycosylation structure impacts the tertiary structure of the antibody, product stability and in vivo clearance of IgG1 and IgG2. In addition, glycan structure impacts the Fc-mediated antibody effector functions, including antibody-dependent cell-mediated cytotoxicity (ADCC) and complement-dependent cytotoxicity (CDC) activity of IgG1 class.

One key feature of glycosylation is its heterogeneity due to the incomplete processing of the N-linked Fc glycans, reflected by the presence or absence of different terminal sugar residues, including various high mannose forms (Man5-9), sialic acid, galactose and N-acetylglucosamine, and core fucose (FIG. 1). The primary species for mAb are IgG-G0 (no galactose), IgG-G1 (galactose on one arm), and IgG-G2 (galactose on both arms). G1 and G2 are the mature glyco-forms which can be further sialylated (G2FSA1 and G2FSA2) (FIG. 1). Immature glyco-forms of CHO-derived IgG, such as the high-mannose (HM) glycol-forms (Man5-9, as variable as 2-35%), are major concerns due to the higher plasma clearance rate of mAbs containing HM compared to the complex glycan linked mAbs molecules, which may lead to a potential impact on efficacy (Jones et al., (2007) *Glycobiology* 17, 529-540; Goetze et al., (2011) *Glycobiology* 21, 949-959). Another immature glyco-form is the G0 glyco-form without terminal galactose (G0 and G0F), which is the majority of CHO-derived IgG (as variable as 30-60%). IgGs without terminal galactose have been found to be linked with disease activity, and serum transfer studies showed that it can induce diseases (Arnold et al., (2007) *Annu Rev Immunol* 25, 21-50). Also, these glyco-forms lack certain important features of IgGs, such as complement-dependent cytotoxicity (CDC).

Because glycosylation variations can affect product potency, it is a critical product quality attribute that regulatory agencies emphasize. Therefore obtaining a consistent glycoform profile on the therapeutic antibody product is highly desired. However, the cell culture and expression system, such as cell host, media components and process conditions (pH, osmolarity, temperature), significantly impacts the glycan processing. Thus, besides the intrinsic glycan heterogeneity issues, considerable lot-to-lot variability of mAb glycan profile between different production processes of the same molecule has also been a common scenario. Significant amount of resources are spent in optimizing manufacturing processes and comparability exercises in order to control mAb glycosylation. Due to the complexity of CHO cell production system, the production conditions typically have to be empirically derived including, but not limited to, mammalian cell line development, media optimization, and upstream engineering. Furthermore, other production development goals, such as protein titer, upstream robustness and in-process controls, are often sacrificed when realizing the desired glycan compositions. For example, glucose feeding during upstream production may need to be controlled in order to minimize high mannose formation on the protein product, leading to slower cell metabolizing rates, cell growth and decreased productivity.

Thus, there is a need in the biopharmaceutical industry for production of mAb from CHO and other mammalian cell expression systems that exhibit predictable, consistent and reproducible glyco-form profiles.

SUMMARY OF THE INVENTION

Described herein are compositions and methods to improve glycosylation maturation of and to minimize the culture process-dependent effects of Fc-containing molecules, e.g., Fc-fusion molecules and antibodies. Creating single and multiple amino acid substitutions within the Fc domain with the aim to improve high mannose processing and glycosylation maturation, surprisingly caused the cells to consistently produce mAbs that showed more matured and less heterogeneous glycan profiles providing achievement of better product quality control as well as desired therapeutic efficacy.

In a first aspect, the invention relates to an Fc-containing molecule, such as an antibody or Fc-fusion molecule, comprising an amino acid substitution at position 239, 241, 262, 264, 265, 296, or 301. Preferred substitutions at position 239 include, but are not limited to, S239D, S239E, and S239K. A preferred substitution at position 241 is F241A. A preferred substitution at position 262 is V262A. Preferred substitutions at position 264 include, but are not limited to, V264D, V264L, V264A, and V264S. Preferred substitutions at position 265 include, but are not limited to, D265A, D265V, and D265S. A preferred substitution at position 2% includes, but is not limited to, F2% A. A preferred substitution at position 301 is F301A.

In one embodiment, the Fc-containing molecule comprises an S239D substitution.

In one embodiment, the Fc-containing molecule comprises an F241A substitution.

In one embodiment, the Fc-containing molecule comprises an V262A substitution.

In another embodiment, the Fc-containing molecule comprises a V264D substitution.

In another embodiment, the Fc-containing molecule comprises a V264L substitution.

In another embodiment, the Fc-containing molecule comprises a D265A substitution.

In another embodiment, the Fc-containing molecule comprises a D265V substitution.

In another embodiment, the Fc-containing molecule comprises a D265S substitution.

In another embodiment, the Fc-containing molecule comprises an F296A substitution.

In one embodiment, the Fc-containing molecule comprises an F301A substitution.

Included within the scope of the invention are Fc-containing molecules having combinations of substitutions at positions 239, 241, 262, 264, 265, 296, or 301. Preferred combinations include, but are not limited to, substitutions at positions 239 and 264 (e.g., S239D and V264D or S239D and V264L), at positions 239 and 265 (e.g., S239D and D265A), at positions 264 and 2% (e.g., V264D and F2%A), and at positions 264 and 265 (e.g., V264L and D265A).

In certain embodiments of the first aspect, the Fc-containing molecule is an antibody. In other embodiments, the Fc-containing molecule is an Fc-fusion protein.

In preferred embodiments of the first aspect, the Fc-containing molecule is glycosylated. The Fc-containing molecule may be glycosylated through expression in a mammalian host cell, such as a CHO cell.

In a second aspect, the invention relates to a composition comprising Fc-containing molecules of the first aspect wherein greater than 40% of the Fc-containing molecules comprise mature N-linked glycosylation (G1, G1F, G2, G2F, G2 F SA1, and G2 FSA2). In preferred embodiments, greater than 45%, greater than 50%, greater than 55%, greater than 60%, greater than 65%, greater than 70%, greater than 75%, or greater than 80% of the Fc-containing molecules comprise mature N-linked glycosylation. In certain embodiments, the percentage of Fc-containing molecules comprising mature N-linked glycosylation is between 40% and 85%, 45% and 85%, 50% and 85%, 55% and 85%, 60% and 85%, 65% and 85%, 70% and 85%, 75% and 85%, or 80% and 85%. In certain embodiments of the second aspect, mature N-linked glycosylation is less than 90%.

In a third aspect, the invention relates to a composition comprising Fc-containing molecules of the first aspect wherein less than 50% of the Fc-containing molecules comprise immature N-linked glycosylation (G0 and G0F). In preferred embodiments, less than 45%, less than 40%, less than 35%, less than 30%, less than 25%, less than 20%, less than 15%, less than 10%, or less than 5% of the Fc-containing molecules comprise immature N-linked glycosylation.

In a third aspect, the invention relates to a composition comprising Fc-containing molecules of the first aspect wherein less than 50% of the Fc-containing molecules comprise immature N-linked glycosylation (G0 and G0F). In preferred embodiments, less than 45%, less than 40%, less than 35%, less than 30%, less than 25%, less than 20%, less than 15%, less than 10%, or less than 5% of the Fc-containing molecules comprise immature N-linked glycosylation.

In a forth aspect, the invention relates to a composition comprising Fc-containing molecules of the first aspect wherein less than 5% of the Fc-containing molecules comprise mannose 5 (M5) N-linked glycosylation. In preferred embodiments, less than 4%, less than 3%, or less than 2% of the Fc-containing molecules comprise mannose 5 (M5) N-linked glycosylation.

In a fifth aspect, the invention relates to a polypeptide comprising an Fc region, wherein said Fc region comprises an amino acid substitution at position 239, 241, 262, 264, 265, 296, or 301. Preferred substitutions at position 239 include, but are not limited to, S239D, S239E, and S239K. A preferred substitution at position 241 is F241A. A preferred substitution at position 262 is V262A. Preferred substitutions at position 264 include, but are not limited to, V264D, V264L, V264A, and V264S. Preferred substitutions at position 265 include, but are not limited to, D265A, D265V, and D265S. A preferred substitution at position 2% includes, but is not limited to, F296A. A preferred substitution at position 301 is F301A.

In one embodiment, the polypeptide comprises an S239D substitution in the Fc region.

In one embodiment, the polypeptide comprises an F241A substitution in the Fc region.

In one embodiment, the polypeptide comprises an V262A substitution in the Fc region.

In another embodiment, the polypeptide comprises a V264D substitution in the Fc region.

In another embodiment, the polypeptide comprises a V264L substitution in the Fc region.

In another embodiment, the polypeptide comprises a D265A substitution in the Fc region.

In one embodiment, the polypeptide comprises an D265V substitution in the Fc region.

In another embodiment, the polypeptide comprises a D265S substitution in the Fc region.

In another embodiment, the polypeptide comprises an F296A substitution in the Fc region.

In one embodiment, the polypeptide comprises an F301A substitution in the Fc region.

In a sixth aspect, the invention relates to a nucleic acid encoding a polypeptide of the fifth aspect.

In a seventh aspect, an expression vector comprises a nucleic acid of the sixth aspect operably linked to a promoter.

In an eighth aspect, a host cell comprises one or more nucleic acids of the sixth aspect. In preferred embodiments, the host cell comprises one or more expression vectors of the seventh aspect.

In a ninth aspect, the invention relates to a method of producing an Fc-containing molecule. The method comprising culturing a host cell of the eighth aspect under conditions that cause expression of the Fc-containing molecule and isolating the Fc-containing molecule from the culture. In preferred embodiments, the Fc-containing molecule is secreted by the host cell and isolated from the growth medium.

In a tenth aspect, the invention relates to a method of producing a composition of the second, third, or fourth aspect. The method comprising culturing a host cell of the eighth aspect under conditions that cause expression of the Fc-containing molecule and isolating the Fc-containing molecule from the culture to obtain a Fc-containing molecule composition. In preferred embodiments, the Fc-containing molecule is secreted by the host cell and isolated from the growth medium.

BRIEF DESCRIPTION OF THE DRAWINGS

FIG. 7 Binding affinity of wild-type and Fc-variant antibodies to a cytokine receptor.

DETAILED DESCRIPTION

Figure 1:
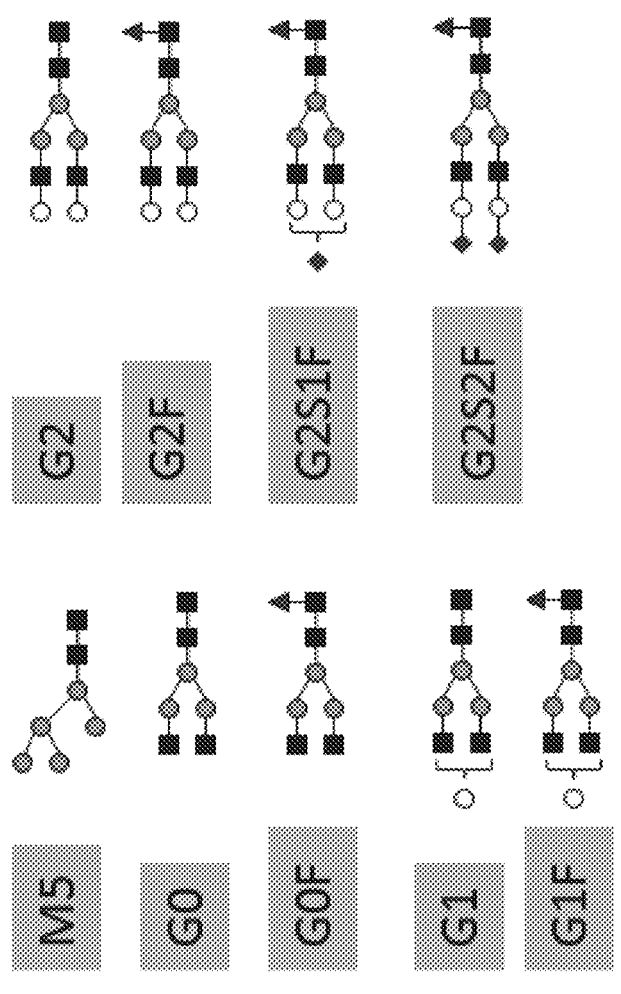
FIG. 1 Structure of N-Glycans found in mammalian cell-derived IgG.

The section headings used herein are for organizational purposes only and are not to be construed as limiting the subject matter described. All references cited within the body of this specification are expressly incorporated by reference in their entirety.

Standard techniques may be used for recombinant DNA, oligonucleotide synthesis, tissue culture and transformation, protein purification, etc. Enzymatic reactions and purification techniques may be performed according to the manufacturer's specifications or as commonly accomplished in the art or as described herein. The following procedures and techniques may be generally performed according to conventional methods well known in the art and as described in various general and more specific references that are cited and discussed throughout the specification. See. e.g., Sambrook et al., 2001, *Molecular Cloning: A Laboratory Manuel,* 3$^{rd}$ ed., Cold Spring Harbor Laboratory Press, cold Spring Harbor, N.Y., which is incorporated herein by reference for any purpose. Unless specific definitions are provided, the nomenclature used in connection with, and the laboratory procedures and techniques of, analytic chemistry, organic chemistry, and medicinal and pharmaceutical chemistry described herein are those well-known and commonly used in the art. Standard techniques may be used for chemical synthesis, chemical analyses, pharmaceutical preparation, formulation, and delivery and treatment of patients.

Definitions

The term "high mannose" ("HM") when used herein refers to a two N-acetylglucosamines with five or more many mannose residues The term "M5" when used herein refers to mannose 5, N-linked oligosaccharide with 5 mannosyl residues, $Man_5GlcNac_2$.

The term "G0" when used herein refers to a complex bi-antennary oligosaccharide without galactose or fucose, $GlcNAc_2Man_3GlcNAc_2$.

The term "G0F" when used herein refers to a complex bi-antennary oligosaccharide containing a core fucose and without galactose, $GlcNAc_2Man_3GlcNAc_2Fuc$.

The term "G1" when used herein refers to a complex bi-antennary oligosaccharide without fucose and containing one galactosyl residue, $GalGlcNAc_2Man_3GlcNAc_2$.

The term "G1F" when used herein refers to a complex bi-antennary oligosaccharide containing a core fucose and one galactosyl residue, $GalGlcNAc_2Man_3GlcNAc_2Fuc$.

The term "G2" when used herein refers to a complex bi-antennary oligosaccharide without fucose and containing two galactosyl residues, $Gal_2GlcNAc_2Man_3GlcNAc_2$ The term "G2F" when used herein refers to a complex bi-antennary oligosaccharide containing a core fucose and two galactosyl residues, $Gal_2GlcNAc_2Man_3GlcNAc_2Fuc$.

The term "G2S1F" as used herein refers to a complex bi-antennary oligosaccharide containing a core fucose, two galactosyl residues, and one N-acetyl neuraminic acid residue, $NANAGal_2GlcNAc_2Man_3GlcNAc_2Fuc$ The term "G2S2F" as used herein refers to a complex bi-antennary oligosaccharide containing a core fucose, two galactosyl residues, and two N-acetyl neuraminic acid residues, $NANA_2Gal_2GlcNAc_2Man_3GlcNAc_2Fuc$.

The term "antibody" when used herein refers to an immunoglobulin molecule that binds to a specific antigen through at least one antigen binding site located in the variable region of the immunoglobulin molecule. An "immunoglobulin" is a tetrameric molecule. In a naturally occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)). The variable regions of each light/heavy chain pair form the antibody binding site such that an intact immunoglobulin has two binding sites.

Naturally occurring immunoglobulin chains exhibit the same general structure of relatively conserved framework regions (FR) joined by three hypervariable regions, also called complementarity determining regions or CDRs. From N-terminus to C-terminus, both light and heavy chains comprise the domains FR1, CDR1, FR2, CDR2, FR3, CDR3 and FR4. The assignment of amino acids to each domain is in accordance with the definitions of Kabat et al. in Sequences of Proteins of Immunological Interest, 5th Ed., US Dept. of Health and Human Services, PHS, NIH, NIH Publication no. 91-3242, 1991. Intact antibodies include polyclonal, monoclonal, chimeric, humanized or fully human having full length heavy and light chains.

An antibody may have one or more binding sites. If there is more than one binding site, the binding sites may be identical to one another or may be different. For example, a naturally occurring human immunoglobulin typically has two identical binding sites, while a "bispecific" or "bifunctional" antibody has two different binding sites.

The term "human antibody" includes all antibodies that have one or more variable and constant regions derived from human immunoglobulin sequences. In one embodiment, all of the variable and constant domains are derived from human immunoglobulin sequences (a fully human antibody). These antibodies may be prepared in a variety of ways, examples of which are described below, including through the immunization with an antigen of interest of a mouse that is genetically modified to express antibodies derived from human heavy and/or light chain-encoding genes. In certain embodiments, the heavy chain of a human antibody is altered in the CH2 domain to alter the glycosylation properties of the antibody when expressed in a recombinant cell line, such as CHO cells.

A humanized antibody has a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject. In one embodiment, certain amino acids in the framework and constant domains of the heavy and/or light chains of the non-human species antibody are mutated to produce the humanized antibody. In another embodiment, the constant domain(s) from a human antibody are fused to the variable domain(s) of a non-human species. Examples of how to make humanized antibodies may be found in U.S. Pat. Nos. 6,054,297, 5,886,152 and 5,877,293.

The term "chimeric antibody" refers to an antibody that contains one or more regions from one antibody and one or more regions from one or more other antibodies. In one example of a chimeric antibody, a portion of the heavy and/or light chain is identical with, homologous to, or derived from an antibody from a particular species or belonging to a particular antibody class or subclass, while the remainder of the chain(s) is/are identical with, homologous to, or derived from an antibody (-ies) from another species or belonging to another antibody class or subclass. Also included are fragments of such antibodies that exhibit the desired biological activity.

Fragments or analogs of antibodies can be readily prepared by those of ordinary skill in the art following the teachings of this specification and using techniques well-known in the art. Preferred amino- and carboxy-termini of fragments or analogs occur near boundaries of functional domains. Structural and functional domains can be identified by comparison of the nucleotide and/or amino acid sequence data to public or proprietary sequence databases. Computerized comparison methods can be used to identify sequence motifs or predicted protein conformation domains that occur in other proteins of known structure and/or function. Methods to identify protein sequences that fold into a known three-dimensional structure are known. See, e.g., Bowie et al., 1991, Science 253:164.

A "CDR grafted antibody" is an antibody comprising one or more CDRs derived from an antibody of a particular species or isotype and the framework of another antibody of the same or different species or isotype.

The term "Fc polypeptide" or "Fc region" as used herein includes native and mutein forms of polypeptides derived from the Fc region of an antibody. Truncated forms of such polypeptides containing the hinge region that promotes dimerization also are included. In certain embodiments, the Fc region comprises an antibody CH2 and CH3 domain. Along with extended serum half-life, fusion proteins comprising Fc moieties (and oligomers formed therefrom) offer the advantage of facile purification by affinity chromatography over Protein A or Protein G columns. Preferred Fc regions are derived from human IgG, which includes IgG1, IgG2, IgG3, and IgG4. Herein, specific residues within the Fc are identified by position. All Fc positions are based on the EU numbering scheme.

Any peptide or polypeptide may be covalently linked to an Fc region to create an "Fc fusion molecule" or "Fc fusion protein." A polypeptide or peptide may be inserted into one or more loops within the CH2 or CH3 domains of the Fc. Typically, a polypeptide or peptide is covalently linked to the N-terminus or C-terminus of the Fc. In preferred embodiments, the peptide or polypeptide and the Fc are expressed as a single polypeptide as the product of a gene fusion, i.e., encoded within a single open-reading frame.

In certain embodiments, the Fc-fusion protein comprises a linker between the Fc and the peptide or polypeptide of interest. Many different linker polypeptides are known in the art and may be used in the context of an Fc-fusion protein. In preferred embodiments, the Fc-fusion protein comprises one or more copies of a peptide consisting of GGGGS (SEQ ID NO:47), GGNGT (SEQ ID NO:48), or YGNGT (SEQ ID NO:49) between the Fc and the peptide or polypeptide of interest. In some embodiments, the polypeptide region between the Fc region and the peptide or polypeptide of interest region comprises a single copy of GGGGS, GGNGT, or YGNGT. The linkers GGNGT or YGNGT are glycosylated when expressed in the appropriate cells and such glycosylation may help stabilize the protein in solution and/or when administered in vivo. Thus, in certain embodiments, a Fc fusion protein comprises a glycosylated linker between the Fc region and the peptide or polypeptide of interest.

An exemplary human IgG1 Fc amino acid sequence is (SEQ ID NO: 1)
YICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSREEMTKNQVSLTCLVKGFYPSDIAVEWESNGQPENNYKTTPPV

LDSDGSFFLYSKLTVDKSRWQQGNVFSCSVMHEALHNHYTQKSLSLSPGK

In the above sequence, (SEQ ID NO: 2)
YICNVNHKPSNTKVDKKVEPKSCDKTHTCPPCPAPELLGGPSVFLFPPKP corresponds to the hinge region, (SEQ ID NO: 3)
KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ to the CH2 domain,
and (SEQ ID NO: 4)
VYTLPPSREEMTKNQVSLTCLVKGFYPSDIAVEWESNGQPENNYKTTPPV

LDSDGSFFLYSKLTVDKSRWQQGNVFSCSVMHEALHNHYTQKSLSLSPGK to the CH3 domain.

An exemplary human IgG2 Fc amino acid sequence is (SEQ ID NO: 5)
YTCNVDHKPSNTKVDKTVERKCCVECPPCPAPPVAGPSVFLFPPKPKDTL

MISRTPEVTCVVVDVSHEDPEVQFNWYVDGVEVHNAKTKPREEQFNSTFR

VVSVLTVVHQDWLNGKEYKCKVSNKGLPAPIEKTISKTKGQPREPQVYTL

PPSREEMTKNQVSLTCLVKGFYPSDIAVEWESNGQPENNYKTTPPMLDSD

GSFFLYSKLTVDKSRWQQGNVFSCSVMHEALHNHYTQKSLSLSPGK

In the above sequence (SEQ ID NO: 6)
YTCNVDHKPSNTKVDKTVERKCCVECPPCPAPPVAGPSVFLFPPKP corresponds to the hinge region, (SEQ ID NO: 7)
DTLMISRTPEVTCVVVDVSHEDPEVQFNWYVDGVEVHNAKTKPREPQFNS

TFRVVSVLTVVHQDWLNGKEYKCKVSNKGLPAPIEKTISKTKGQPREPQ to the CH2 domain,
and (SEQ ID NO: 8)
VYTLPPSREEMTKNQVSLTCLVKGFYPSDIAVEWESNGQPENNYKTTPPM

LDSDGSFFLYSKLTVDKSRWQQGNVFSCSVMHEALHNHYTQKSLSLSPGK to the CH3 domain.

Fc-Containing Polypeptides

Preferred Fc-containing polypeptides include, but are not limited to, those comprising an amino acid substitution at EU position 239, 241, 262, 264, 265, 296, or 301. As discusses below, such polypeptides may have one or more additional deletions, additions, or substitutions with the Fc region. Thus, within the scope of the invention are Fc-containing polypeptides having an amino acid substitution at EU position 239, 241, 262, 264, 265, 296, or 301 and are at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, and at least 99% identical to SEQ ID NO:1 or SEQ ID NO:5.

For amino acid sequences, sequence identity and/or similarity is determined by using standard techniques known in the art, including, but not limited to, the local sequence identity algorithm of Smith and Waterman, 1981, *Adv. Appl. Math.* 2:482, the sequence identity alignment algorithm of Needleman and Wunsch, 1970, *J. Mol. Biol.* 48:443, the search for similarity method of Pearson and Lipman, 1988, *Proc. Nat. Acad. Sci. U.S.A.* 85:2444, computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., 1984, *Nucl. Acid Res.* 12:387-395, preferably using the default settings, or by inspection. Preferably, percent identity is calculated by FastDB based upon the following parameters: mismatch penalty of 1; gap penalty of 1; gap size penalty of 0.33; and joining penalty of 30, "Current Methods in Sequence Comparison and Analysis," Macromolecule Sequencing and Synthesis, Selected Methods and Applications, pp 127-149 (1988), Alan R. Liss, Inc.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, 1987, *J. Mol. Evol.* 35:351-360; the method is similar to that described by Higgins and Sharp, 1989, *CABIOS* 5:151-153. Useful PILEUP parameters including a default gap weight of 3.00, a default gap length weight of 0.10, and weighted end gaps.

Another example of a useful algorithm is the BLAST algorithm, described in: Altschul et al., 1990, *J. Mol. Biol.* 215:403-410; Altschul et al., 1997, *Nucleic Acids Res.* 25:3389-3402; and Karin et al., 1993, *Proc. Natl. Acad. Sci. U.S.A.* 90:5873-5787. A particularly useful BLAST program is the WU-BLAST-2 program which was obtained from Altschul et al., 1996, *Methods in Enzymology* 266:460-480. WU-BLAST-2 uses several search parameters, most of which are set to the default values. The adjustable parameters are set with the following values: overlap span=1, overlap fraction=0.125, word threshold (T)=II. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al., 1993, *Nucl. Acids Res.* 25:3389-3402. Gapped BLAST uses BLOSUM-62 substitution scores; threshold T parameter set to 9; the two-hit method to trigger ungapped extensions, charges gap lengths of k a cost of 10+k; $X_u$ set to 16, and $X_g$ set to 40 for database search stage and to 67 for the output stage of the algorithms. Gapped alignments are triggered by a score corresponding to about 22 bits.

Amino acid substitutions are typically of single residues; insertions usually will be on the order of from about one (1) to about twenty (20) amino acid residues, although considerably larger insertions may be tolerated. Deletions range from about one (1) to about twenty (20) amino acid residues, although in some cases deletions may be much larger.

Substitutions, deletions, insertions or any combination thereof may be used to arrive at a final derivative or variant. Generally these changes are done on a few amino acids to minimize the alteration of the molecule, particularly the immunogenicity and specificity of the antigen binding protein. However, larger changes may be tolerated in certain circumstances. Conservative substitutions are generally made in accordance with the following chart depicted as TABLE 1.

TABLE 1

| Original Residue | Exemplary Substitutions |
| --- | --- |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in TABLE 1. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine.

Preferred substitutions at position 239 include, but are not limited to, S239D, S239E, and S239K.

The variants often exhibit the same qualitative biological activity and will elicit the same immune response as the naturally-occurring analogue, although variants also are selected to modify the characteristics of the Fc-containing proteins as needed. Alternatively, the variant may be designed such that the biological activity of the Fc-containing protein is altered.

Exemplary Fc-containing polypeptides having a position 239 substitution include:

S239D

```
                                    (IgG1; SEQ ID NO: 9)
YICNVNHKPSNTKVDKKVEPKSCDKTHTCPPCPAPELLGGPDVFLFPPKP
KDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQ
VYTLPPSREEMTKNQVSLTCLVKGFYPSDIAVEWESNGQPENNYKTTPPV
LDSDGSFFLYSKLTVDKSRWQQGNVFSCSVMHEALHNHYTQKSLSLSPGK
```

-continued

```
                                    (IgG2; SEQ ID NO: 10)
YTCNVDHKPSNTKVDKTVERKCCVECPPCPAPPVAGPDVFLFPPKPKDTL
MISRTPEVTCVVVDVSHEDPEVQFNWYVDGVEVHNAKTKPREEQFNSTFR
VVSVLTVVHQDWLNGKEYKCKVSNKGLPAPIEKTISKTKGQPREPQVYTL
PPSREEMTKNQVSLTCLVKGFYPSDIAVEWESNGQPENNYKTTPPMLDSD
GSFFLYSKLTVDKSRWQQGNVFSCSVMHEALHNHYTQKSLSLSPGK
```

S239E

```
                                    (IgG1; SEQ ID NO: 11)
YICNVNHKPSNTKVDKKVEPKSCDKTHTCPPCPAPELLGGPEVFLFPPKP
KDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQ
VYTLPPSREEMTKNQVSLTCLVKGFYPSDIAVEWESNGQPENNYKTTPPV
LDSDGSFFLYSKLTVDKSRWQQGNVFSCSVMHEALHNHYTQKSLSLSPGK
```

```
                                    (IgG2; SEQ ID NO: 12)
YTCNVDHKPSNTKVDKTVERKCCVECPPCPAPPVAGPEVFLFPPKPKDTL
MISRTPEVTCVVVDVSHEDPEVQFNWYVDGVEVHNAKTKPREEQFNSTFR
VVSVLTVVHQDWLNGKEYKCKVSNKGLPAPIEKTISKTKGQPREPQVYTL
PPSREEMTKNQVSLTCLVKGFYPSDIAVEWESNGQPENNYKTTPPMLDSD
GSFFLYSKLTVDKSRWQQGNVFSCSVMHEALHNHYTQKSLSLSPGK
```

S239K

```
                                    (IgG1; SEQ ID NO: 13)
YICNVNHKPSNTKVDKKVEPKSCDKTHTCPPCPAPELLGGPKVFLFPPKP
KDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQ
VYTLPPSREEMTKNQVSLTCLVKGFYPSDIAVEWESNGQPENNYKTTPPV
LDSDGSFFLYSKLTVDKSRWQQGNVFSCSVMHEALHNHYTQKSLSLSPGK
```

```
                                    (IgG2; SEQ ID NO: 14)
YTCNVDHKPSNTKVDKTVERKCCVECPPCPAPPVAGPKVFLFPPKPKDTL
MISRTPEVTCVVVDVSHEDPEVQFNWYVDGVEVHNAKTKPREEQFNSTFR
VVSVLTVVHQDWLNGKEYKCKVSNKGLPAPIEKTISKTKGQPREPQVYTL
PPSREEMTKNQVSLTCLVKGFYPSDIAVEWESNGQPENNYKTTPPMLDSD
GSFFLYSKLTVDKSRWQQGNVFSCSVMHEALHNHYTQKSLSLSPGK
```

Exemplary Fc-containing polypeptides having a position 241 substitution include:

F241A

```
                                    (IgG1; SEQ ID NO: 50)
YICNVNHKPSNTKVDKKVEPKSCDKTHTCPPCPAPELLGGPSVALFPPKP
KDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQ
VYTLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSPGK
```

```
                                    (IgG2; SEQ ID NO: 51)
YTCNVDHKPSNTKVDKTVERKCCVECPPCPAPPVAGPSVALFPPKPKDTL
MISRTPEVTCVVVDVSHEDPEVQFNWYVDGVEVHNAKTKPREEQFNSTFR
VVSVLTVVHQDWLNGKEYKCKVSNKGLPAPIEKTISKTKGQPREPQVYTL
PPSREEMTKNQVSLTCLVKGFYPSDIAVEWESNGQPENNYKTTPPMLDSD
GSFFLYSKLTVDKSRWQQGNVFSCSVMHEALHNHYTQKSLSLSPGK
```

Exemplary Fc-containing polypeptides having a position 262 substitution include:

V262A

```
                                    (IgG1; SEQ ID NO: 52)
YICNVNHKPSNTKVDKKVEPKSCDKTHTCPPCPAPELLGGPSVFLFPPKP
KDTLMISRTPEVTCAVVDVSHEDPEVKFNWYVDGVEVHNAKTKPREEQYN
STYRVVSVLTVLHQDWLNGKEYKCKVSNKALPAPIEKTISKAKGQPREPQ
VYTLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSPGK
```

```
                                    (IgG2; SEQ ID NO: 53)
YTCNVDHKPSNTKVDKTVERKCCVECPPCPAPPVAGPSVFLFPPKPKDTL
MISRTPEVTCAVVDVSHEDPEVQFNWYVDGVEVHNAKTKPREEQFNSTFR
VVSVLTVVHQDWLNGKEYKCKVSNKGLPAPIEKTISKTKGQPREPQVYTL
PPSREEMTKNQVSLTCLVKGFYPSDIAVEWESNGQPENNYKTTPPMLDSD
GSFFLYSKLTVDKSRWQQGNVFSCSVMHEALHNHYTQKSLSLSPGK
```

Exemplary Fc-containing polypeptides having a position 264 substitution include:

V264D

```
                              (IgG1; SEQ ID NO: 15)
YICNVNHKPSNTKVDKKVEPKSCDKTHTCPPCPAPELLGGPSVFLFPPKP
KDTLMISRTPEVTCVVDDVSHEDPEVKFNWYVDGVEVHNAKTKPREEQYN
STYRVVSVLTVLHQDWLNGKEYKCKVSNKALPAPIEKTISKAKGQPREPQ
VYTLPPSREEMTKNQVSLTCLVKGFYPSDIAVEWESNGQPENNYKTTPPV
LDSDGSFFLYSKLTVDKSRWQQGNVFSCSVMHEALHNHYTQKSLSLSPGK
```

```
                              (IgG2; SEQ ID NO: 16)
YTCNVDHKPSNTKVDKTVERKCCVECPPCPAPPVAGPSVFLFPPKPKDTL
MISRTPEVTCVVDDVSHEDPEVQFNWYVDGVEVHNAKTKPREEQFNSTFR
VVSVLTVVHQDWLNGKEYKCKVSNKGLPAPIEKTISKTKGQPREPQVYTL
PPSREEMTKNQVSLTCLVKGFYPSDIAVEWESNGQPENNYKTTPPMLDSD
GSFFLYSKLTVDKSRWQQGNVFSCSVMHEALHNHYTQKSLSLSPGK
```

V264L

```
                              (IgG1; SEQ ID NO: 17)
YICNVNHKPSNTKVDKKVEPKSCDKTHTCPPCPAPELLGGPSVFLFPPKP
KDTLMISRTPEVTCVVLDVSHEDPEVKFNWYVDGVEVHNAKTKPREEQYN
STYRVVSVLTVLHQDWLNGKEYKCKVSNKALPAPIEKTISKAKGQPREPQ
VYTLPPSREEMTKNQVSLTCLVKGFYPSDIAVEWESNGQPENNYKTTPPV
LDSDGSFFLYSKLTVDKSRWQQGNVFSCSVMHEALHNHYTQKSLSLSPGK
```

```
                              (IgG2; SEQ ID NO: 18)
YTCNVDHKPSNTKVDKTVERKCCVECPPCPAPPVAGPSVFLFPPKPKDTL
MISRTPEVTCVVLDVSHEDPEVQFNWYVDGVEVHNAKTKPREEQFNSTFR
VVSVLTVVHQDWLNGKEYKCKVSNKGLPAPIEKTISKTKGQPREPQVYTL
PPSREEMTKNQVSLTCLVKGFYPSDIAVEWESNGQPENNYKTTPPMLDSD
GSFFLYSKLTVDKSRWQQGNVFSCSVMHEALHNHYTQKSLSLSPGK
```

V264A

```
                              (IgG1; SEQ ID NO: 19)
YICNVNHKPSNTKVDKKVEPKSCDKTHTCPPCPAPELLGGPSVFLFPPKP
KDTLMISRTPEVTCVVADVSHEDPEVKFNWYVDGVEVHNAKTKPREEQYN
STYRVVSVLTVLHQDWLNGKEYKCKVSNKALPAPIEKTISKAKGQPREPQ
VYTLPPSREEMTKNQVSLTCLVKGEYPSDIAVEWESNGQPENNYKTTPPV
LDSDGSFFLYSKLTVDKSRWQQGNVFSCSVMHEALHNHYTQKSLSLSPGK
```

```
                              (IgG2; SEQ ID NO: 20)
YTCNVDHKPSNTKVDKTVERKCCVECPPCPAPPVAGPSVFLFPPKPKDTL
MISRTPEVTCVVADVSHEDPEVQFNWYVDGVEVHNAKTKPREEQFNSTFR
VVSVLTVVHQDWLNGKEYKCKVSNKGLPAPIEKTISKTKGQPREPQVYTL
PPSREEMTKNQVSLTCLVKGFYPSDIAVEWESNGQPENNYKTTPPMLDSD
GSFFLYSKLTVDKSRWQQGNVFSCSVMHEALHNHYTQKSLSLSPGK
```

V264S

```
                              (IgG1; SEQ ID NO: 21)
YICNVNHKPSNTKVDKKVEPKSCDKTHTCPPCPAPELLGGPSVFLFPPKP
KDTLMISRTPEVTCVVSDVSHEDPEVKFNWYVDGVEVHNAKTKPREEQYN
STYRVVSVLTVLHQDWLNGKEYKCKVSNKALPAPIEKTISKAKGQPREPQ
VYTLPPSREEMTKNQVSLTCLVKGFYPSDIAVEWESNGQPENNYKTTPPV
LDSDGSFFLYSKLTVDKSRWQQGNVFSCSVMHEALHNHYTQKSLSLSPGK
```

```
                              (IgG2; SEQ ID NO: 22)
YTCNVDHKPSNTKVDKTVERKCCVECPPCPAPPVAGPSVFLFPPKPKDTL
MISRTPEVTCVVSDVSHEDPEVQFNWYVDGVEVHNAKTKPREEQFNSTFR
VVSVLTVVHQDWLNGKEYKCKVSNKGLPAPIEKTISKTKGQPREPQVYTL
PPSREEMTKNQVSLTCLVKGFYPSDIAVEWESNGQPENNYKTTPPMLDSD
GSFFLYSKLTVDKSRWQQGNVFSCSVMHEALHNHYTQKSLSLSPGK
```

Exemplary Fc-containing polypeptides having a position 265 substitution include:

D265A

```
                              (IgG1; SEQ ID NO: 23)
YICNVNHKPSNTKVDKKVEPKSCDKTHTCPPCPAPELLGGPSVFLFPPKP
KDTLMISRTPEVTCVVVAVSHEDPEVKFNWYVDGVEVHNAKTKPREEQYN
STYRVVSVLTVLHQDWLNGKEYKCKVSNKALPAPIEKTISKAKGQPREPQ
VYTLPPSREEMTKNQVSLTCLVKGFYPSDIAVEWESNGQPENNYKTTPPV
LDSDGSFFLYSKLTVDKSRWQQGNVFSCSVMHEALHNHYTQKSLSLSPGK
```

```
                              (IgG2; SEQ ID NO: 24)
YTCNVDHKPSNTKVDKTVERKCCVECPPCPAPPVAGPSVFLFPPKPKDTL
MISRTPEVTCVVVAVSHEDPEVQFNWYVDGVEVHNAKTKPREEQFNSTFR
VVSVLTVVHQDWLNGKEYKCKVSNKGLPAPIEKTISKTKGQPREPQVYTL
```

```
-continued
PPSREEMTKNQVSLTCLVKGFYPSDIAVEWESNGQPENNYKTTPPMLDSD
GSFFLYSKLTVDKSRWQQGNVFSCSVMHEALHNHYTQKSLSLSPGK
```

D265S

```
                              (IgG1; SEQ ID NO: 25)
YICNVNHKPSNTKVDKKVEPKSCDKTHTCPPCPAPELLGGPSVFLFPPKP
KDTLMISRTPEVTCVVVSVSHEDPEVKFNWYVDGVEVHNAKTKPREEQYN
STYRVVSVLTVLHQDWLNGKEYKCKVSNKALPAPIEKTISKAKGQPREPQ
VYTLPPSREEMTKNQVSLTCLVKGFYPSDIAVEWESNGQPENNYKTTPPV
LDSDGSFFLYSKLTVDKSRWQQGNVFSCSVMHEALHNHYTQKSLSLSPGK
```

```
                              (IgG2; SEQ ID NO: 26)
YTCNVDHKPSNTKVDKTVERKCCVECPPCPAPPVAGPSVFLFPPKPKDTL
MISRTPEVTCVVVSVSHEDPEVQFNWYVDGVEVHNAKTKPREEQFNSTFR
VVSVLTVVHQDWLNGKEYKCKVSNKGLPAPIEKTISKTKGQPREPQVYTL
PPSREEMTKNQVSLTCLVKGFYPSDIAVEWESNGQPENNYKTTPPMLDSD
GSFFLYSKLTVDKSRWQQGNVFSCSVMHEALHNHYTQKSLSLSPGK
```

D265V

```
                              (IgG1; SEQ ID NO: 54)
YICNVNHKPSNTKVDKKVEPKSCDKTHTCPPCPAPELLGGPSVFLFPPKP
KDTLMISRTPEVTCVVVVVSHEDPEVKFNWYVDGVEVHNAKTKPREEQYN
STYRVVSVLTVLHQDWLNGKEYKCKVSNKALPAPIEKTISKAKGQPREPQ
VYTLPPSREEMTKNQVSLTCLVKGFYPSDIAVEWESNGQPENNYKTTPPV
LDSDGSFFLYSKLTVDKSRWQQGNVFSCSVMHEALHNHYTQKSLSLSPGK
```

```
                              (IgG2; SEQ ID NO: 55)
YTCNVDHKPSNTKVDKTVERKCCVECPPCPAPPVAGPSVFLFPPKPKDTL
MISRTPEVTCVVVVVSHEDPEVQFNWYVDGVEVHNAKTKPREEQFNSTFR
VVSVLTVVHQDWLNGKEYKCKVSNKGLPAPIEKTISKTKGQPREPQVYTL
PPSREEMTKNQVSLTCLVKGFYPSDIAVEWESNGQPENNYKTTPPMLDSD
GSFFLYSKLTVDKSRWQQGNVFSCSVMHEALHNHYTQKSLSLSPGK
```

Exemplary Fc-containing polypeptides having a position 2% substitution include:

F296A or Y296A

```
                              (IgG1; SEQ ID NO: 27)
YICNVNHKPSNTKVDKKVEPKSCDKTHTCPPCPAPELLGGPSVFLFPPKP
KDTLMISRTPEVTCWVDVSHEDPEVKFNWYVDGVEVHNAKTKPREEQYNS
TARVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPGK
```

```
                              (IgG2; SEQ ID NO: 28)
YTCNVDHKPSNTKVDKTVERKCCVECPPCPAPPVAGPSVFLFPPKPKDTL
MISRTPEVTCVVVDVSHEDPEVQFNWYVDGVEVHNAKTKPREEQFNSTAR
VVSVLTVVHQDWLNGKEYKCKVSNKGLPAPIEKTISKTKGQPREPQVYTL
PPSREEMTKNQVSLTCLVKGFYPSDIAVEWESNGQPENNYKTTPPMLDSD
GSFFLYSKLTVDKSRWQQGNVFSCSVMHEALHNHYTQKSLSLSPGK
```

Exemplary Fc-containing polypeptides having a position 301 substitution include:

R301A

```
                              (IgG1; SEQ ID NO: 56)
YICNVNHKPSNTKVDKKVEPKSCDKTHTCPPCPAPELLGGPSVFLFPPKP
KDTLMISRTPEVTCVVVDVSHEDPEVKFNWYVDGVEVHNAKTKPREEQYN
STYAVVSVLTVLHQDWLNGKEYKCKVSNKALPAPIEKTISKAKGQPREPQ
VYTLPPSREEMTKNQVSLTCLVKGFYPSDIAVEWESNGQPENNYKTTPPV
LDSDGSFFLYSKLTVDKSRWQQGNVFSCSVMHEALHNHYTQKSLSLSPGK
```

```
                              (IgG2; SEQ ID NO: 57)
YTCNVDHKPSNTKVDKTVERKCCVECPPCPAPPVAGPSVFLFPPKPKDTL
MISRTPEVTCVVVDVSHEDPEVQFNWYVDGVEVHNAKTKPREEQFNSTFA
VVSVLTVVHQDWLNGKEYKCKVSNKGLPAPIEKTISKTKGQPREPQVYTL
PPSREEMTKNQVSLTCLVKGFYPSDIAVEWESNGQPENNYKTTPPMLDSD
GSFFLYSKLTVDKSRWQQGNVFSCSVMHEALHNHYTQKSLSLSPGK
```

In certain embodiments, the Fc-containing polypeptide has combinations of substitutions at positions 239, 264, 265, or 2%. Preferred combinations include, but are not limited to, substitutions at positions 239 and 264 (e.g., S239D and V264D or S239D and V264L), at positions 239 and 265 (e.g., S239D and D265A), at positions 264 and 265 (e.g., V264L and D265A), and at positions 264 and 296 (e.g., V264D and F2% A).

Exemplary Fc-containing polypeptides having combinations of substitutions include:

S239D and V264D (IgG1; SEQ ID NO: 29)
YICNVNHKPSNTKVDKKVEPKSCDKTHTCPPCPAPELLGGPDVFLFPPKP
KDTLMISRTPEVTCVVDDVSHEDPEVKFNWYVDGVEVHNAKTKPREEQYN
STYRVVSVLTVLHQDWLNGKEYKCKVSNKALPAPIEKTISKAKGQPREPQ
VYTLPPSREEMTKNQVSLTCLVKGFYPSDIAVEWESNGQPENNYKTTPPV
LDSDGSFFLYSKLTVDKSRWQQGNVFSCSVMHEALHNHYTQKSLSLSPGK (IgG2; SEQ ID NO: 30)
YTCNVDHKPSNTKVDKTVERKCCVECPPCPAPPVAGPDVFLFPPKPKDTL
MISRTPEVTCVVDDVSHEDPEVQFNWYVDGVEVHNAKTKPREEQFNSTFR
VVSVLTVVHQDWLNGKEYKCKVSNKGLPAPIEKTISKTKGQPREPQVYTL
PPSREEMTKNQVSLTCLVKGFYPSDIAVEWESNGQPENNYKTTPPMLDSD
GSFFLYSKLTVDKSRWQQGNVFSCSVMHEALHNHYTQKSLSLSPGK S239D and V264L (IgG1; SEQ ID NO: 31)
YICNVNHKPSNTKVDKKVEPKSCDKTHTCPPCPAPELLGGPDVFLFPPKP
KDTLMISRTPEVTCVVLDVSHEDPEVKFNWYVDGVEVHNAKTKPREEQYN
STYRVVSVLTVLHQDWLNGKEYKCKVSNKALPAPIEKTISKAKGQPREPQ
VYTLPPSREEMTKNQVSLTCLVKGFYPSDIAVEWESNGQPENNYKTTPPV
LDSDGSFFLYSKLTVDKSRWQQGNVFSCSVMHEALHNHYTQKSLSLSPGK (IgG2; SEQ ID NO: 32)
YTCNVDHKPSNTKVDKTVERKCCVECPPCPAPPVAGPDVFLFPPKPKDTL
MISRTPEVTCVVLDVSHEDPEVQFNWYVDGVEVHNAKTKPREEQFNSTFR
VVSVLTVVHQDWLNGKEYKCKVSNKGLPAPIEKTISKTKGQPREPQVYTL
PPSREEMTKNQVSLTCLVKGFYPSDIAVEWESNGQPENNYKTTPPMLDSD
GSFFLYSKLTVDKSRWQQGNVFSCSVMHEALHNHYTQKSLSLSPGK S239D and D265A (IgG1; SEQ ID NO: 33)
YICNVNHKPSNTKVDKKVEPKSCDKTHTCPPCPAPELLGGPDVFLFPPKP
KDTLMISRTPEVTCVVVAVSHEDPEVKFNWYVDGVEVHNAKTKPREEQYN
STYRVVSVLTVLHQDWLNGKEYKCKVSNKALPAPIEKTISKAKGQPREPQ
VYTLPPSREEMTKNQVSLTCLVKGFYPSDIAVEWESNGQPENNYKTTPPV
LDSDGSFFLYSKLTVDKSRWQQGNVFSCSVMHEALHNHYTQKSLSLSPGK (IgG2; SEQ ID NO: 34)
YTCNVDHKPSNTKVDKTVERKCCVECPPCPAPPVAGPDVFLFPPKPKDTL
MISRTPEVTCVVVAVSHEDPEVQFNWYVDGVEVHNAKTKPREEQFNSTFR
VVSVLTVVHQDWLNGKEYKCKVSNKGLPAPIEKTISKTKGQPREPQVYTL
PPSREEMTKNQVSLTCLVKGFYPSDIAVEWESNGQPENNYKTTPPMLDSD
GSFFLYSKLTVDKSRWQQGNVFSCSVMHEALHNHYTQKSLSLSPGK V264D and Y296A/F296A (IgG1; SEQ ID NO: 35)
YICNVNHKPSNTKVDKKVEPKSCDKTHTCPPCPAPELLGGPSVFLFPPKP
KDTLMISRTPEVTCVVDDVSHEDPEVKFNWYVDGVEVHNAKTKPREEQAN
STYRVVSVLTVLHQDWLNGKEYKCKVSNKALPAPIEKTISKAKGQPREPQ
VYTLPPSREEMTKNQVSLTCLVKGFYPSDIAVEWESNGQPENNYKTTPPV
LDSDGSFFLYSKLTVDKSRWQQGNVFSCSVMHEALHNHYTQKSLSLSPGK (IgG2; SEQ ID NO: 36)
YTCNVDHKPSNTKVDKTVERKCCVECPPCPAPPVAGPSVFLFPPKPKDTL
MISRTPEVTCVVDDVSHEDPEVQFNWYVDGVEVHNAKTKPREEQANSTFR
VVSVLTVVHQDWLNGKEYKCKVSNKGLPAPIEKTISKTKGQPREPQVYTL
PPSREEMTKNQVSLTCLVKGFYPSDIAVEWESNGQPENNYKTTPPMLDSD
GSFFLYSKLTVDKSRWQQGNVFSCSVMHEALHNHYTQKSLSLSPGK V264L and D265A (IgG1; SEQ ID NO: 58)
YICNVNHKPSNTKVDKKVEPKSCDKTHTCPPCPAPELLGGPSVFLFPPKP
KDTLMISRTPEVTCVVLAVSHEDPEVKFNWYVDGVEVHNAKTKPREEQYN
STYRVVSVLTVLHQDWLNGKEYKCKVSNKALPAPIEKTISKAKGQPREPQ
VYTLPPSREEMTKNQVSLTCLVKGFYPSDIAVEWESNGQPENNYKTTPPV
LDSDGSFFLYSKLTVDKSRWQQGNVFSCSVMHEALHNHYTQKSLSLSPGK (IgG2; SEQ ID NO: 59)
YTCNVDHKPSNTKVDKTVERKCCVECPPCPAPPVAGPSVFLFPPKPKDTL
MISRTPEVTCVVLAVSHEDPEVQFNWYVDGVEVHNAKTKPREEQFNSTFR
VVSVLTVVHQDWLNGKEYKCKVSNKGLPAPIEKTISKTKGQPREPQVYTL
PPSREEMTKNQVSLTCLVKGFYPSDIAVEWESNGQPENNYKTTPPMLDSD
GSFFLYSKLTVDKSRWQQGNVESCSVMHEALHNHYTQKSLSLSPGK Fc-containing polypeptides naturally form homodimers. However, Fc regions can be engineered to form heterodimers. Provided herein are Fc-containing molecules comprising a homodimer or heterodimer of Fc-containing polypeptides of the invention. In certain embodiments, an antibody comprises a dimer of Fc-containing polypeptides of the invention between the antibody heavy chains. In other embodiments, an Fc-fusion protein comprises a dimer of Fc-containing polypeptides of the invention. Fc-containing polypeptides also may be engineering to form a stable monomer. Thus, in certain embodiments, the Fc-containing molecule comprises a single Fc-containing polypeptide of the invention.

In preferred embodiments, the Fc-containing molecule comprises N-linked glycosylation. N-linked glycosylation of the Fc-containing molecule can be obtained by expression of the molecule in an appropriate host cell, such as a mammalian host cell. In particularly preferred embodiments, the host cell is a Chinese hamster ovary (CHO) cell.

Expression of the Fc-containing molecules in the appropriate host cell leads to compositions of Fc-containing molecules having desired N-linked glycosylation profiles. Typically, when Fc-containing molecules, such an antibodies, are produced by a host cell, analysis of the N-linked glycosylation of the Fc-containing molecules shows that the extent of glycosylation of the Fc-containing molecules within the population is heterogeneous (contains many different N-linked glycoforms). Moreover, the percentage of the various glycoforms within the population of Fc-containing molecule may vary significantly from batch to batch, even when the identical Fc-containing molecule is produced. The Fc variants of the invention provide compositions wherein a greater percentage of the Fc-containing molecules contain mature N-linked glycosylation as compared to a wild-type Fc, wherein a lower percentage of the Fc-containing molecules contain immature N-linked glycosylation, or wherein the batch-to-batch variance in glycoform percentage is reduced.

Method of analyzing the N-linked glycosylation of Fc-containing molecules are well known in the art, such as MALDI-TOF mass spectrometry or 2-aminobenzoic acid (2-AA) labeled hydrophilic interaction liquid chromatography (HILIC).

In preferred embodiments, a composition comprises Fc-containing molecules wherein greater than 40% of the Fc-containing molecules comprise mature N-linked glycosylation (G1, G1F, G2, G2F, G2S1F, and G2S2F). In some embodiments, greater than 45%, greater than 50%, greater than 55%, greater than 60%, greater than 65%, greater than 70%, greater than 75%, or greater than 80% of the Fc-containing molecules comprise mature N-linked glycosylation. In certain embodiments, the percentage of Fc-containing molecules comprising mature N-linked glycosylation is between 40% and 90%, 45% and 90%, 50% and 90%, 55% and 90%, 60% and 90%, 65% and 90%, 70% and 90%, 75% and 90%, or 80% and 90%.

In certain embodiments, a composition comprises Fc-containing molecules wherein less than 50% of the Fc-containing molecules comprise immature N-linked glycosylation (G0 and G0F). In preferred embodiments, less than 45%, less than 40%, less than 35%, less than 30%, less than 25%, less than 20%, less than 15%, less than 10%, or less than 5% of the Fc-containing molecules comprise immature N-linked glycosylation.

In certain embodiments, a composition comprises Fc-containing molecules wherein less than 5% of the Fc-containing molecules comprise mannose 5 (M5) N-linked glycosylation. In preferred embodiments, less than 4%, less than 3%, or less than 2% of the Fc-containing molecules comprise mannose 5 (M5) N-linked glycosylation.

It is contemplated that essentially any antibody may incorporate the glycosylation-improving Fc variants described herein. Exemplary antibodies (and the antigen to which they specifically bind) include, but are not limited to, those described in U.S. Pat. No. 7,947,809 and U.S. Patent Application Publication No. 20090041784 (glucagon receptor), U.S. Pat. Nos. 7,939,070, 7,833,527, 7,767,206, and 7,786,284 (IL-17 receptor A), U.S. Pat. Nos. 7,872,106 and 7,592,429 (Sclerostin), U.S. Pat. Nos. 7,871,611, 7,815,907, 7,037,498, 7,700,742, and U.S. Patent Application Publication No. 20100255538 (IGF-1 receptor), U.S. Pat. No. 7,868,140 (B7RP1), U.S. Pat. No. 7,807,159 and U.S. Patent Application Publication No. 20110091455 (myostatin), U.S. Pat. Nos. 7,736,644, 7,628,986, 7,524,496, and U.S. Patent Application Publication No. 20100111979 (deletion mutants of epidermal growth factor receptor), U.S. Pat. No. 7,728, 110 (SARS coronavirus), U.S. Pat. No. 7,718,776 and U.S. Patent Application Publication No. 20100209435 (OPGL), U.S. Pat. Nos. 7,658,924 and 7,521,053 (Angiopoietin-2), U.S. Pat. Nos. 7,601,818, 7,795,413, U.S. Patent Application Publication No. 20090155274, U.S. Patent Application Publication No. 20110040076 (NGF), U.S. Pat. No. 7,579, 186 (TGF-β type II receptor), U.S. Pat. No. 7,541,438 (connective tissue growth factor), U.S. Pat. No. 7,438,910 (IL1-R1), U.S. Pat. No. 7,423,128 (properdin), U.S. Pat. Nos. 7,411,057, 7,824,679, 7,109,003, 6,682,736, 7,132, 281, and 7,807,797 (CTLA-4), U.S. Pat. Nos. 7,084,257, 7,790,859, 7,335,743, 7,084,257, and U.S. Patent Application Publication No. 20110045537 (interferon-gamma), U.S. Pat. No. 7,932,372 (MAdCAM), U.S. Pat. No. 7,906,625, U.S. Patent Application Publication No. 20080292639, and U.S. Patent Application Publication No. 20110044986 (amyloid), U.S. Pat. Nos. 7,815,907 and 7,700,742 (insulin-like growth factor I), U.S. Pat. Nos. 7,566,772 and 7,964,193 (interleukin-10), U.S. Pat. Nos. 7,563,442, 7,288,251, 7,338, 660, 7,626,012, 7,618,633, and U.S. Patent Application Publication No. 20100098694 (CD40), U.S. Pat. No. 7,498, 420 (c-Met), U.S. Pat. Nos. 7,326,414, 7,592,430, and 7,728,113 (M-CSF), U.S. Pat. Nos. 6,924,360, 7,067,131, and 7,090,844 (MUC18), U.S. Pat. Nos. 6,235,883, 7,807, 798, and U.S. Patent Application Publication No. 20100305307 (epidermal growth factor receptor), U.S. Pat. Nos. 6,716,587, 7,872,113, 7,465,450, 7,186,809, 7,317, 090, and 7,638,606 (interleukin-4 receptor), U.S. Patent Application Publication No. 20110135657 (BETA-KLOTHO), U.S. Pat. Nos. 7,887,799 and 7,879,323 (fibroblast growth factor-like polypeptides), U.S. Pat. No. 7,867, 494 (IgE), U.S. Patent Application Publication No. 20100254975 (ALPHA-4 BETA-7), U.S. Patent Application Publication No. 20100197005 and U.S. Pat. No. 7,537,762 (ACTIVIN RECEPTOR-LIKE KINASE-1), U.S. Pat. No. 7,585,500 and U.S. Patent Application Publication No. 20100047253 (IL-13), U.S. Patent Application Publication No. 20090263383 and U.S. Pat. No. 7,449,555 (CD148), U.S. Patent Application Publication No. 20090234106 (ACTIVIN A), U.S. Patent Application Publication No. 20090226447 (angiopoietin-1 and angiopoietin-2), U.S. Patent Application Publication No. 20090191212 (Angiopoietin-2), U.S. Patent Application Publication No. 20090155164 (C-FMS), U.S. Pat. No. 7,537,762 (activin receptor-like kinase-1), U.S. Pat. No. 7,371,381 (galanin), U.S. Patent Application Publication No. 20070196376 (INSULIN-LIKE GROWTH FACTORS), U.S. Pat. Nos. 7,267, 960 and 7,741,115 (LDCAM), U.S. Pat. No. 7,265,212 (CD45RB), U.S. Pat. No. 7,709,611, U.S. Patent Application Publication No. 20060127393 and U.S. Patent Application Publication No. 20100040619 (DKK1), U.S. Pat. No. 7,807, 795, U.S. Patent Application Publication No. 20030103978 and U.S. Pat. No. 7,923,008 (osteoprotegerin), U.S. Patent Application Publication No. 20090208489 (OV064), U.S. Patent Application Publication No. 20080286284 (PSMA), U.S. Pat. No. 7,888,482, U.S. Patent Application Publication No. 20110165171, and U.S. Patent Application Publication No. 20110059063 (PAR2), U.S. Patent Application Publication No. 20110150888 (HEPCIDIN), U.S. Pat. No. 7,939, 640 (B7L-1), U.S. Pat. No. 7,915,391 (c-Kit), U.S. Pat. Nos. 7,807,796, 7,193,058, and 7,427,669 (ULBP), U.S. Pat. Nos. 7,786,271, 7,304,144, and U.S. Patent Application Publication No. 20090238823 (TSLP), U.S. Pat. No. 7,767,793 (SIGIRR), U.S. Pat. No. 7,705,130 (HER-3), U.S. Pat. No. 7,704,501 (ataxin-1-like polypeptide), U.S. Pat. Nos. 7,695, 948 and 7,199,224 (TNF-α converting enzyme), U.S. Patent Application Publication No. 20090234106 (ACTIVIN A), U.S. Patent Application Publication No. 20090214559 and U.S. Pat. No. 7,438,910 (IL1-R1), U.S. Pat. No. 7,579,186 (TGF-β type II receptor), U.S. Pat. No. 7,569,387 (TNF receptor-like molecules), U.S. Pat. No. 7,541,438, (connective tissue growth factor), U.S. Pat. No. 7,521,048 (TRAIL receptor-2), U.S. Pat. Nos. 6,319,499, 7,081,523, and U.S. Patent Application Publication No. 20080182976 (erythropoietin receptor), U.S. Patent Application Publication No. 20080166352 and U.S. Pat. No. 7,435,796 (B7RP1), U.S. Pat. No. 7,423,128 (properdin), U.S. Pat. Nos. 7,422,742 and 7,141,653 (interleukin-5), U.S. Pat. Nos. 6,740,522 and 7,411,050 (RANKL), U.S. Pat. No. 7,378,091 (carbonic anhydrase IX (CA IX) tumor antigen), U.S. Pat. Nos. 7,318,925 and 7,288,253 (parathyroid hormone), U.S. Pat. No. 7,285,269 (TNF), U.S. Pat. Nos. 6,692,740 and 7,270, 817 (ACPL), U.S. Pat. No. 7,202,343 (monocyte chemoattractant protein-1), U.S. Pat. No. 7,144,731 (SCF), U.S. Pat. Nos. 6,355,779 and 7,138,500 (4-1BB), U.S. Pat. No. 7,135,174 (PDGFD), U.S. Pat. Nos. 6,630,143 and 7,045, 128 (Flt-3 ligand), U.S. Pat. No. 6,849,450 (metalloproteinase inhibitor), U.S. Pat. No. 6,596,852 (LERK-5), U.S. Pat. No. 6,232,447 (LERK-6), U.S. Pat. No. 6,500,429 (brain-derived neurotrophic factor), U.S. Pat. No. 6,184,359 (epithelium-derived T-cell factor), U.S. Pat. No. 6,143,874 (neurotrophic factor NNT-1), U.S. Patent Application Publication No. 20110027287 (PROPROTEIN CONVERTASE SUBTILISIN KEXIN TYPE 9 (PCSK9)), U.S. Patent Application Publication No. 20110014201 (IL-18 RECEPTOR), and U.S. Patent Application Publication No. 20090155164 (C-FMS). The above patents and published patent applications are incorporated herein by reference in their entirety for purposes of their disclosure of antibody polypeptides, antibody encoding nucleic acids, host cells, vectors, methods of making antibodies, pharmaceutical compositions, and methods of treating diseases associated with the respective target of the antibody.

Optional Further Modifications

The antibodies and Fc-fusion proteins described herein may further comprise one of more mutations that affect their binding to one or more Fc receptors. One of the functions of the Fc portion of an antibody is to communicate to the immune system when the antibody binds its target. This is commonly referenced as "effector function." Communication leads to antibody-dependent cellular cytotoxicity (ADCC), antibody-dependent cellular phagocytosis (ADCP), and/or complement dependent cytotoxicity (CDC). ADCC and ADCP are mediated through the binding of the Fc to Fc receptors on the surface of cells of the immune system. CDC is mediated through the binding of the Fc with proteins of the complement system, e.g., C1q.

The IgG subclasses vary in their ability to mediate effector functions. For example, IgG1 is superior to IgG2 and IgG4 at mediating ADCC and CDC. The effector function of an antibody can be increased, or decreased, by introducing one or more mutations into the Fc. Embodiments of the invention include antibodies and Fc-fusion proteins having an Fc engineered to increase effector function (U.S. Pat. No. 7,317,091 and Strohl, Curr. Opin. Biotech., 20:685-691, 2009; both incorporated herein by reference in its entirety). Exemplary IgG1 Fc molecules having increased effector function include those having one or more of the following substitutions [numbering based on the EU numbering scheme]:

S239D/I332E
S239D/A330S/I332E
S239D/A330L/I332E
S298A/D333A/K334A
P247I/A339D
P247I/A339Q
D280H/K290S
D280H/K290S/S298D
D280H/K290S/S298V
F243L/R292P/Y300L
F243L/R292P/Y300L/P396L
F243L/R292P/Y300L/V305O/P396L
G236A/S239D/I332E
K326A/E333A
K326W/E333S
K290E/S298G/T299A
K290N/S298G/T299A
K290E/S298G/T299A/K326E
K290N/S298G/T299A/K326E
K334V
L235S+S239D+K334V
Q311M+K334V
S239D+K334V
F243V+K334V
E294L+K334V
S298T+K334V
E233L+Q311M+K334V
L234I+Q311M+K334V
S298T+K334V
A330M+K334V
A330F+K334V
Q311M+A330M+K334V
Q311M+A330F+K334V
S298T+A330M+K334V
S298T+A330F+K334V
S239D+A330M+K334V
S239D+S298T+K334V
L234Y+K290Y+Y296W
L234Y+F243V+Y296W
L234Y+E294L+Y296W
L234Y+Y296W
K290Y+Y296W

Further embodiments of the invention include antibodies and Fc-fusion proteins, having an Fc engineered to decrease effector function. Exemplary Fc molecules having decreased effector function include those having one or more of the following substitutions [numbering based on the EU numbering scheme]:

N297A (IgG1)
L234A/L235A (IgG1)
V234A/G237A (IgG2)
L235A/G237A/E318A (IgG4)
H268Q/V309L/A330S/A331S (IgG2)
C220S/C226S/C229S/P238S (IgG1)

C226S/C229S/E233P/L234V/L235A (IgG1)
L234F/L235E/P331S (IgG1)
S267E/L328F (IgG1)

Another method of increasing effector function of IgG Fc-containing proteins is by reducing the fucosylation of the Fc. Removal of the core fucose from the biantennary complex-type oligosaccharides attached to the Fc greatly increased ADCC effector function without altering antigen binding or CDC effector function. Several methods are known for reducing or abolishing fucosylation of Fc-containing molecules, e.g., antibodies. These include recombinant expression in certain mammalian cell lines including a FUT8 knockout cell line, variant CHO line Lec13, rat hybridoma cell line YB2/0, a cell line comprising a small interfering RNA specifically against the FUT8 gene, and a cell line coexpressing $\beta$-1,4-N-acetylglucosaminyltransferase III and Golgi $\beta$-mannosidase II. Thus, in certain embodiments, a composition comprises an antibody having reduced fucosylation or lacking fucosylation altogether.

Polynucleotides Encoding Engineered Antibodies and Fc Fusion Proteins

Encompassed within the invention are nucleic acids encoding antibody heavy chains or Fc-fusion proteins comprising a variant Fc described herein. Nucleic acid molecules of the invention include DNA and RNA in both single-stranded and double-stranded form, as well as the corresponding complementary sequences. DNA includes, for example, cDNA, genomic DNA, chemically synthesized DNA, DNA amplified by PCR, and combinations thereof. The nucleic acid molecules of the invention include full-length genes or cDNA molecules as well as a combination of fragments thereof. The nucleic acids of the invention are preferentially derived from human sources, but the invention includes those derived from non-human species, as well.

An "isolated nucleic acid" is a nucleic acid that has been separated from adjacent genetic sequences present in the genome of the organism from which the nucleic acid was isolated, in the case of nucleic acids isolated from naturally-occurring sources. In the case of nucleic acids synthesized enzymatically from a template or chemically, such as PCR products, cDNA molecules, or oligonucleotides for example, it is understood that the nucleic acids resulting from such processes are isolated nucleic acids. An isolated nucleic acid molecule refers to a nucleic acid molecule in the form of a separate fragment or as a component of a larger nucleic acid construct. In one preferred embodiment, the nucleic acids are substantially free from contaminating endogenous material. The nucleic acid molecule has preferably been derived from DNA or RNA isolated at least once in substantially pure form and in a quantity or concentration enabling identification, manipulation, and recovery of its component nucleotide sequences by standard biochemical methods (such as those outlined in Sambrook et al., Molecular Cloning: A Laboratory Manual, 2nd ed., Cold Spring Harbor Laboratory, Cold Spring Harbor, NY (1989)). Such sequences are preferably provided and/or constructed in the form of an open reading frame uninterrupted by internal non-translated sequences, or introns, that are typically present in eukaryotic genes. Sequences of non-translated DNA can be present 5' or 3' from an open reading frame, where the same do not interfere with manipulation or expression of the coding region.

The present invention also includes nucleic acids that hybridize under moderately stringent conditions, and more preferably highly stringent conditions, to nucleic acids encoding polypeptides as described herein. The basic parameters affecting the choice of hybridization conditions and guidance for devising suitable conditions are set forth by Sambrook, Fritsch, and Maniatis (1989, Molecular Cloning: A Laboratory Manual, Cold Spring Harbor Laboratory Press, Cold Spring Harbor, N.Y., chapters 9 and 11; and Current Protocols in Molecular Biology, 1995, Ausubel et al., eds., John Wiley & Sons, Inc., sections 2.10 and 6.3-6.4), and can be readily determined by those having ordinary skill in the art based on, for example, the length and/or base composition of the DNA. One way of achieving moderately stringent conditions involves the use of a prewashing solution containing 5×SSC, 0.5% SDS, 1.0 mM EDTA (pH 8.0), hybridization buffer of about 50% formamide, 6×SSC, and a hybridization temperature of about 55 degrees C. (or other similar hybridization solutions, such as one containing about 50% formamide, with a hybridization temperature of about 42 degrees C.), and washing conditions of about 60 degrees C., in 0.5×SSC, 0.1% SDS. Generally, highly stringent conditions are defined as hybridization conditions as above, but with washing at approximately 68 degrees C., 0.2×SSC, 0.1% SDS. SSPE (1×SSPE is 0.15M NaCl, 10 mM $NaH_2PO_4$, and 1.25 mM EDTA, pH 7.4) can be substituted for SSC (1×SSC is 0.15M NaCl and 15 mM sodium citrate) in the hybridization and wash buffers; washes are performed for 15 minutes after hybridization is complete. It should be understood that the wash temperature and wash salt concentration can be adjusted as necessary to achieve a desired degree of stringency by applying the basic principles that govern hybridization reactions and duplex stability, as known to those skilled in the art and described further below (see, e.g., Sambrook et al., 1989). When hybridizing a nucleic acid to a target nucleic acid of unknown sequence, the hybrid length is assumed to be that of the hybridizing nucleic acid. When nucleic acids of known sequence are hybridized, the hybrid length can be determined by aligning the sequences of the nucleic acids and identifying the region or regions of optimal sequence complementarity. The hybridization temperature for hybrids anticipated to be less than 50 base pairs in length should be 5 to 10 .degrees C. less than the melting temperature (Tm) of the hybrid, where Tm is determined according to the following equations. For hybrids less than 18 base pairs in length, Tm (degrees C.)=2(# of A+T bases)+4(# of #G+C bases). For hybrids above 18 base pairs in length, Tm (degrees C.)=81.5+16.6 (log 10 [Na+])+0.41(% G+C)−(600/N), where N is the number of bases in the hybrid, and [Na+] is the concentration of sodium ions in the hybridization buffer ([Na+] for 1×SSC=0.165M). Preferably, each such hybridizing nucleic acid has a length that is at least 15 nucleotides (or more preferably at least 18 nucleotides, or at least 20 nucleotides, or at least 25 nucleotides, or at least 30 nucleotides, or at least 40 nucleotides, or most preferably at least 50 nucleotides), or at least 25% (more preferably at least 50%, or at least 60%, or at least 70%, and most preferably at least 80%) of the length of the nucleic acid of the present invention to which it hybridizes, and has at least 60% sequence identity (more preferably at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, and most preferably at least 99.5%) with the nucleic acid of the present invention to which it hybridizes, where sequence identity is determined by comparing the sequences of the hybridizing nucleic acids when aligned so as to maximize overlap and identity while minimizing sequence gaps as described in more detail above.

Variants are ordinarily prepared by site specific mutagenesis of nucleotides in the DNA encoding the polypeptide, using cassette or PCR mutagenesis or other techniques well known in the art, to produce DNA encoding the variant, and thereafter expressing the recombinant DNA in cell culture as outlined herein. However, antibodies or antibody fragments comprising variant sequences may be prepared by in vitro synthesis using established techniques. The variants typically exhibit the same qualitative biological activity as the naturally occurring analogue, e.g., binding to antigen, although variants can also be selected which have modified characteristics as will be more fully outlined herein.

As will be appreciated by those in the art, due to the degeneracy of the genetic code, an extremely large number of nucleic acids may be made that encode a polypeptide of the invention. Thus, having identified a particular amino acid sequence, those skilled in the art could make any number of different nucleic acids, by simply modifying the sequence of one or more codons in a way which does not change the amino acid sequence of the encoded protein.

The invention also provides expression systems and constructs in the form of plasmids, expression vectors, transcription or expression cassettes which comprise at least one polynucleotide as above. In addition, the invention provides host cells comprising such expression systems or constructs.

Typically, expression vectors used in the host cells will contain sequences for plasmid maintenance and for cloning and expression of exogenous nucleotide sequences. Such sequences, collectively referred to as "flanking sequences," in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. Each of these sequences is discussed below.

Optionally, the vector may contain a "tag"-encoding sequence, i.e., an oligonucleotide molecule located at the 5' or 3' end of the polypeptide coding sequence; the oligonucleotide sequence encodes polyHis (such as hexaHis), or another "tag" such as FLAG, HA (hemaglutinin influenza virus), or myc, for which commercially available antibodies exist. This tag is typically fused to the polypeptide upon expression of the polypeptide, and can serve as a means for affinity purification or detection of the polypeptide from the host cell. Affinity purification can be accomplished, for example, by column chromatography using antibodies against the tag as an affinity matrix. Optionally, the tag can subsequently be removed from the purified polypeptide by various means such as using certain peptidases for cleavage.

Flanking sequences may be homologous (i.e., from the same species and/or strain as the host cell), heterologous (i.e., from a species other than the host cell species or strain), hybrid (i.e., a combination of flanking sequences from more than one source), synthetic or native. As such, the source of a flanking sequence may be any prokaryotic or eukaryotic organism, any vertebrate or invertebrate organism, or any plant, provided that the flanking sequence is functional in, and can be activated by, the host cell machinery.

Flanking sequences useful in the vectors of this invention may be obtained by any of several methods well known in the art. Typically, flanking sequences useful herein will have been previously identified by mapping and/or by restriction endonuclease digestion and can thus be isolated from the proper tissue source using the appropriate restriction endo-nucleases. In some cases, the full nucleotide sequence of a flanking sequence may be known. Here, the flanking sequence may be synthesized using the methods described herein for nucleic acid synthesis or cloning.

Whether all or only a portion of the flanking sequence is known, it may be obtained using polymerase chain reaction (PCR) and/or by screening a genomic library with a suitable probe such as an oligonucleotide and/or flanking sequence fragment from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen® column chromatography (Chatsworth, CA), or other methods known to the skilled artisan. The selection of suitable enzymes to accomplish this purpose will be readily apparent to one of ordinary skill in the art.

An origin of replication is typically a part of those prokaryotic expression vectors purchased commercially, and the origin aids in the amplification of the vector in a host cell. If the vector of choice does not contain an origin of replication site, one may be chemically synthesized based on a known sequence, and ligated into the vector. For example, the origin of replication from the plasmid pBR322 (New England Biolabs, Beverly, MA) is suitable for most gram-negative bacteria, and various viral origins (e.g., SV40, polyoma, adenovirus, vesicular stomatitus virus (VSV), or papillomaviruses such as HPV or BPV) are useful for cloning vectors in mammalian cells. Generally, the origin of replication component is not needed for mammalian expression vectors (for example, the SV40 origin is often used only because it also contains the virus early promoter).

A transcription termination sequence is typically located 3' to the end of a polypeptide coding region and serves to terminate transcription. Usually, a transcription termination sequence in prokaryotic cells is a G-C rich fragment followed by a poly-T sequence. While the sequence is easily cloned from a library or even purchased commercially as part of a vector, it can also be readily synthesized using methods for nucleic acid synthesis such as those described herein.

A selectable marker gene encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for pro-karyotic host cells; (b) complement auxotrophic deficiencies of the cell; or (c) supply critical nutrients not available from complex or defined media. Specific selectable markers are the kanamycin resistance gene, the ampicillin resistance gene, and the tetracycline resistance gene. Advantageously, a neomycin resistance gene may also be used for selection in both prokaryotic and eukaryotic host cells.

Other selectable genes may be used to amplify the gene that will be expressed. Amplification is the process wherein genes that are required for production of a protein critical for growth or cell survival are reiterated in tandem within the chromosomes of successive generations of recombinant cells. Examples of suitable selectable markers for mammalian cells include dihydrofolate reductase (DHFR) and pro-moterless thymidine kinase genes. Mammalian cell trans-formants are placed under selection pressure wherein only the transformants are uniquely adapted to survive by virtue of the selectable gene present in the vector. Selection pressure is imposed by culturing the transformed cells under conditions in which the concentration of selection agent in the medium is successively increased, thereby leading to the amplification of both the selectable gene and the DNA that encodes another gene, such as an antibody light or heavy chain. As a result, increased quantities of a polypeptide are synthesized from the amplified DNA.

A ribosome-binding site is usually necessary for translation initiation of mRNA and is characterized by a Shine-Dalgamo sequence (prokaryotes) or a Kozak sequence (eu-karyotes). The element is typically located 3' to the promoter and 5' to the coding sequence of the polypeptide to be expressed. In certain embodiments, one or more coding regions may be operably linked to an internal ribosome binding site (IRES), allowing translation of two open reading frames from a single RNA transcript.

In certain embodiments, one may manipulate the various pre- or prosequences to improve further glycosylation or yield. For example, one may alter the peptidase cleavage site of a particular signal peptide, or add prosequences, which also may affect glycosylation. The final protein product may have, in the −1 position (relative to the first amino acid of the mature protein) one or more additional amino acids incident to expression, which may not have been totally removed. For example, the final protein product may have one or two amino acid residues found in the peptidase cleavage site, attached to the amino-terminus. Alternatively, use of some enzyme cleavage sites may result in a slightly truncated form of the desired polypeptide, if the enzyme cuts at such area within the mature polypeptide.

Expression and cloning vectors of the invention will typically contain a promoter that is recognized by the host organism and operably linked to the molecule encoding the polypeptide. Promoters are untranscribed sequences located upstream (i.e., 5') to the start codon of a structural gene (generally within about 100 to 1000 bp) that control transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, uniformly transcribe gene to which they are operably linked, that is, with little or no control over gene expression. A large number of promoters, recognized by a variety of potential host cells, are well known. A suitable promoter is operably linked to the DNA encoding e.g., heavy chain or light chain, by removing the promoter from the source DNA by restriction enzyme digestion and inserting the desired promoter sequence into the vector.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus and most preferably Simian Virus 40 (SV40). Other suitable mammalian promoters include heterologous mammalian promoters, for example, heat-shock promoters and the actin promoter.

Additional promoters which may be of interest include, but are not limited to: SV40 early promoter (Benoist and Chambon, 1981, Nature 290:304-310); CMV promoter (Thornsen et al., 1984, Proc. Natl. Acad. U.S.A. 81:659-

663); the promoter contained in the 3' long terminal repeat of Rous sarcoma virus (Yamamoto et al., 1980, Cell 22:787-797); herpes thymidine kinase promoter (Wagner et al., 1981, Proc. Natl. Acad. Sci. U.S.A. 78:1444-1445); promoter and regulatory sequences from the metallothionine gene Prinster et al., 1982, Nature 296:39-42); and prokaryotic promoters such as the beta-lactamase promoter (Villa-Kamaroff et al., 1978, Proc. Natl. Acad. Sci. U.S.A. 75:3727-3731); or the tac promoter (DeBoer et al., 1983, Proc. Natl. Acad. Sci. U.S.A. 80:21-25). Also of interest are the following animal transcriptional control regions, which exhibit tissue specificity and have been utilized in transgenic animals: the elastase I gene control region that is active in pancreatic acinar cells (Swift et al., 1984, Cell 38:639-646; Omitz et al., 1986, Cold Spring Harbor Symp. Quant. Biol. 50:399-409; MacDonald, 1987, Hepatology 7:425-515); the insulin gene control region that is active in pancreatic beta cells (Hanahan, 1985, Nature 315:115-122); the immuno-globulin gene control region that is active in lymphoid cells (Grosschedl et al., 1984, Cell 38:647-658; Adames et al., 1985, Nature 318:533-538; Alexander et al., 1987, Mol. Cell. Biol. 7:1436-1444); the mouse mammary tumor virus control region that is active in testicular, breast, lymphoid and mast cells (Leder et al., 1986, Cell 45:485-495); the albumin gene control region that is active in liver (Pinkert et al., 1987, Genes and Devel. 1:268-276); the alpha-feto-protein gene control region that is active in liver (Krumlauf et al., 1985, Mol. Cell. Biol. 5:1639-1648; Hammer et al., 1987, Science 253:53-58); the alpha 1-antitrypsin gene control region that is active in liver (Kelsey et al., 1987, Genes and Devel. 1:161-171); the beta-globin gene control region that is active in myeloid cells (Mogram et al., 1985, Nature 315:338-340; Kollias et al., 1986, Cell 46:89-94); the myelin basic protein gene control region that is active in oligodendrocyte cells in the brain (Readhead et al., 1987, Cell 48:703-712); the myosin light chain-2 gene control region that is active in skeletal muscle (Sani, 1985, Nature 314:283-286); and the gonadotropic releasing hormone gene control region that is active in the hypothalamus (Mason et al., 1986, Science 234:1372-1378).

An enhancer sequence may be inserted into the vector to increase transcription of DNA encoding heavy chain or Fc-fusion protein of the invention by higher eukaryotes. Enhancers are cis-acting elements of DNA, usually about 10-300 bp in length, that act on the promoter to increase transcription. Enhancers are relatively orientation and position independent, having been found at positions both 5' and 3' to the transcription unit. Several enhancer sequences available from mammalian genes are known (e.g., globin, elastase, albumin, alpha-feto-protein and insulin). Typically, however, an enhancer from a virus is used. The SV40 enhancer, the cytomegalovirus early promoter enhancer, the polyoma enhancer, and adenovirus enhancers known in the art are exemplary enhancing elements for the activation of eukaryotic promoters. While an enhancer may be positioned in the vector either 5' or 3' to a coding sequence, it is typically located at a site 5' from the promoter. A sequence encoding an appropriate native or heterologous signal sequence (leader sequence or signal peptide) can be incorporated into an expression vector, to promote extracellular secretion of the antibody. The choice of signal peptide or leader depends on the type of host cells in which the antibody is to be produced, and a heterologous signal sequence can replace the native signal sequence. Examples of signal peptides that are functional in mammalian host cells include the following: the signal sequence for interleukin-7 (IL-7) described in U.S. Pat. No. 4,965,195; the signal sequence for interleukin-2 receptor described in Cosman et al., 1984, Nature 312:768; the interleukin-4 receptor signal peptide described in EP Patent No. 0367 566; the type I interleukin-1 receptor signal peptide described in U.S. Pat. No. 4,968,607; the type II interleukin-1 receptor signal peptide described in EP Patent No. 0 460 846.

The vector may contain one or more elements that facilitate expression when the vector is integrated into the host cell genome. Examples include an EASE element (Aldrich et al. 2003 Biotechnol. Prog. 19:1433-38) and a matrix attachment region (MAR). MARs mediate structural organization of the chromatin and may insulate the integrated vactor from "position" effect. Thus, MARs are particularly useful when the vector is used to create stable transfectants. A number of natural and synthetic MAR-containing nucleic acids are known in the art, e.g., U.S. Pat. Nos. 6,239,328; 7,326,567; 6,177,612; 6,388,066; 6,245,974; 7,259,010; 6,037,525; 7,422,874; 7,129,062.

Expression vectors of the invention may be constructed from a starting vector such as a commercially available vector. Such vectors may or may not contain all of the desired flanking sequences. Where one or more of the flanking sequences described herein are not already present in the vector, they may be individually obtained and ligated into the vector. Methods used for obtaining each of the flanking sequences are well known to one skilled in the art.

After the vector has been constructed and a nucleic acid molecule encoding a heavy chain or Fc-fusion protein has been inserted into the proper site of the vector, the completed vector may be inserted into a suitable host cell for amplification and/or polypeptide expression. The transformation of an expression vector into a selected host cell may be accomplished by well-known methods including transfection, infection, calcium phosphate co-precipitation, electroporation, microinjection, lipofection, DEAE-dextran mediated transfection, or other known techniques. The method selected will in part be a function of the type of host cell to be used. These methods and other suitable methods are well known to the skilled artisan, and are set forth, for example, in Sambrook et al., 2001, supra.

A host cell, when cultured under appropriate conditions, synthesizes the antibody or Fc-fusion protein that can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule. A host cell may be eukaryotic or prokaryotic.

Mammalian cell lines available as hosts for expression are well known in the art and include, but are not limited to, immortalized cell lines available from the American Type Culture Collection (ATCC) and any cell lines used in an expression system known in the art can be used to make the recombinant polypeptides of the invention. In general, host cells are transformed with a recombinant expression vector that comprises DNA encoding a desired heterodimeric antibody. Among the host cells that may be employed are prokaryotes, yeast or higher eukaryotic cells. Prokaryotes include gram negative or gram positive organisms, for example *E. coli* or bacilli. Higher eukaryotic cells include insect cells and established cell lines of mammalian origin. Exemplary host cells include Chinese hamster ovary (CHO) cell lines or their derivatives including CHO strain DXB-11, which is deficient in DHFR (see Urlaub et al., 1980, Proc.

Natl. Acad. Sci. USA 77:4216-20), CHO cell lines which grow in serum-free media (see Rasmussen et al., 1998, Cytotechnology 28:31), CS-9 cells, a derivative of DXB-11 CHO cells, and AM-1/D cells (described in U.S. Pat. No. 6,210,924). Other CHO cells lines include CHO-K1 (ATCC #CCL-61), EM9 (ATCC #CRL-1861), and UV20 (ATCC #CRL-1862). Examples of other host cells include COS-7 line of monkey kidney cells (ATCC CRL 1651) (see Gluzman et al., 1981, Cell 23:175), L cells, C127 cells, 3T3 cells (ATCC CCL 163), HeLa cells, BHK (ATCC CRL 10) cell lines, the CV1/EBNA cell line derived from the African green monkey kidney cell line CV1 (ATCC CCL 70) (see McMahan et al., 1991, EMBO J. 10:2821), human embryonic kidney cells such as 293, 293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells.

Alternatively, it is possible to produce the polypeptide in lower eukaryotes such as yeast or in prokaryotes such as bacteria. Suitable yeasts include Saccharomyces cerevisiae, Schizosaccharomyces pombe, Kluyveromyces strains, Candida, or any yeast strain capable of expressing heterologous polypeptides. Suitable bacterial strains include Escherichia coli, Bacillus subtilis, Salmonella typhimurium, or any bacterial strain capable of expressing heterologous polypeptides. However, preferred cell lines are those which demonstrate the improved glycosylation characteristics of the Fc variants described herein, such as Chinese Hamster Ovary cells, human embryonic kidney cell line (HEK)-293(T) and PerC6, murine melanoma cell line NS0, murine B cell line SP2/0, Drosophila cell such as Schneider 2 (S2) and Spodoptera frugiperda (SF) 9, Baby hamster kidney fibroblast cells (BHK-21), hybridoma cell lines, murine mammary tumor line C127, Saccharomyces cerevisiae, etc. If the antibody or fragment is made in yeast or bacteria, it may be desirable to modify the product produced therein, for example by phosphorylation or glycosylation of the appropriate sites, in order to obtain a functional product. Such covalent attachments can be accomplished using known chemical or enzymatic methods. A polypeptide can also be produced by operably linking the isolated nucleic acid of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the Max-Bac kit), and such methods are well known in the art, as described in Summers and Smith, Texas Agricultural Experiment Station Bulletin No. 1555 (1987), and Luckow and Summers, Bio/Technology 6:47 (1988). Cell-free translation systems could also be employed to produce polypeptides, such as antibodies or fragments, using RNAs derived from nucleic acid constructs disclosed herein. Appropriate cloning and expression vectors for use with bacterial, fungal, yeast, and mammalian cellular hosts are described by Pouwels et al. (Cloning Vectors: A Laboratory Manual, Elsevier, New York, 1985). A host cell that comprises an isolated nucleic acid of the invention, preferably operably linked to at least one expression control sequence, is a "recombinant host cell".

In certain embodiments, cell lines may be selected through determining which cell lines have high expression levels and produce antibodies or Fc-fusion proteins with the desired glycosylation properties.

Pharmaceutical Compositions

In some embodiments, the invention provides a pharmaceutical composition comprising a therapeutically effective amount of antibody or Fc-fusion protein of the invention together with a pharmaceutically effective diluents, carrier, solubilizer, emulsifier, preservative, and/or adjuvant. Pharmaceutical compositions of the invention include, but are not limited to, liquid, frozen, and lyophilized compositions.

Preferably, formulation materials are nontoxic to recipients at the dosages and concentrations employed. In specific embodiments, pharmaceutical compositions comprising a therapeutically effective amount of antibody or Fc-fusion protein are provided.

In some embodiments, the pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine, proline, or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. See, REMINGTON'S PHARMACEUTICAL SCIENCES, 18" Edition, (A. R. Gennaro, ed.), 1990, Mack Publishing Company.

In some embodiments, the optimal pharmaceutical composition will be determined by one skilled in the art depending upon, for example, the intended route of administration, delivery format and desired dosage. See, for example, REMINGTON'S PHARMACEUTICAL SCIENCES, supra. In certain embodiments, such compositions may influence the physical state, stability, rate of in vivo release and rate of in vivo clearance of the antibody or Fc-fusion protein. In certain embodiments, the primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. In specific embodiments, pharmaceutical compositions comprise Tris buffer of about pH 7.0-8.5, or acetate buffer of about pH 4.0-5.5, and may further include sorbitol or a suitable substitute therefor. In certain embodiments of the invention, the composition may be prepared for storage by mixing the selected composition having the desired degree of purity with optional formulation agents (REMINGTON'S PHARMACEUTICAL SCIENCES, supra) in the form of a lyophilized cake or an aqueous solution. Further, in some embodiments, the antibody or Fc-fusion protein may be formulated as a lyophilizate using appropriate excipients such as sucrose.

The pharmaceutical compositions of the invention can be selected for parenteral delivery. Alternatively, the compositions may be selected for inhalation or for delivery through the digestive tract, such as orally. Preparation of such pharmaceutically acceptable compositions is within the skill of the art. The formulation components are present preferably in concentrations that are acceptable to the site of administration. In certain embodiments, buffers are used to maintain the composition at physiological pH or at a slightly lower pH, typically within a pH range of from about 5 to about 8.

When parenteral administration is contemplated, the therapeutic compositions for use in this invention may be provided in the form of a pyrogen-free, parenterally acceptable aqueous solution comprising the desired antibody or Fc-fusion protein in a pharmaceutically acceptable vehicle. A particularly suitable vehicle for parenteral injection is sterile distilled water in which the antibody or Fc-fusion protein is formulated as a sterile, isotonic solution, properly preserved. In certain embodiments, the preparation involves the formulation of the desired molecule with an agent, such as injectable microspheres, bio-erodible particles, polymeric compounds (such as polylactic acid or polyglycolic acid), beads or liposomes, that may provide controlled or sustained release of the product which can be delivered via depot injection. In certain embodiments, hyaluronic acid may also be used, having the effect of promoting sustained duration in the circulation. In certain embodiments, implantable drug delivery devices may be used to introduce the desired antibody or Fc-fusion protein.

Pharmaceutical compositions of the invention can be formulated for inhalation. In these embodiments, antibody or Fc-fusion protein is advantageously formulated as a dry, inhalable powder. In specific embodiments, antibody or Fc-fusion protein inhalation solutions may also be formulated with a propellant for aerosol delivery. In certain embodiments, solutions may be nebulized. Pulmonary administration and formulation methods therefore are further described in International Patent Application No. PCT/US94/001875, which is incorporated by reference and describes pulmonary delivery of chemically modified proteins.

It is also contemplated that formulations can be administered orally. antibody or Fc-fusion protein that are administered in this fashion can be formulated with or without carriers customarily used in the compounding of solid dosage forms such as tablets and capsules. In certain embodiments, a capsule may be designed to release the active portion of the formulation at the point in the gastrointestinal tract when bioavailability is maximized and pre-systemic degradation is minimized. Additional agents can be included to facilitate absorption of the antibody or Fc-fusion protein. Diluents, flavorings, low melting point waxes, vegetable oils, lubricants, suspending agents, tablet disintegrating agents, and binders may also be employed.

Additional pharmaceutical compositions will be evident to those skilled in the art, including formulations involving antibody or Fc-fusion protein in sustained- or controlled-delivery formulations. Techniques for formulating a variety of other sustained- or controlled-delivery means, such as liposome carriers, bio-erodible microparticles or porous beads and depot injections, are also known to those skilled in the art. See, for example, International Patent Application No. PCT/US93/00829, which is incorporated by reference and describes controlled release of porous polymeric microparticles for delivery of pharmaceutical compositions. Sustained-release preparations may include semipermeable polymer matrices in the form of shaped articles, e.g., films, or microcapsules. Sustained release matrices may include polyesters, hydrogels, polylactides (as disclosed in U.S. Pat. No. 3,773,919 and European Patent Application Publication No. EP058481, each of which is incorporated by reference), copolymers of L-glutamic acid and gamma ethyl-L-glutamate (Sidman et al., 1983, Biopolymers 2:547-556), poly (2-hydroxyethyl-methacrylate) (Langer et al., 1981, J. Biomed. Mater. Res. 15:167-277 and Langer, 1982, Chem. Tech. 12:98-105), ethylene vinyl acetate (Langer et al., 1981, supra) or poly-D(-)-3-hydroxybutyric acid (European Patent Application Publication No. EP133988). Sustained release compositions may also include liposomes that can be prepared by any of several methods known in the art. See, e.g., Eppstein et al., 1985, Proc. Natl. Acad. Sci. U.S.A. 82:3688-3692; European Patent Application Publication Nos. EP036676; EP088046 and EP143949, incorporated by reference.

Pharmaceutical compositions used for in vivo administration are typically provided as sterile preparations. Sterilization can be accomplished by filtration through sterile filtration membranes. When the composition is lyophilized, sterilization using this method may be conducted either prior to or following lyophilization and reconstitution. Compositions for parenteral administration can be stored in lyophilized form or in a solution. Parenteral compositions generally are placed into a container having a sterile access port, for example, an intravenous solution bag or vial having a stopper pierceable by a hypodermic injection needle.

Aspects of the invention includes self-buffering heterodimeric antibody or fragment formulations, which can be used as pharmaceutical compositions, as described in international patent application WO 2006/138181A2 (PCT/US2006/022599), which is incorporated by reference in its entirety herein.

As discussed above, certain embodiments provide antibody or Fc-fusion protein compositions, particularly pharmaceutical antibody or Fc-fusion protein compositions, that comprise, in addition to the antibody or Fc-fusion protein, one or more excipients such as those illustratively described in this section and elsewhere herein. Excipients can be used in the invention in this regard for a wide variety of purposes, such as adjusting physical, chemical, or biological properties of formulations, such as adjustment of viscosity, and or processes of the invention to improve effectiveness and or to stabilize such formulations and processes against degradation and spoilage due to, for instance, stresses that occur during manufacturing, shipping, storage, pre-use preparation, administration, and thereafter.

A variety of expositions are available on protein stabilization and formulation materials and methods useful in this regard, such as Arakawa et al., "Solvent interactions in pharmaceutical formulations," Pharm Res. 8(3): 285-91 (1991); Kendrick et al., "Physical stabilization of proteins in aqueous solution," in: RATIONAL DESIGN OF STABLE PROTEIN FORMULATIONS: THEORY AND PRACTICE, Carpenter and Manning, eds. Pharmaceutical Bio-technology. 13: 61-84 (2002), and Randolph et al., "Surfac-tant-protein interactions," Pharm. Biotechnol. 13: 159-75 (2002), each of which is herein incorporated by reference in its entirety, particularly in parts pertinent to excipients and processes of the same for self-buffering protein formulations in accordance with the current invention, especially as to protein pharmaceutical products and processes for veteri-nary and/or human medical uses.

Salts may be used in accordance with certain embodi-ments of the invention to, for example, adjust the ionic strength and/or the isotonicity of a formulation and/or to improve the solubility and/or physical stability of a protein or other ingredient of a composition in accordance with the invention.

As is well known, ions can stabilize the native state of proteins by binding to charged residues on the protein's surface and by shielding charged and polar groups in the protein and reducing the strength of their electrostatic inter-actions, attractive, and repulsive interactions. Ions also can stabilize the denatured state of a protein by binding to, in particular, the denatured peptide linkages (—CONH) of the protein. Furthermore, ionic interaction with charged and polar groups in a protein also can reduce intermolecular electrostatic interactions and, thereby, prevent or reduce protein aggregation and insolubility.

Ionic species differ significantly in their effects on pro-teins. A number of categorical rankings of ions and their effects on proteins have been developed that can be used in formulating pharmaceutical compositions in accordance with the invention. One example is the Hofmeister series, which ranks ionic and polar non-ionic solutes by their effect on the conformational stability of proteins in solution. Stabilizing solutes are referred to as "kosmotropic." Desta-bilizing solutes are referred to as "chaotropic." Kosmotropes commonly are used at high concentrations (e.g., >1 molar ammonium sulfate) to precipitate proteins from solution ("salting-out"). Chaotropes commonly are used to denture and/or to solubilize proteins ("salting-in"). The relative effectiveness of ions to "salt-in" and "salt-out" defines their position in the Hofmeister series.

Free amino acids can be used in antibody or Fc-fusion protein formulations in accordance with various embodi-ments of the invention as bulking agents, stabilizers, and antioxidants, as well as other standard uses. Lysine, proline, serine, and alanine can be used for stabilizing proteins in a formulation. Glycine is useful in lyophilization to ensure correct cake structure and properties. Arginine may be useful to inhibit protein aggregation, in both liquid and lyophilized formulations. Methionine is useful as an antioxidant.

Polyols include sugars, e.g., mannitol, sucrose, and sor-bitol and polyhydric alcohols such as, for instance, glycerol and propylene glycol, and, for purposes of discussion herein, polyethylene glycol (PEG) and related substances. Polyols are kosmotropic. They are useful stabilizing agents in both liquid and lyophilized formulations to protect proteins from physical and chemical degradation processes. Polyols also are useful for adjusting the tonicity of formulations.

Among polyols useful in select embodiments of the invention is mannitol, commonly used to ensure structural stability of the cake in lyophilized formulations. It ensures structural stability to the cake. It is generally used with a lyoprotectant, e.g., sucrose. Sorbitol and sucrose are among preferred agents for adjusting tonicity and as stabilizers to protect against freeze-thaw stresses during transport or the preparation of bulks during the manufacturing process. Reducing sugars (which contain free aldehyde or ketone groups), such as glucose and lactose, can glycate surface lysine and arginine residues. Therefore, they generally are not among preferred polyols for use in accordance with the invention. In addition, sugars that form such reactive spe-cies, such as sucrose, which is hydrolyzed to fructose and glucose under acidic conditions, and consequently engen-ders glycation, also is not among preferred polyols of the invention in this regard. PEG is useful to stabilize proteins and as a cryoprotectant and can be used in the invention in this regard.

Embodiments of the antibody or Fc-fusion protein for-mulations further comprise surfactants. Protein molecules may be susceptible to adsorption on surfaces and to dena-turation and consequent aggregation at air-liquid, solid-liquid, and liquid-liquid interfaces. These effects generally scale inversely with protein concentration. These deleterious interactions generally scale inversely with protein concen-tration and typically are exacerbated by physical agitation, such as that generated during the shipping and handling of a product.

Surfactants routinely are used to prevent, minimize, or reduce surface adsorption. Useful surfactants in the inven-tion in this regard include polysorbate 20, polysorbate 80, other fatty acid esters of sorbitan polyethoxylates, and poloxamer 188.

Surfactants also are commonly used to control protein conformational stability. The use of surfactants in this regard is protein-specific since, any given surfactant typically will stabilize some proteins and destabilize others.

Polysorbates are susceptible to oxidative degradation and often, as supplied, contain sufficient quantities of peroxides to cause oxidation of protein residue side-chains, especially methionine. Consequently, polysorbates should be used carefully, and when used, should be employed at their lowest effective concentration. In this regard, polysorbates exem-plify the general rule that excipients should be used in their lowest effective concentrations.

Embodiments of antibody or Fc-fusion protein formula-tions further comprise one or more antioxidants. To some extent deleterious oxidation of proteins can be prevented in pharmaceutical formulations by maintaining proper levels of ambient oxygen and temperature and by avoiding exposure to light. Antioxidant excipients can be used as well to prevent oxidative degradation of proteins. Among useful antioxidants in this regard are reducing agents, oxygen/free-radical scavengers, and chelating agents. Antioxidants for use in therapeutic protein formulations in accordance with the invention preferably are water-soluble and maintain their activity throughout the shelf life of a product. EDTA is a preferred antioxidant in accordance with the invention in this regard.

Formulations in accordance with the invention may include metal ions that are protein co-factors and that are necessary to form protein coordination complexes, such as zinc necessary to form certain insulin suspensions. Metal ions also can inhibit some processes that degrade proteins. However, metal ions also catalyze physical and chemical processes that degrade proteins.

Magnesium ions (10-120 mM) can be used to inhibit isomerization of aspartic acid to isoaspartic acid. $Ca^{+2}$ ions (up to 100 mM) can increase the stability of human deoxy-ribonuclease. $Mg^{+2}$, $Mn^{+2}$, and $Zn^{+2}$, however, can destabi-lize rhDNase. Similarly, $Ca^{+2}$ and $Sr^{+2}$ can stabilize Factor VIII, it can be destabilized by $Mg^{+2}$, $Mn^{+2}$ and $Zn^{+2}$, $Cu^{+2}$ and $Fe^{+2}$, and its aggregation can be increased by Al+3 ions.

Embodiments of the antibody or Fc-fusion protein for-mulations further comprise one or more preservatives. Pre-servatives are necessary when developing multi-dose parenteral formulations that involve more than one extraction from the same container. Their primary function is to inhibit microbial growth and ensure product sterility throughout the shelf-life or term of use of the drug product. Commonly used preservatives include benzyl alcohol, phenol and m-cresol. Although preservatives have a long history of use with small-molecule parenterals, the development of protein formulations that includes preservatives can be challenging. Preservatives almost always have a destabilizing effect (aggregation) on proteins, and this has become a major factor in limiting their use in multi-dose protein formulations. To date, most protein drugs have been formulated for single-use only. However, when multi-dose formulations are possible, they have the added advantage of enabling patient convenience, and increased marketability. A good example is that of human growth hormone (hGH) where the development of preserved formulations has led to commercialization of more convenient, multi-use injection pen presentations. At least four such pen devices containing preserved formulations of hGH are currently available on the market. Norditropin (liquid, Novo Nordisk), Nutropin AQ (liquid, Genentech) & Genotropin (lyophilized—dual chamber cartridge, Pharmacia & Upjohn) contain phenol while Somatrope (Eli Lilly) is formulated with m-cresol.

Several aspects need to be considered during the formulation and development of preserved dosage forms. The effective preservative concentration in the drug product must be optimized. This requires testing a given preservative in the dosage form with concentration ranges that confer anti-microbial effectiveness without compromising protein stability.

As might be expected, development of liquid formulations containing preservatives are more challenging than lyophilized formulations. Freeze-dried products can be lyophilized without the preservative and reconstituted with a preservative containing diluent at the time of use. This shortens the time for which a preservative is in contact with the protein, significantly minimizing the associated stability risks. With liquid formulations, preservative effectiveness and stability should be maintained over the entire product shelf-life (about 18 to 24 months). An important point to note is that preservative effectiveness should be demonstrated in the final formulation containing the active drug and all excipient components.

Antibody or Fc-fusion protein formulations generally will be designed for specific routes and methods of administration, for specific administration dosages and frequencies of administration, for specific treatments of specific diseases, with ranges of bio-availability and persistence, among other things. Formulations thus may be designed in accordance with the invention for delivery by any suitable route, including but not limited to orally, aurally, ophthalmically, rectally, and vaginally, and by parenteral routes, including intravenous and intraarterial injection, intramuscular injection, and subcutaneous injection.

Once the pharmaceutical composition has been formulated, it may be stored in sterile vials as a solution, suspension, gel, emulsion, solid, crystal, or as a dehydrated or lyophilized powder. Such formulations may be stored either in a ready-to-use form or in a form (e.g., lyophilized) that is reconstituted prior to administration. The invention also provides kits for producing a single-dose administration unit. The kits of the invention may each contain both a first container having a dried protein and a second container having an aqueous formulation. In certain embodiments of this invention, kits containing single and multi-chambered pre-filled syringes (e.g., liquid syringes and lyosyringes) are provided.

The therapeutically effective amount of an antibody or Fc-fusion protein pharmaceutical composition to be employed will depend, for example, upon the therapeutic context and objectives. One skilled in the art will appreciate that the appropriate dosage levels for treatment will vary depending, in part, upon the molecule delivered, the indication(s) for which the antigen binding protein is being used, the route of administration, and the size (body weight, body surface or organ size) and/or condition (the age and general health) of the patient. In certain embodiments, the clinicians may titer the dosage and modify the route of administration to obtain the optimal therapeutic effect.

Kits

A pharmaceutical composition comprising one or more antibody or Fc-fusion protein described herein may be placed within containers (e.g., vials or syringes), along with packaging material that provides instructions regarding the use of such pharmaceutical compositions. Generally, such instructions will include a tangible expression describing antibody or Fc-fusion protein concentration, as well as within certain embodiments, relative amounts of excipient ingredients or diluents (e.g., water, saline or PBS) that may be necessary to reconstitute the pharmaceutical composition.

EXAMPLES

The following examples, including the experiments conducted and results achieved, are provided for illustrative purposes only and are not to be construed as limiting upon the teachings herein.

Example 1

The following Example describes production and glycosylation analysis of Fc-variant antibodies.

DNA constructs. Site-directed mutagenesis of the CH2 domain was performed with a Site-Directed Mutagenesis kit as per the manufacturer's instructions (Agilent). The following oligonucleotides were used for mutagenesis: 5'-cctgtggcaggaccggacgtcttcctcttcccc-3' (SEQ ID NO: 37; S239D); 5'-cacctgtggcaggaccgcaggtcttcctcttccc-3' (SEQ ID NO: 38; S239E); 5'-cacctgtggcaggaccgcaggtcttcctcttccc-3' (SEQ ID NO: 39; S239K); 5'-cacgtgcgtggtggacgacgtgagc-cacgaag-3' (SEQ ID NO: 40; V264D); 5'-cacgtgcgtggtgctggacgtgagccac-3' (SEQ ID NO: 41; V264L); 5'-cgtgcgtggtggtggcagtgagccacgaagac-3' (SEQ ID NO: 42; D265A); 5'-cacgtgcgtggtggtgctcgtgagccacgaagac-3' (SEQ ID NO: 43; D265L); 5'-cacgtgcgtggtggtgtccgtgagc-cacgaagac-3' (SEQ ID NO: 44; D265S); 5'-gaa-gaccccgaggtccaggctaactggtacgtggacgg-3' (SEQ ID NO: 45; F296A); 5'-gaggtcacgtgcgtggtggacgctgtgagccacgaagaccc-3' (SEQ ID NO: 46; V264D/D265A); All constructs described above were verified by DNA sequencing.

Cell culture, transfection, amplification and production. Chinese Hamster Ovary (CHO) cell lines were maintained in serum-free medium. Stable CHO cell 0 nM pools were obtained by transfecting CHO host cell line followed by selection in -GHT medium. 0 nM pools were further amplified in 150 nM MTX-containing medium to generate 150 nM stable pools. mAb from different stable pools were generated from fed-batch production assays in 125-mL shake flasks in chemically-defined production medium. Glucose levels were checked on the feed days and were maintained at 10-12 g/L using 50% glucose stock solution (HyClone). All of the production cultures were harvested on day 10.

MAb purification and quantification. The secreted mAb concentration was purified and quantified using a high throughput protein A assay. Antibody titer was measured via Protein A affinity column. Samples containing Antibody were injected and run over a column packed with immobilized Protein A. Bound antibody was then eluted under acidic conditions, integrated, and finally quantified via a standard curve.

MAb product quality analysis. Antibody aggregate were measured by SEC. Samples were run on HPLC and separated by hydrodynamic size utilizing a SEC column. Chromatograms were analyzed for aggregate and monomer. N-Glycans were analyzed by 2-AA HILIC glycan analysis. Briefly, antibody N-glycans were released with PNGase F, labeled with 2-aminobenzoic acid, and separated via HILIC chromatography. Chromatograms were analyzed for species percentages.

Differential Scanning Calorimetry (DSC). The DSC measurements were obtained using a VP-Capillary DSC system (Microcal Inc., Northampton, MA) equipped with tantalum 61 cells, each with an active volume of 135 μL. Protein samples were diluted to 0.5 mg/mL in a buffer containing 100 mM acetate, pH 5.0, while the corresponding buffer was used as a reference. The samples were scanned from 20° C. to 100° C. at a rate of 60° C./hour with an initial 15 min of equilibration at 20° C. A filtering period of 16 s was used and data was analyzed using Origin 7.0 software (OriginLab® Corporation, Northampton, MA). Thermograms were corrected by subtraction of buffer-only blank scans. The corrected thermograms were normalized for protein concentration. The melting temperature, $T_m$, was determined using the DSC functions built into Origin 7.0 software.

Results

Figure 2:
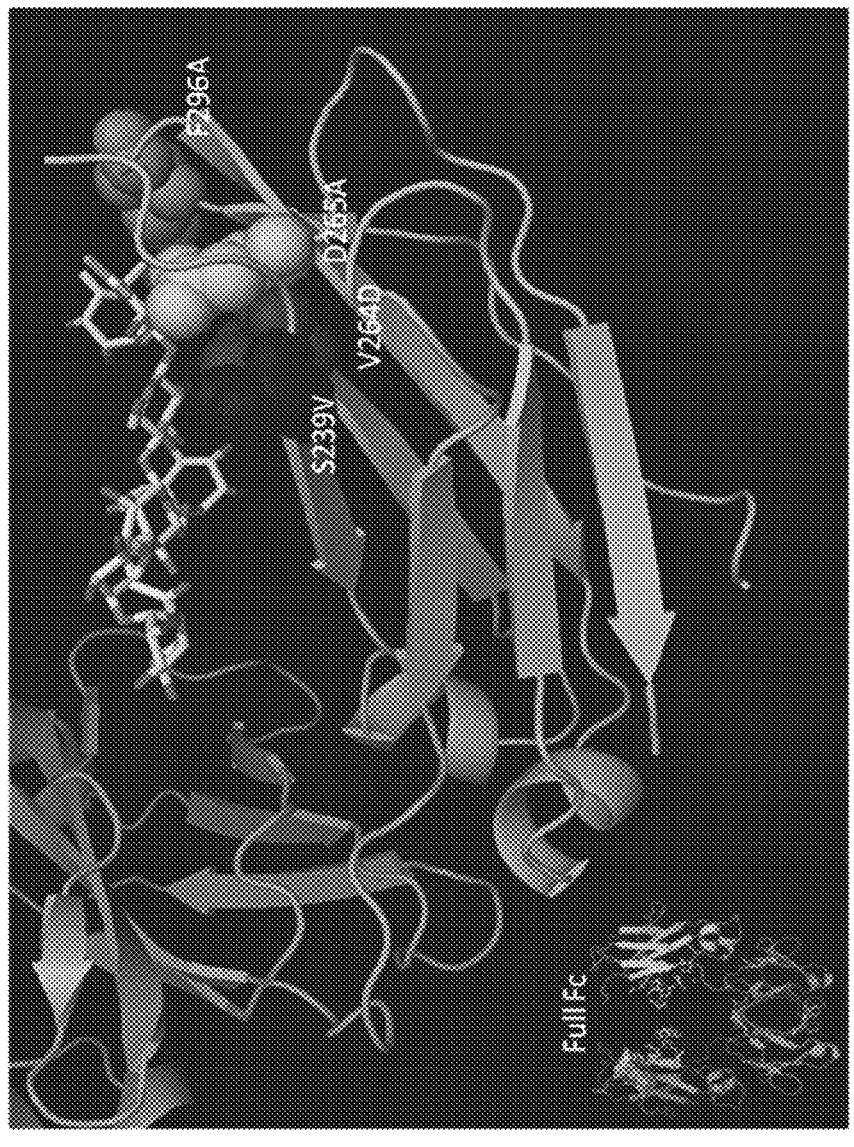
FIG. 2 The residues on IgG2 Fc domain that have potential impacts on glycosylation of mAb. Crystal structure of IgG2 with labeled oligosaccharide and residues that have potential impact on glycan processing in vivo.

Immature glycan species, such as HM and G0, are the main cause of heterogeneity. Therefore, improving glycosylation maturation will decrease glycan heterogeneity of mAb. Different from other glyco-protein, the oligosaccharide chain is attached through asparagine residue 297 that is buried inside the internal space of "horseshoe" shape of the IgG-Fc. Thus one could hypothesize that the Fc structure or the surrounding protein residues will affect the accessibility of glycan processing machinery, such as enzymes or substrates, and eventually impact the process efficiency. Based on this hypothesis, we used a human IgG2 crystal structure to select 4 amino acid residues in the CH2 domain that are spatially proximal to the consensus N-glycosylation site and also the oligosaccharide chains. The crystal structure of IgG2 suggested that S239, V264, D265, and F296 might be critically involved in either stabilizing the core N-acetylglucosamine or changing the accessibility of glycosylation enzymes (FIG. 2). The nucleotide sequence corresponding to these amino acid residues were mutated as summarized in Table 2 to test whether this strategy would alter glycan processing.

TABLE 2

| AA | Mutations to improve glycan processing |
|---|---|
| S239 | D, E, K |
| V264 | D, L, A, S |
| D265 | A |
| F296 | A |

Generation of Fc-Variant mAbs with Different Glycan Processing Efficiencies

The mAb constructs were transfected into CHO cells and stable pools expressing the Fc-mutant mAbs were generated using Amgen platform procedures. The Fc-variant mAbs were generated using Amgen platform fed-batch production method, and the mAb glycosylation was analyzed by the glycan mapping (Materials and Methods).

Figure 3:
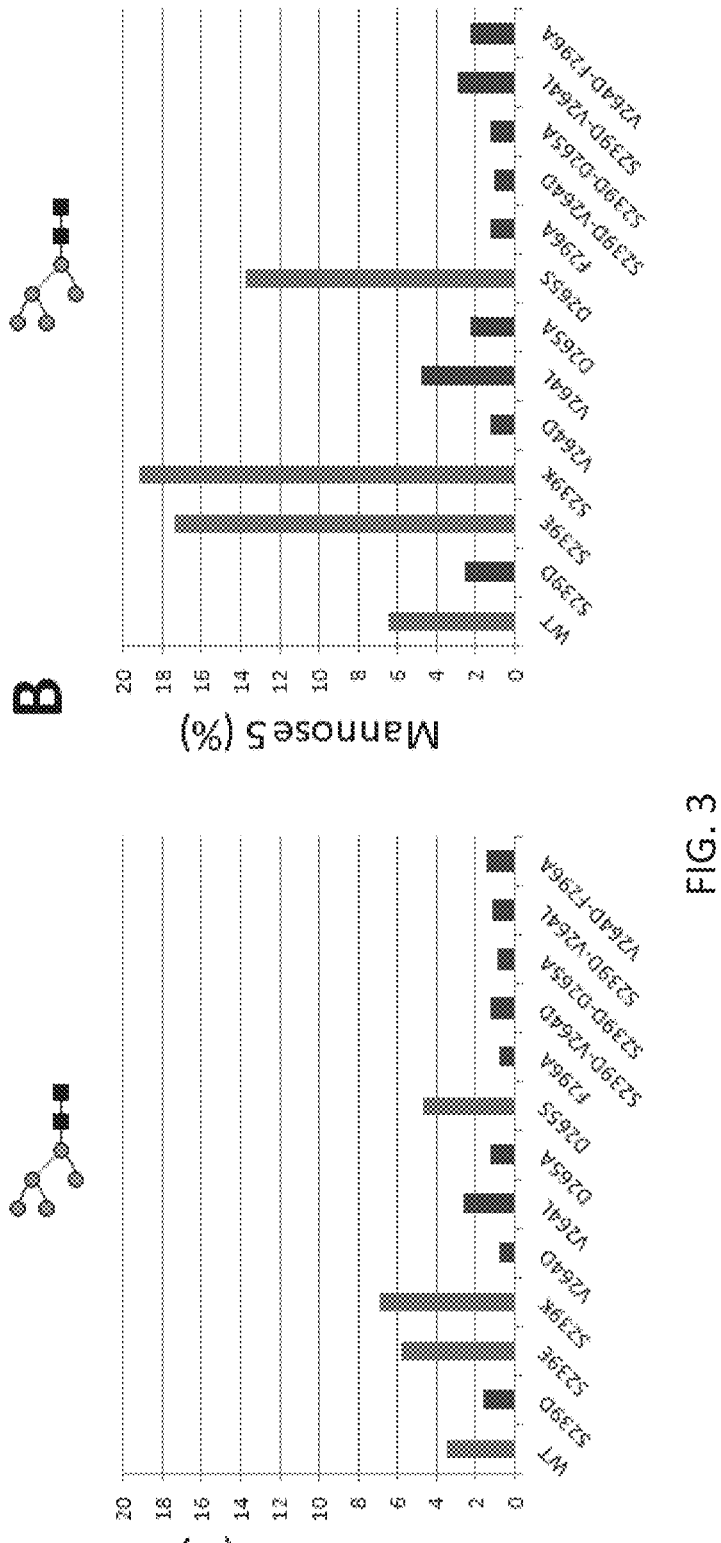
FIG. 3 Amino acid mutations in Fc region decrease % Mannose 5. Fc-variant mAbs were generated by 10-day fed-batch production culture. Glycan mapping results of three independent transfection pools are shown. Data shown represent the average of triplicate values with standard deviations. (A) unamplified; (B) 150 nM MTX-amplified.

As shown in FIG. 3, the Mannose 5 (M5) level of wildtype mAb is 3.5% in unamplified (0 nM) cells (A) but increases to 6.4% in 150 nM amplified cells (B), which is a common observation for all mAb-production cells since glycan processing is highly vulnerable to changes in culture/expression systems. On the other hand, single AA mutations S239D, V264D/L, D265A and F296A and double mutations of S239D/V264D, S239D/D265A, S239D/V264L, and V264D/F296A are sufficient to decrease M5 levels up to 84% compared to that of the wild type Fc, indicating that glycan processing is more efficient in these mutants (FIG. 3). Importantly, high mannose processing from V264D, D265A, F296A, and the double mutations S239D/V264D, S239D/D265A, appeared to not be affected by the differences in culture/expression systems. The levels of % M5 from these variants remain the same with (B) or without 150 nM (A) MTX amplification.

Figure 4:
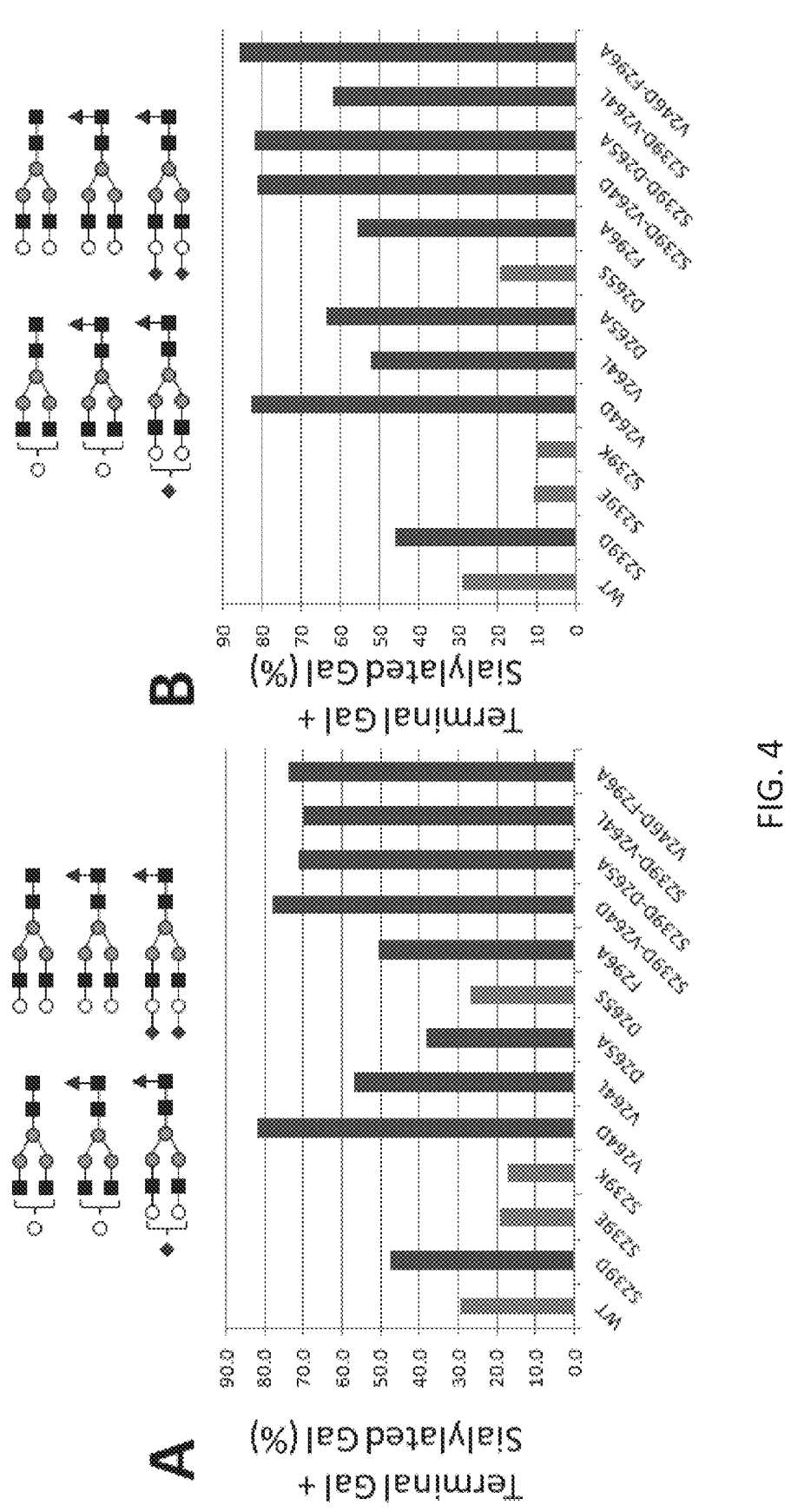
FIG. 4 Amino acid mutations that increase glycosylation maturation. Fc-variant mAbs were generated by 10-day fed-batch production culture. Glycan mapping results of three independent transfection pools are shown. Data shown represent the average of triplicate values with standard deviations. (A) unamplified; (B) 150 nM MTX-amplified FIG. 5 Amino acid mutations that decrease immature glyco-forms. Fc-variant mAbs were generated by 10-day fed-batch production culture. Glycan mapping results of three independent transfection pools are shown. Data shown represent the average of triplicate values with standard deviations. (A) unamplified; (B) 150 nM MTX-amplified FIG. 6 Differential Scanning Calorimetry of Fc-variant mAbs.
Figure 5:
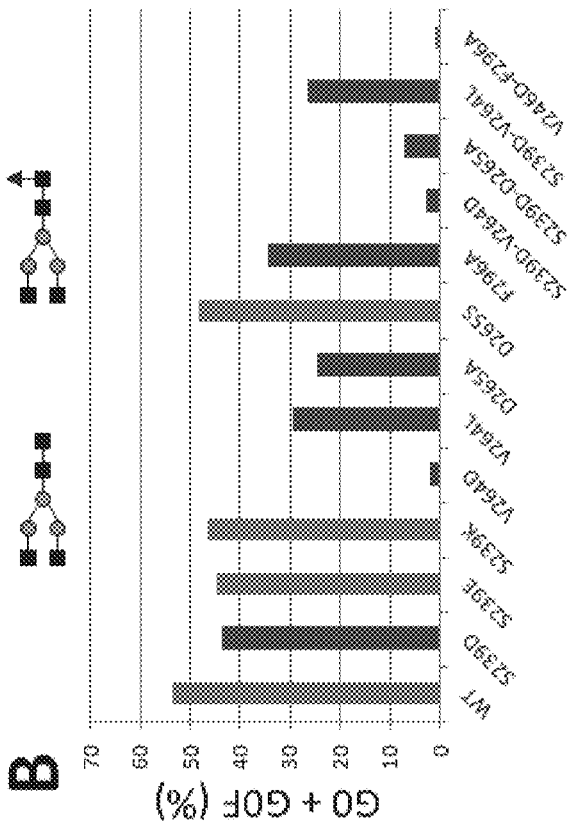
Figure 5:
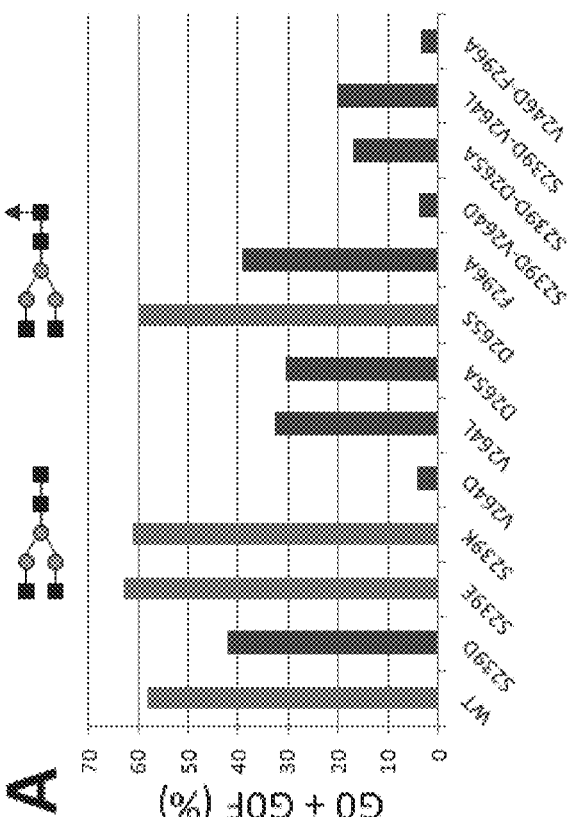
Figure 6:
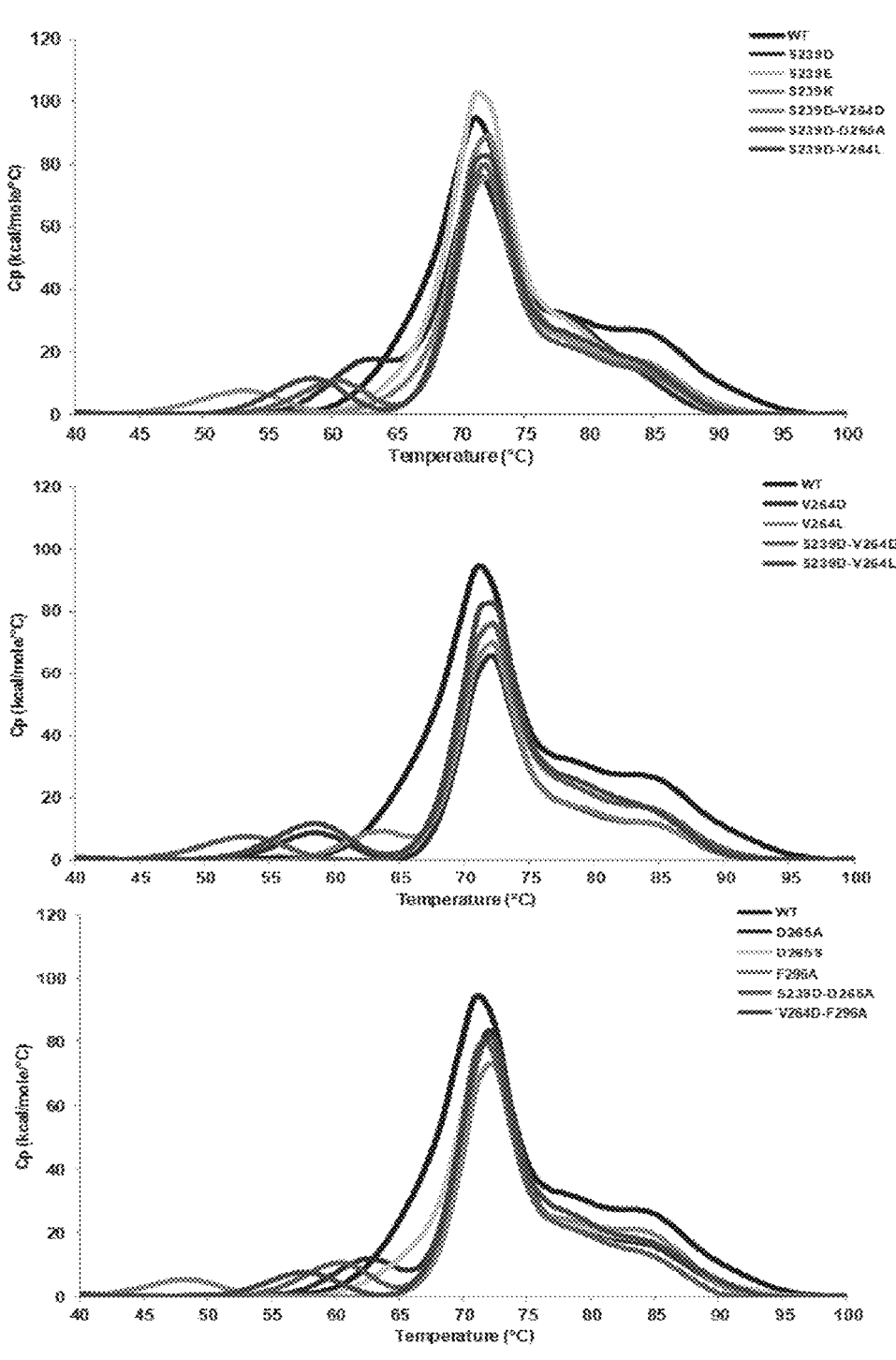

To further evaluate whether these Fc-variants can improve glycosylation maturation, terminal sugars, such as galactose, fucose and sialic acid, were examined. As shown in FIG. 4, there are up to 2.5 fold increases in galactosylated mAb containing 1, or 2 Gal residues with or without sialylation (FIG. 4). Same trends were found consistently in both 0 nM (A) and 150 nM pools (B). In the meantime, immature glyco-forms, G0 and G0F, decreased significantly in the corresponding mutants (FIG. 5). These data suggested CHO-derived mAb that exhibited certain CH2 Fc mutations can be fully matured during glycosylation in CHO cells. It was noted that incorporation of these mutants into the antibody reduced the production of immature glycoforms levels, i.e. high mannose, G0 and G0F, to sufficiently low levels (<5% overall) consistently that are not affected by different culture/expression systems (FIGS. 2 and 4, V264D, S239D/V264D, and V264D/F296A). Therefore, the requirement/need for further product quality control by process development becomes is reduced. In addition there is no cell engineering or process technology tools described/available to date that allow for the increase galactosylation to levels observed in these mutants and immature glycoforms to less than 5%. In comparison, other AA mutants that were tested, such as S239E, S239K, and D265S, had an opposite impact on glycan processing (FIG. 3 through 6) demonstrating that the impact of the mutations is specific by design.

Fc-Variant mAbs Manifest Expected Folding

The folding of mAb variants was verified by DSC. Both wild type and the mutant proteins exhibit typical thermal unfolding profiles of an IgG molecule. The results (FIG. 6) indicate that these Fc-variants are viable product candidates that successfully maintain conformational integrity. Several mutations impacted the first $T_m$, reflecting the mid-point of CH2 domain melting. However, the majority of the mutations did not affect the onset temperature of the CH2 melting. These findings are consistent with the hypothesis that the mutations may alter the local conformation near the glycosylation site and, thereby, influence the maturation of glycan modifications. Though, in general, the thermal stability of these mutations may not present additional challenges to the product manufacturing, storage, distribution and administration, the DSC results may further guide the mutagenesis strategy to select the most desired Fc-variants.

Example 2

The following example describes additional mutations and further characterization of the Fc-variant antibodies.
Selection of the Positions for N-Glycosylation Engineering.

Crystal structure of Fc domain of human IgG2, which is the high resolution structure of entire human antibody. Glycosylation location was visualized using the Molecular Operating Environment (MOE) from the Chemical Computing Group ("Molecular Operating Environment (MOE); Chemical Computing Group Inc., 1010 Sherbooke St. West, Suite #910, Montreal, QC, Canada, H3A 2R7, 2011," n.d.). The structure used for atomic visualization was 1HZH (Saphire et al., 2001). While both antibody heavy chains were utilized in the structure analysis, chain H was used primarily for the visualizations. Residue positions and their interactions with the sugars were performed by a variety of methods including direct atomic distance measurements and per residue solvent exposure difference calculations with and without the presence of sugars.
DNA Constructs, Cell Culture, Transfection, Amplification and Production.

Site-directed mutagenesis of the CH2 domain was performed with a Site-Directed Mutagenesis kit as per the manufacturer's instructions (Agilent). All constructs were verified by DNA sequencing.

Chinese Hamster Ovary (CHO) cell lines were maintained in serum-free medium. Stable CHO cell 0 nM pools were obtained by transfecting CHO host cell line followed by selection in -GHT medium. 0 nM pools were further amplified in 150 nM MTX-containing medium to generate 150 nM stable pools. mAb from different stable pools were generated from fed-batch production assays in 125-mL shake flasks in chemically-defined production medium. Glucose levels were checked on the feed days and were maintained at 10-12 g/L using 50% glucose stock solution (HyClone). All of the production cultures were harvested on day 10.
MAb Purification and Quantification.

The secreted mAb concentration was purified and quantified using a high throughput protein A assay. HMW and glycosylation were analyzed by in-house SEC and HILIC assay. Antibody titer was measured via a Protein A affinity column. Samples containing antibody were injected and run over a column packed with immobilized Protein A. Bound antibody was then eluted under acidic conditions, integrated, and finally quantified via a standard curve.
MAb Product Quality Analysis.

Antibody aggregate were measured by Size Exclusion Chromatography (SEC). Samples were run on HPLC and separated by hydrodynamic size utilizing a SEC column. Chromatograms were analyzed for aggregate and monomer. N-Glycans were analyzed by 2-AA HILIC glycan analysis. Briefly, antibody N-glycans were released with PNGase F, labeled with 2-aminobenzoic acid, and separated via HILIC chromatography. Chromatograms were analyzed for species percentages.
Hydrophilic Interaction Chromatography (HILIC-MS)-Glycan Mapping Method.

An aliquot of 120 µg of mAb was treated with 3 µL of PNGase F in a 1× digestion buffer (1×PBS buffer). The final volume was 30 µL and the final pH should be about 7.4 with 1×PBS buffer salt concentration. The mixture was incubated at 37° C. for 2 hours. To the release glycan mixture, a 2-aminobenzoic acid (2-AA) fluorescent labeling solution (12 mg/ml 2-aminobenzoic acid with 0.04 M sodium cyanoborohydride) was added and heated at 80° C. The excess 2-AA reagent was removed according to Prozyme protocol to obtain dried glycans. The 2-AA labeled glycan in 15 µL Milli-Q water solution was loaded and separated in UPLC. The temperature for the HILIC column during the separation was 50° C. The injection volume of the labeled glycan was 3 µL. Mobile phase A was 100 mM ammonium formate, pH 3.0 and mobile phase B was 100% acetonitrile. The separation used a flow rate of 0.4 mL/minute and a gradient of 22% to 45% A in 40 minutes, followed by clean up and re-equilibration of the column resulting in total run time of 45 minutes. The migrated glycan species were monitored with a fluorescence detector at excitation of 360 nm and emission of 425 nm. The quantified glycan contents are integrated from fluorescent peaks in the HILIC glycan map while the assignments of these glycan peaks are confirmed by mass spectrometry (MS).
Differential Scanning Calorimetry (DSC).

The DSC measurements were obtained using a VP-Capillary DSC system (Microcal Inc., Northampton, MA) equipped with tantalum 61 cells, each with an active volume of 135 µL. Protein samples were diluted to 0.5 mg/mL in a buffer containing 100 mM acetate, pH 5.0, while the corresponding buffer was used as a reference. The samples were scanned from 20° C. to 100° C. at a rate of 60° C./hour with an initial 15 min of equilibration at 20° C. A filtering period of 16 s was used and data was analyzed using Origin 7.0 software (OriginLab® Corporation, Northampton, MA). Thermograms were corrected by subtraction of buffer-only blank scans. The corrected thermograms were normalized for protein concentration. The melting temperature, $T_m$, was determined using the DSC functions built into Origin 7.0 software.
Measurement of Relative FcγRIIA Binding of Fc Mutants.

Relative potencies of binding were determined using AlphaLISA technology (Perkin Elmer, Waltham, MA). GST-tagged FcγRIIA was provided by Amgen, Inc. AlphaLISA Glutathione Acceptor Beads (Perkin Elmer City, State) were coated with 5 nM FcγRIIA in 1× Immunoassay Buffer (Perkin Elmer, Waltham, MA) for 2-4 hours at ambient temperature. Mutant Fc species were combined with 1 nM biotinylated antibody competitor molecule and incubated 22-26 hours at ambient temperature with 10 ug/mL FcγRIIA-coated acceptor beads. 10 ug/mL AlphaLISA Streptavidin Donor Beads (Perkin Elmer, Waltham, MA) were added and the reactions were incubated 22-26 hours at ambient temperature. AlphaSignal was collected as relative luminescence units using the Envision plate reader (Perkin Elmer, Waltham, MA). Binding of tested antibodies to FcγRIIA disrupts the interaction of the biotinylated competitor molecule and FcγRIIA, thereby preventing the donor and acceptor beads from coming into proximity, resulting in a decrease in emission at 520-620 nM. Relative potencies of binding were calculated as compared to wild type Fc in Softmax Pro v 5.4.1 (Molecular Devices, Sunnyvale, CA).
FcRn AlphaScreen-Based Binding Assay.

The FcRn (neonatal Fc receptor) binding assay utilized in this study was a competitive inhibition assay performed under mildly acidic conditions (~pH 6) to characterize FcRn binding of the test molecule. It utilized the AlphaScreen® technology (Perkin Elmer, Waltham, MA) which is a bead-based Amplified Luminescent Proximity Homogenous Assay (Alpha) format that detects bimolecular interactions. This technology required two bead types, viz. acceptor beads and donor beads. The acceptor beads were coated with a hydrogel that contained thioxene derivatives, as well as nickel chelate (Ni Chelate). The donor beads were coated with a hydrogel that contained phthalocyanine, a photosensitizer, and streptavidin. In the assay, the test molecule competed with a fixed concentration of biotinylated Fc (Fc-biotin), for binding to a soluble form of recombinant human FcRn labeled with histidine (FcRn-his). After FcRn-his bound to Fc-biotin in solution phase, two bead types were added to the reaction mixture. In this reaction, the acceptor beads got bound to the histidine tag of FcRn-his via Ni Chelate, and the donor beads got bound to the Fc-biotin via streptavidin. By virtue of these linkages, a bridge was formed between the two bead types that brought them into close proximity. When a laser was applied to this complex, the ambient oxygen was converted to the singlet oxygen by the donor beads. With the beads in close proximity, an energy transfer to the acceptor bead occurred resulting in a luminescence response. In the assay, the test molecules caused a dose dependent decrease in the luminescence response, which was measured by Envision® plate reader (Perkin Elmer, Waltham, MA). The activity levels of the mutant samples were determined by comparing their dose response curves to the response curve of the wild type and were reported as percent relative binding (% relative binding). Each sample (mutant) was tested in three independent assays and the % relative binding values were averaged across those three determinations.

Pharmacokinetics (PK) Study in Mice

Pharmacokinetic studies were performed in male CD-1 mice (6-8 week old). Three mice per group received a single dose of mAb variants via intravenous administration. The dose was 0.25 mg/kg was based on the most recent scheduled body weights. The test articles were diluted to 0.125 mg/mL resulting in approximate dose volume of 2 ml/kg. Samples for PK analysis were taken at 0, 0.5, 2, 4, 8, 24, 48, 72, 168, 240, 336, 504 and 672 hrs post dose. Blood samples were collected via retro-orbital sinus puncture (0.07 mL) in Microtainer® Brand Serum Separator Tubes. Quantitation of mAb variants was performed using a sandwich immunoassay format with a biotinylated murine anti-human IgG Fc specific mAb as a capture and a Alexafluor 647 murine anti-human Fc mAb using GyrosLab™ automated immunoassay (Hall 2013; Journal of Immunological Methods 393 (2013) 70-73). The lower limit of quantitation (LLOQ) in the assay was 50 ng/mL. Bioanalytical data analyses were performed Phoenix WinNonlin.

Results

Figure 8:
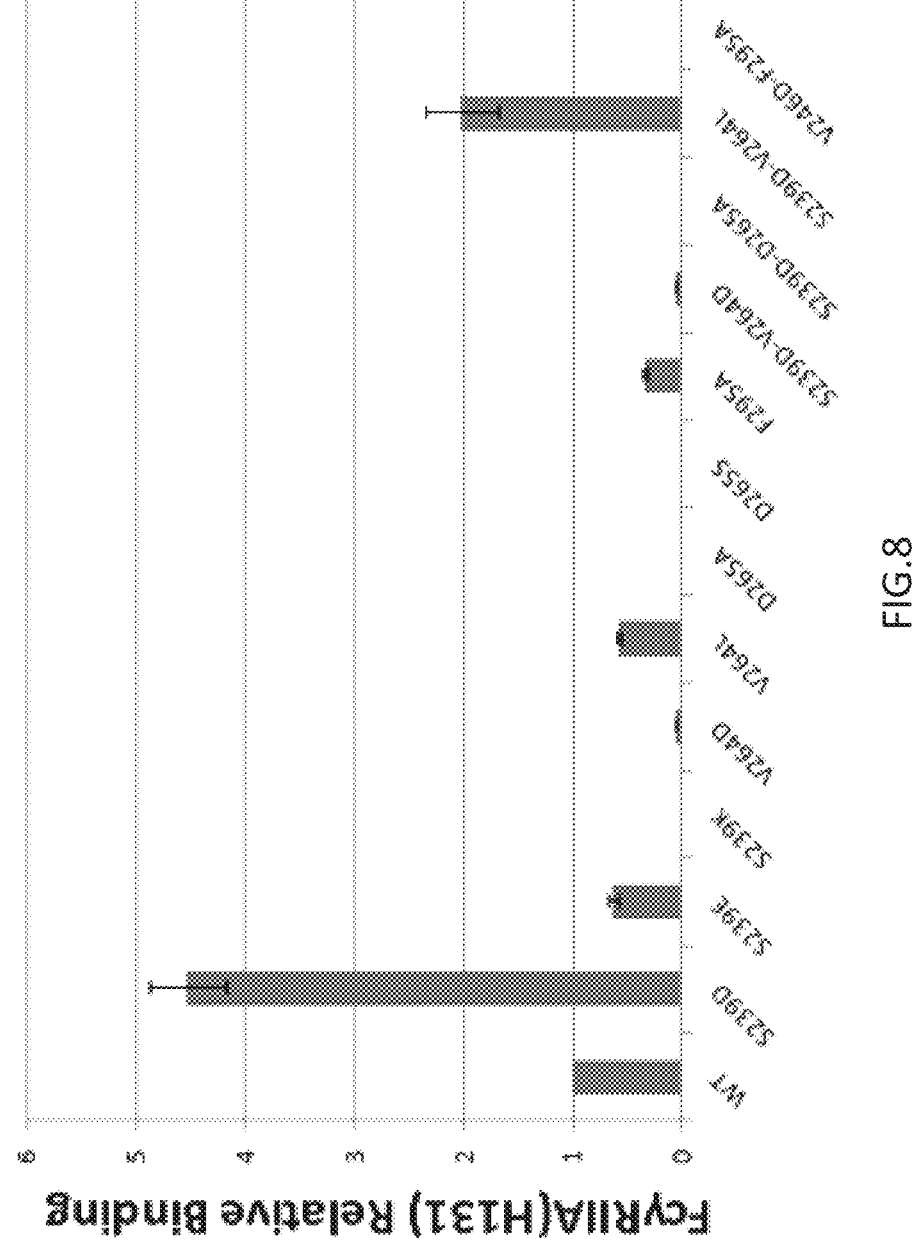
FIG. 8 FcγRIIA(H131) binding of wild-type and Fc-variant antibodies.
Figure 9:
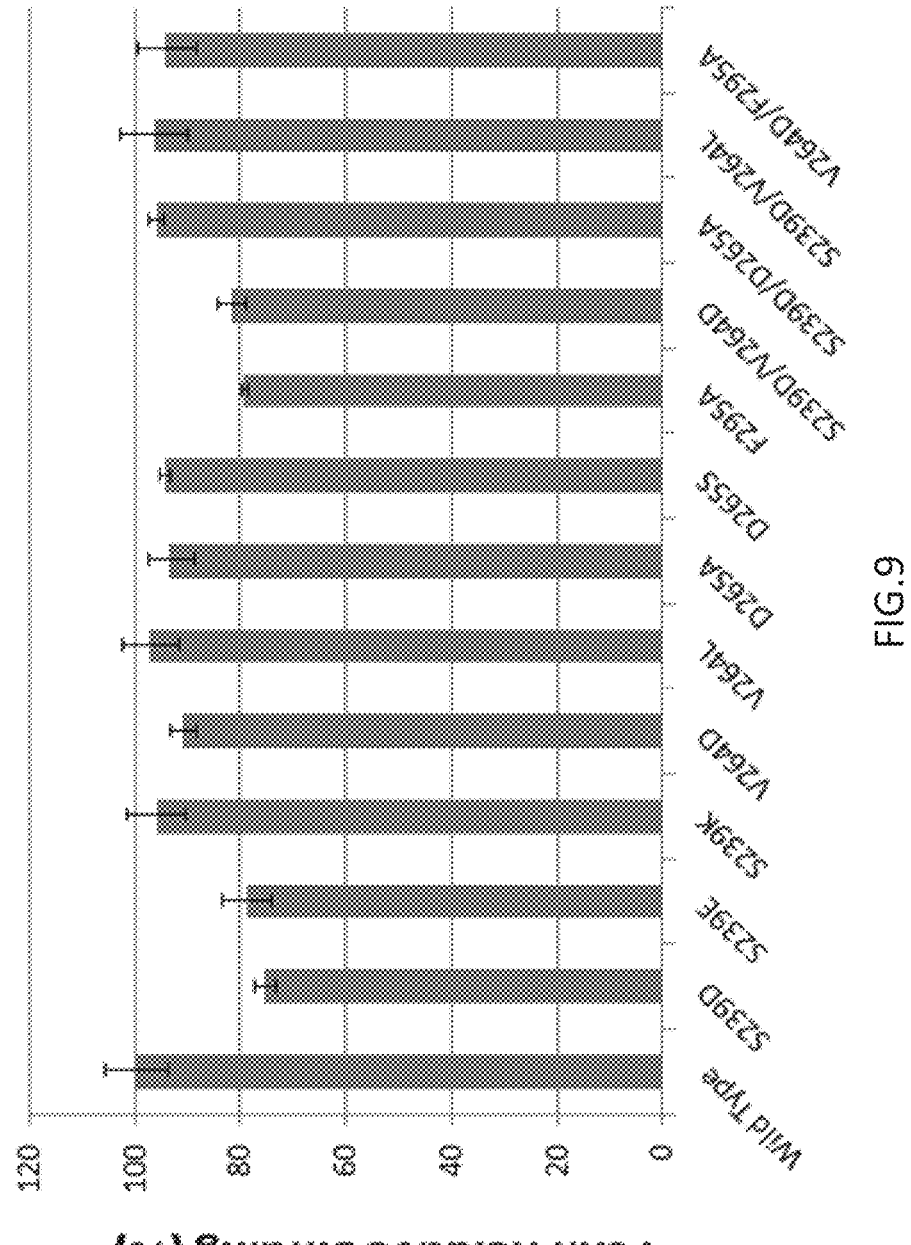
FIG. 9 FcRn binding of wild-type and Fc-variant antibodies.
Figure 10:
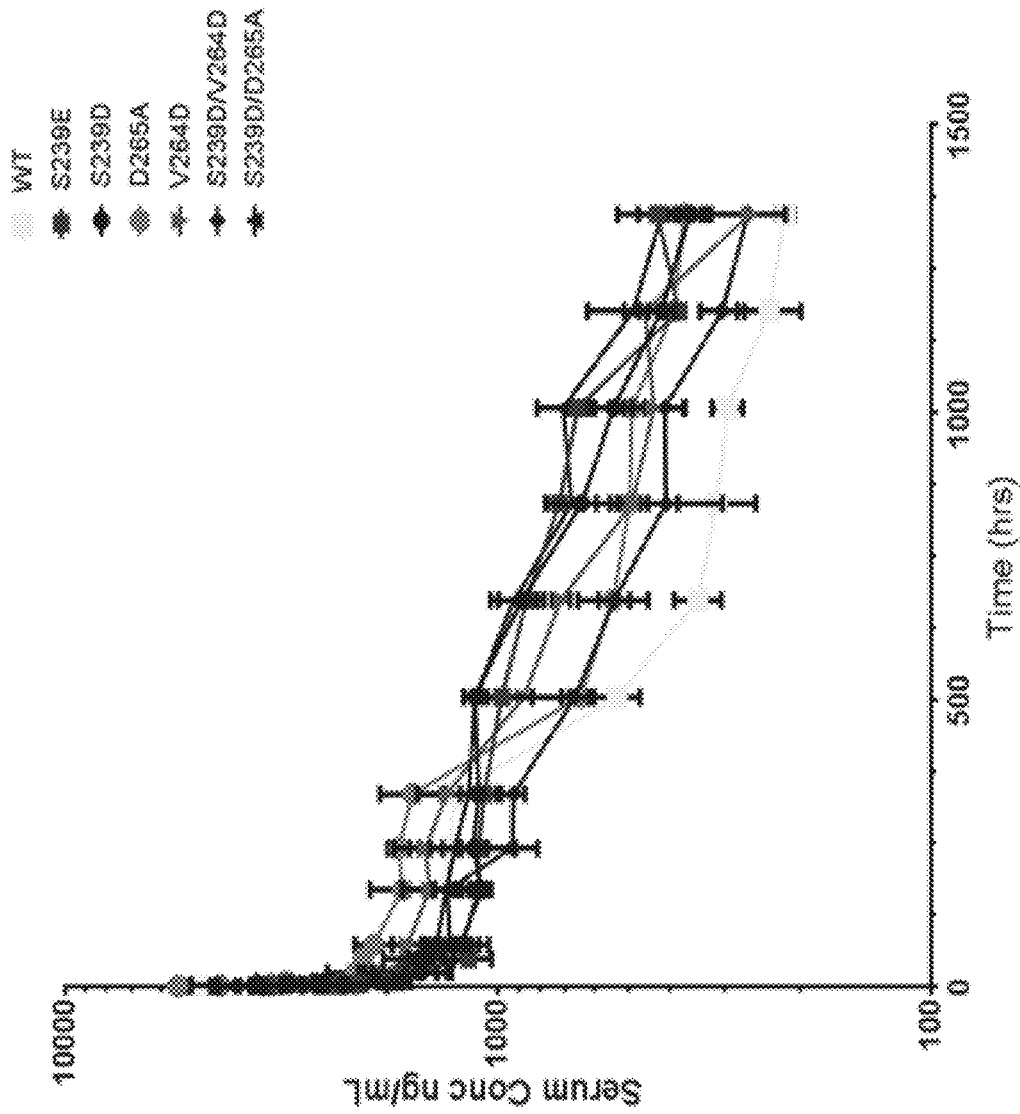
FIG. 10 Pharmacokinetic study in human FcRn-transgenic mice.

The variants did not affect Fab-antigen binding by Surface plasmon resonance assay (FIG. 7). The mutations for these residues show little impact on other attributes of mAb, such as FcγR and FcRn bindings (FIGS. 8 and 9). Pharmacokinetic study with human FcRn-transgenic mice showed all variants have the same Tmax and similar Cmax compared to wildtype (FIG. 10).

Selection of Residues that Impact Glycan Processing of mAb

Human IgG1 crystal structure was used to select 5 amino acid residues in the CH2 domain that are spatially proximal to the consensus N-glycosylation site and also the oligosaccharide chains. Besides V264 and D265 that have been examined in IgG2, additional residues are V262, Q295, and R301. The nucleotide sequence corresponding to these amino acid residues were mutated and the resulting amino acid changes are summarized in Table 3 to test whether these residues would alter glycan processing.

TABLE 3

| AA | Mutations to improve glycan processing |
| --- | --- |
| F241 | A |
| V262 | A |
| D265 | A, V |
| V264/D265 | V264L/D265A |
| Q295 | A |
| R301 | A |

Generation of Fc-Variant mAbs with Different Glycan Processing Efficiencies

The mAb constructs were transfected into CHO cells and stable pools expressing the Fc-mutant mAbs were generated. The Fc-variant mAbs were generated using a fed-batch production method, and the mAb glycosylation was analyzed by the glycan mapping describe d above.

Figure 11:
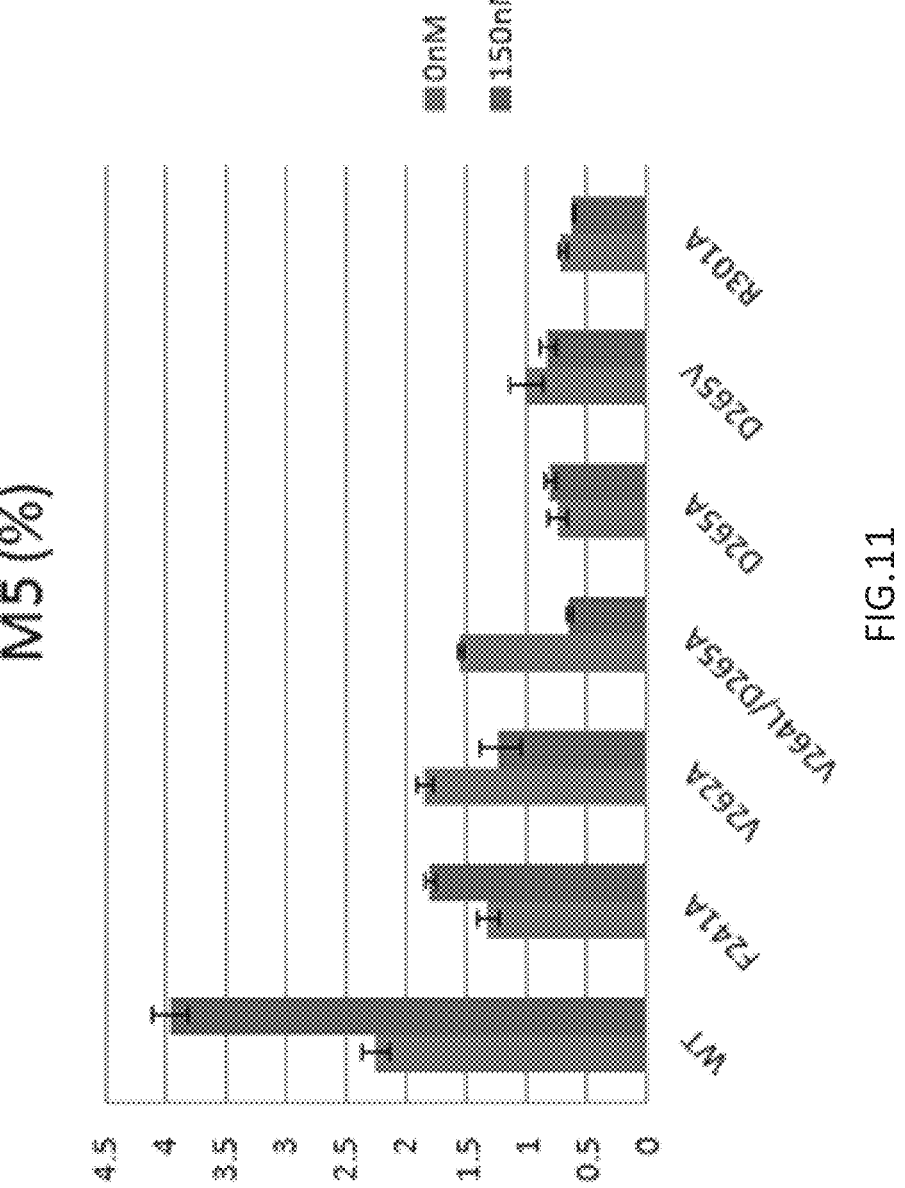
FIG. 11 M5 levels of wild-type and Fc-variant antibodies.
Figure 12:
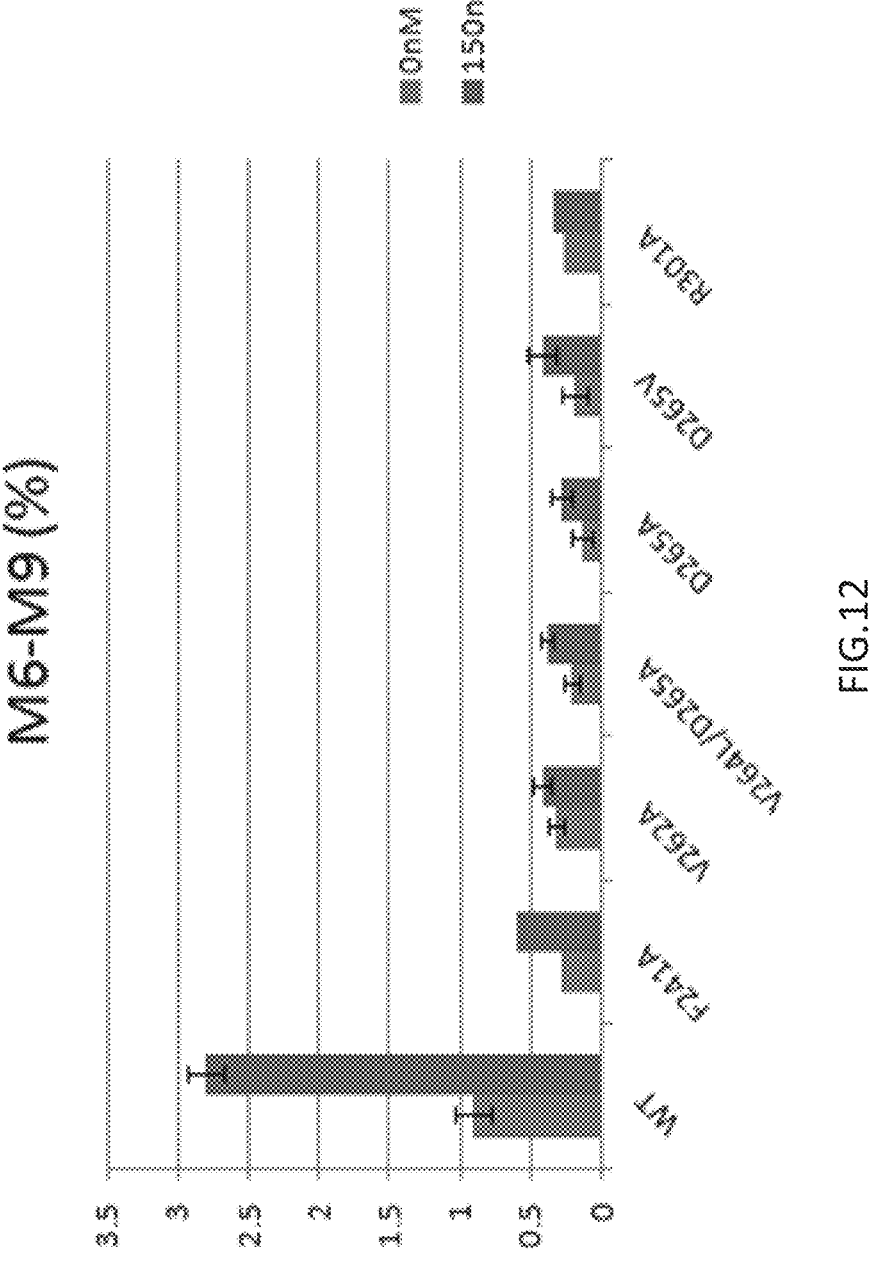
FIG. 12 High Mannose glycans (M6, M7, M8, and M9) of wild-type and Fc-variant antibodies.
Figure 13:
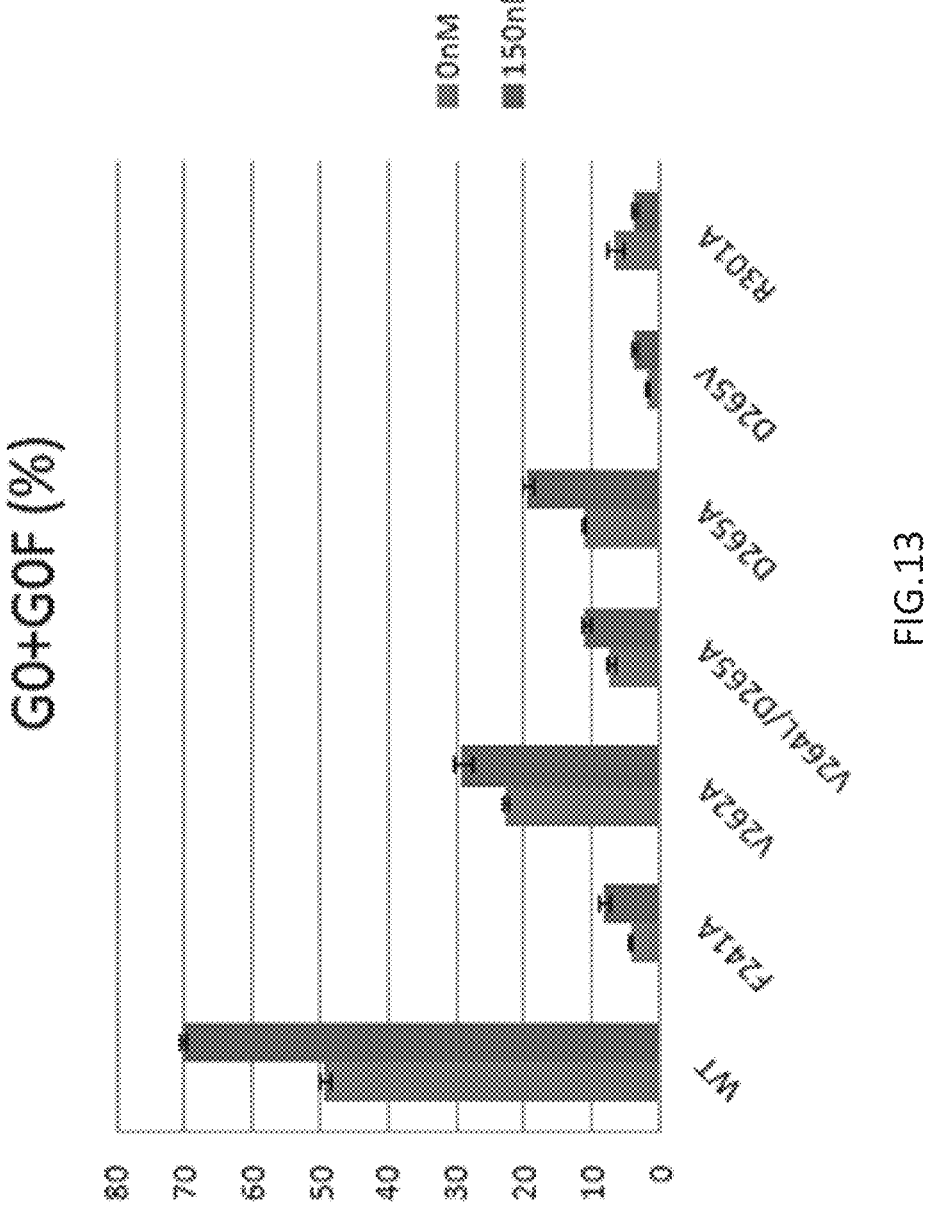
FIG. 13 Levels of immature species G0 and G0F of wild-type and Fc-variant antibodies.

As shown in FIG. 11, the Mannose 5 (M5) level of wild-type mAb is 2.25% in unamplified (0 nM) cells and increased to 4% in amplified (150 nM) cells, while single AA mutations D265A, D265V and R301A are sufficient to decrease M5 levels up to 67% compared to that of the wild type Fc (FIG. 12). The effects of D265A and D265V further confirmed previous finding from IgG2 mAb. Other mutations, such as F241A, V262A, R301, and V264L/D265A, also decreased M5 in various degrees. FIG. 13 shows decreases in the levels of a variety of other HM glycans (M6, M7, M8, and M9), suggesting improved processing of high mannose structures.

Figure 14:
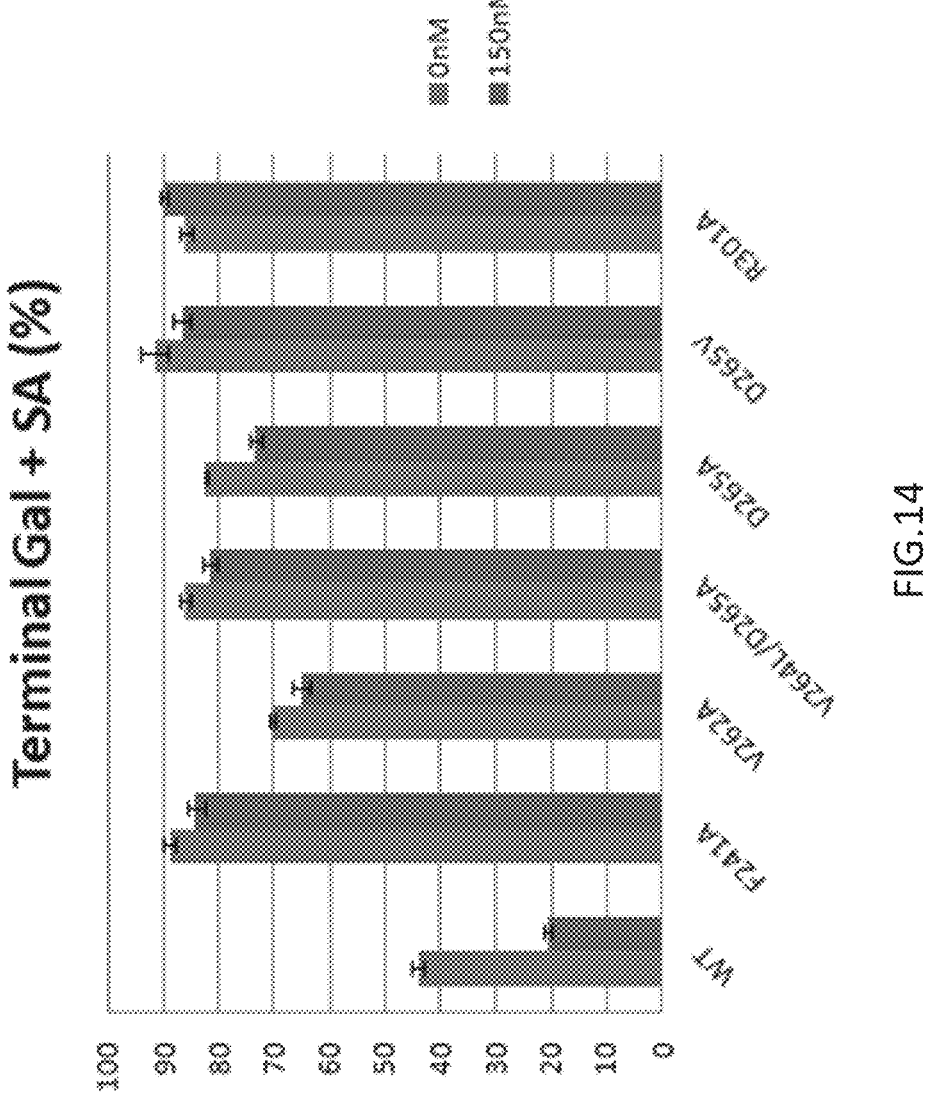
FIG. 14 Levels of galactosylated and sialylated glycan structures of wild-type and Fc-variant antibodies.
Figure 15:
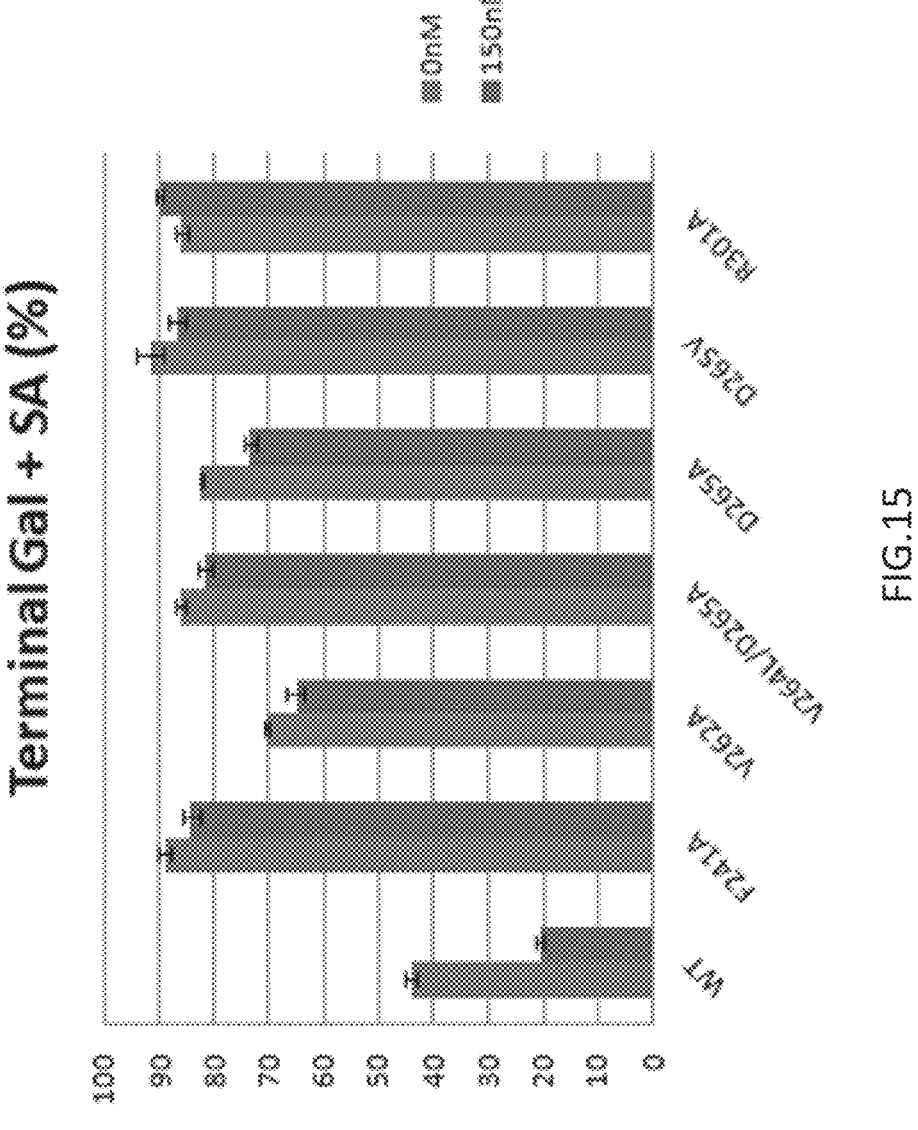
FIG. 15 Sialylation levels (SA1 and SA2) of wild-type and Fc-variant antibodies.
Figure 16:
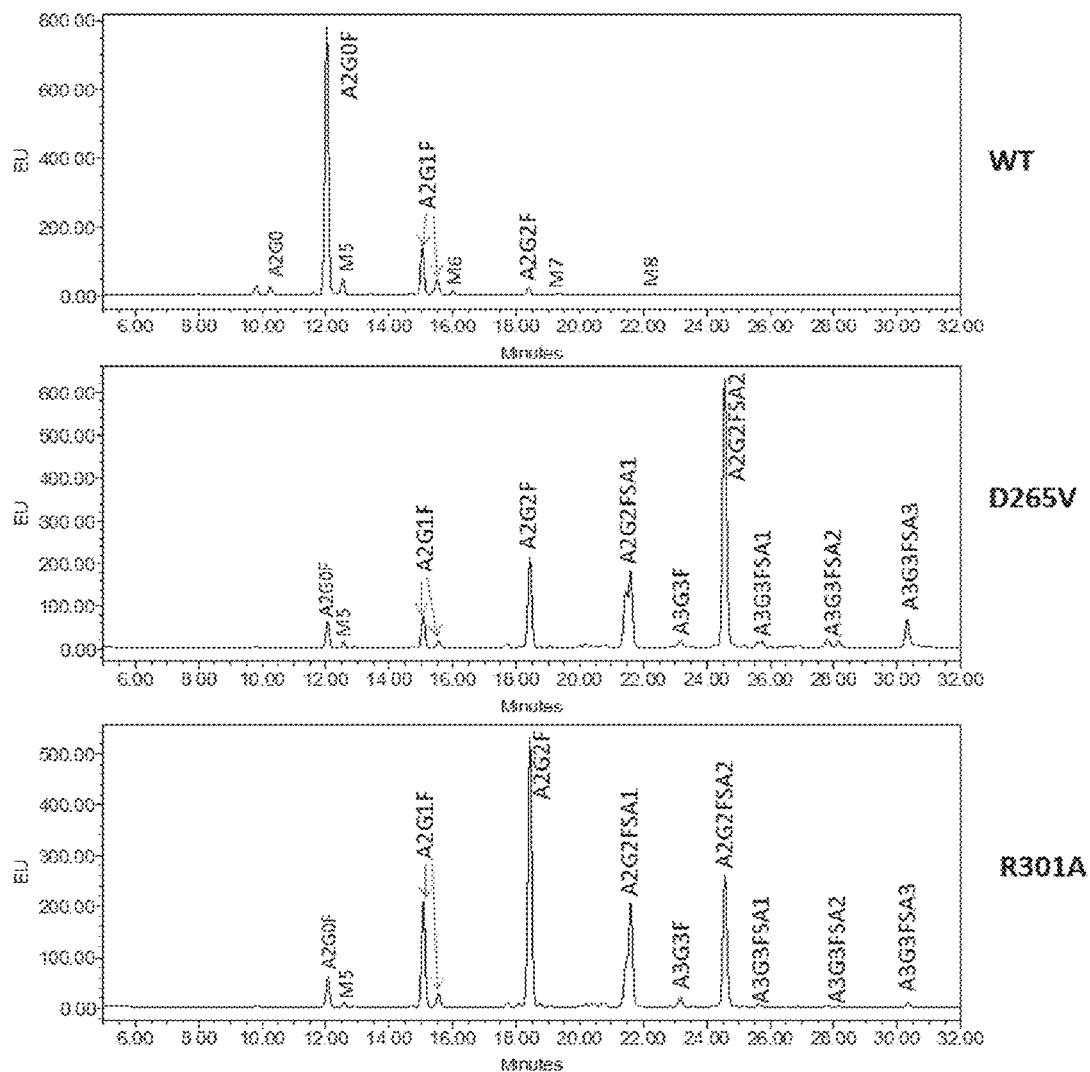
FIG. 16 Hydrophilic Interaction Chromatography (HILIC-MS)-glycan mapping of wild-type and Fc-variant antibodies.

In addition, the levels of other immature species, G0 and G0F, were also decreased in these variants (FIG. 14). These were accompanied by increases in the levels of fucosylated, galactosylated and sialylated bi-antennary glycan structures (G1F, G2F, G2FSA1, and G2FSA2), the major mature complex structures (FIGS. 15 and 17). Sialylation (SA1 and SA2), usually very low in CHO-derived mAbs, is significantly increased in these variants (30-68%), especially F241, V262A, V264L/D265A, D265V, R301A (FIGS. 16 and 17). The overall amount of the fully mature glycan level reached up to 90%, which is quite rare in CHO-derived mAb. These data suggested CHO-derived mAb that exhibited certain CH2 Fc mutations can be fully matured during glycosylation in CHO cells. It was noted that incorporation of these mutants into the antibody reduced the production of immature glycoforms levels, i.e. high mannose, G0 and G0F, to sufficiently low levels (<10% overall). Since these structures are intermediates in the pathway to synthesis of more mature structures, such as G1F, G2F, G2FSA1, G2FSA2, the decrease likely reflects the maturation by addition of core fucose, galactose, or sialic acid.

SEQUENCE LISTING

Sequence total quantity: 59
SEQ ID NO: 1                 moltype = AA   length = 250
FEATURE                      Location/Qualifiers
source                       1..250
                             mol_type = protein
                             organism = Homo sapiens
SEQUENCE: 1
YICNVNHKPS NTKVDKKVEP KSCDKTHTCP PCPAPELLGG PSVFLFPPKP KDTLMISRTP    60
EVTCVVVDVS HEDPEVKFNW YVDGVEVHNA KTKPREEQYN STYRVVSVLT VLHQDWLNGK   120
EYKCKVSNKA LPAPIEKTIS KAKGQPREPQ VYTLPPSREE MTKNQVSLTC LVKGFYPSDI   180
AVEWESNGQP ENNYKTTPPV LDSDGSFFLY SKLTVDKSRW QQGNVFSCSV MHEALHNHYT   240
QKSLSLSPGK                                                         250

SEQ ID NO: 2                 moltype = AA   length = 50
FEATURE                      Location/Qualifiers
source                       1..50
                             mol_type = protein
                             organism = Homo sapiens
SEQUENCE: 2
YICNVNHKPS NTKVDKKVEP KSCDKTHTCP PCPAPELLGG PSVFLFPPKP              50

SEQ ID NO: 3                 moltype = AA   length = 100
FEATURE                      Location/Qualifiers
source                       1..100
                             mol_type = protein
                             organism = Homo sapiens
SEQUENCE: 3
KDTLMISRTP EVTCVVVDVS HEDPEVKFNW YVDGVEVHNA KTKPREEQYN STYRVVSVLT    60
VLHQDWLNGK EYKCKVSNKA LPAPIEKTIS KAKGQPREPQ                         100

SEQ ID NO: 4                 moltype = AA   length = 100
FEATURE                      Location/Qualifiers
source                       1..100
                             mol_type = protein
                             organism = Homo sapiens
SEQUENCE: 4
VYTLPPSREE MTKNQVSLTC LVKGFYPSDI AVEWESNGQP ENNYKTTPPV LDSDGSFFLY    60
SKLTVDKSRW QQGNVFSCSV MHEALHNHYT QKSLSLSPGK                         100

SEQ ID NO: 5                 moltype = AA   length = 246
FEATURE                      Location/Qualifiers
source                       1..246
                             mol_type = protein
                             organism = Homo sapiens
SEQUENCE: 5
YTCNVDHKPS NTKVDKTVER KCCVECPPCP APPVAGPSVF LFPPKPKDTL MISRTPEVTC    60
VVVDVSHEDP EVQFNWYVDG VEVHNAKTKP REEQFNSTFR VVSVLTVVHQ DWLNGKEYKC   120
KVSNKGLPAP IEKTISKTKG QPREPQVYTL PPSREEMTKN QVSLTCLVKG FYPSDIAVEW   180
ESNGQPENNY KTTPPMLDSD GSFFLYSKLT VDKSRWQQGN VFSCSVMHEA LHNHYTQKSL   240
SLSPGK                                                             246

SEQ ID NO: 6                 moltype = AA   length = 46
FEATURE                      Location/Qualifiers
source                       1..46
                             mol_type = protein
                             organism = Homo sapiens
SEQUENCE: 6
YTCNVDHKPS NTKVDKTVER KCCVECPPCP APPVAGPSVF LFPPKP                  46

SEQ ID NO: 7                 moltype = AA   length = 99
FEATURE                      Location/Qualifiers
source                       1..99
                             mol_type = protein
                             organism = Homo sapiens
SEQUENCE: 7
DTLMISRTPE VTCVVVDVSH EDPEVQFNWY VDGVEVHNAK TKPREPQFNS TFRVVSVLTV    60
VHQDWLNGKE YKCKVSNKGL PAPIEKTISK TKGQPREPQ                          99

SEQ ID NO: 8                 moltype = AA   length = 100
FEATURE                      Location/Qualifiers
source                       1..100
                             mol_type = protein
                             organism = Homo sapiens
SEQUENCE: 8
VYTLPPSREE MTKNQVSLTC LVKGFYPSDI AVEWESNGQP ENNYKTTPPM LDSDGSFFLY    60
SKLTVDKSRW QQGNVFSCSV MHEALHNHYT QKSLSLSPGK                         100

SEQ ID NO: 9                 moltype = AA   length = 250

-continued

```
FEATURE              Location/Qualifiers
REGION               1..250
                     note = IgG1 Fc-variant S239D
source               1..250
                     mol_type = protein
                     organism = synthetic construct
SEQUENCE: 9
YICNVNHKPS NTKVDKKVEP KSCDKTHTCP PCPAPELLGG PDVFLFPPKP KDTLMISRTP   60
EVTCVVVDVS HEDPEVKFNW YVDGVEVHNA KTKPREEQYN STYRVVSVLT VLHQDWLNGK   120
EYKCKVSNKA LPAPIEKTIS KAKGQPREPQ VYTLPPSREE MTKNQVSLTC LVKGFYPSDI   180
AVEWESNGQP ENNYKTTPPV LDSDGSFFLY SKLTVDKSRW QQGNVFSCSV MHEALHNHYT   240
QKSLSLSPGK                                                         250

SEQ ID NO: 10            moltype = AA   length = 246
FEATURE                  Location/Qualifiers
REGION                   1..246
                         note = IgG2 Fc-variant S239D
source                   1..246
                         mol_type = protein
                         organism = synthetic construct
SEQUENCE: 10
YTCNVDHKPS NTKVDKTVER KCCVECPPCP APPVAGPDVF LFPPKPKDTL MISRTPEVTC   60
VVVDVSHEDP EVQFNWYVDG VEVHNAKTKP REEQFNSTFR VVSVLTVVHQ DWLNGKEYKC   120
KVSNKGLPAP IEKTISKTKG QPREPQVYTL PPSREEMTKN QVSLTCLVKG FYPSDIAVEW   180
ESNGQPENNY KTTPPMLDSD GSFFLYSKLT VDKSRWQQGN VFSCSVMHEA LHNHYTQKSL   240
SLSPGK                                                             246

SEQ ID NO: 11            moltype = AA   length = 250
FEATURE                  Location/Qualifiers
REGION                   1..250
                         note = IgG1 Fc-variant S239E
source                   1..250
                         mol_type = protein
                         organism = synthetic construct
SEQUENCE: 11
YICNVNHKPS NTKVDKKVEP KSCDKTHTCP PCPAPELLGG PEVFLFPPKP KDTLMISRTP   60
EVTCVVVDVS HEDPEVKFNW YVDGVEVHNA KTKPREEQYN STYRVVSVLT VLHQDWLNGK   120
EYKCKVSNKA LPAPIEKTIS KAKGQPREPQ VYTLPPSREE MTKNQVSLTC LVKGFYPSDI   180
AVEWESNGQP ENNYKTTPPV LDSDGSFFLY SKLTVDKSRW QQGNVFSCSV MHEALHNHYT   240
QKSLSLSPGK                                                         250

SEQ ID NO: 12            moltype = AA   length = 246
FEATURE                  Location/Qualifiers
REGION                   1..246
                         note = IgG2 Fc-variant S239E
source                   1..246
                         mol_type = protein
                         organism = synthetic construct
SEQUENCE: 12
YTCNVDHKPS NTKVDKTVER KCCVECPPCP APPVAGPEVF LFPPKPKDTL MISRTPEVTC   60
VVVDVSHEDP EVQFNWYVDG VEVHNAKTKP REEQFNSTFR VVSVLTVVHQ DWLNGKEYKC   120
KVSNKGLPAP IEKTISKTKG QPREPQVYTL PPSREEMTKN QVSLTCLVKG FYPSDIAVEW   180
ESNGQPENNY KTTPPMLDSD GSFFLYSKLT VDKSRWQQGN VFSCSVMHEA LHNHYTQKSL   240
SLSPGK                                                             246

SEQ ID NO: 13            moltype = AA   length = 250
FEATURE                  Location/Qualifiers
REGION                   1..250
                         note = IgG1 Fc-variant S239K
source                   1..250
                         mol_type = protein
                         organism = synthetic construct
SEQUENCE: 13
YICNVNHKPS NTKVDKKVEP KSCDKTHTCP PCPAPELLGG PKVFLFPPKP KDTLMISRTP   60
EVTCVVVDVS HEDPEVKFNW YVDGVEVHNA KTKPREEQYN STYRVVSVLT VLHQDWLNGK   120
EYKCKVSNKA LPAPIEKTIS KAKGQPREPQ VYTLPPSREE MTKNQVSLTC LVKGFYPSDI   180
AVEWESNGQP ENNYKTTPPV LDSDGSFFLY SKLTVDKSRW QQGNVFSCSV MHEALHNHYT   240
QKSLSLSPGK                                                         250

SEQ ID NO: 14            moltype = AA   length = 246
FEATURE                  Location/Qualifiers
REGION                   1..246
                         note = IgG2 Fc-variant S239K
source                   1..246
                         mol_type = protein
                         organism = synthetic construct
SEQUENCE: 14
YTCNVDHKPS NTKVDKTVER KCCVECPPCP APPVAGPKVF LFPPKPKDTL MISRTPEVTC   60
VVVDVSHEDP EVQFNWYVDG VEVHNAKTKP REEQFNSTFR VVSVLTVVHQ DWLNGKEYKC   120
```

```
KVSNKGLPAP IEKTISKTKG QPREPQVYTL PPSREEMTKN QVSLTCLVKG FYPSDIAVEW   180
ESNGQPENNY KTTPPMLDSD GSFFLYSKLT VDKSRWQQGN VFSCSVMHEA LHNHYTQKSL   240
SLSPGK                                                             246

SEQ ID NO: 15              moltype = AA   length = 250
FEATURE                    Location/Qualifiers
REGION                     1..250
                           note = IgG1 Fc-variant V264D
source                     1..250
                           mol_type = protein
                           organism = synthetic construct
SEQUENCE: 15
YICNVNHKPS NTKVDKKVEP KSCDKTHTCP PCPAPELLGG PSVFLFPPKP KDTLMISRTP   60
EVTCVVDDVS HEDPEVKFNW YVDGVEVHNA KTKPREEQYN STYRVVSVLT VLHQDWLNGK   120
EYKCKVSNKA LPAPIEKTIS KAKGQPREPQ VYTLPPSREE MTKNQVSLTC LVKGFYPSDI   180
AVEWESNGQP ENNYKTTPPV LDSDGSFFLY SKLTVDKSRW QQGNVFSCSV MHEALHNHYT   240
QKSLSLSPGK                                                         250

SEQ ID NO: 16              moltype = AA   length = 246
FEATURE                    Location/Qualifiers
REGION                     1..246
                           note = IgG2 Fc-variant V264D
source                     1..246
                           mol_type = protein
                           organism = synthetic construct
SEQUENCE: 16
YTCNVDHKPS NTKVDKTVER KCCVECPPCP APPVAGPSVF LFPPKPKDTL MISRTPEVTC   60
VVDDVSHEDP EVQFNWYVDG VEVHNAKTKP REEQFNSTFR VVSVLTVVHQ DWLNGKEYKC   120
KVSNKGLPAP IEKTISKTKG QPREPQVYTL PPSREEMTKN QVSLTCLVKG FYPSDIAVEW   180
ESNGQPENNY KTTPPMLDSD GSFFLYSKLT VDKSRWQQGN VFSCSVMHEA LHNHYTQKSL   240
SLSPGK                                                             246

SEQ ID NO: 17              moltype = AA   length = 250
FEATURE                    Location/Qualifiers
REGION                     1..250
                           note = IgG1 Fc-variant V264L
source                     1..250
                           mol_type = protein
                           organism = synthetic construct
SEQUENCE: 17
YICNVNHKPS NTKVDKKVEP KSCDKTHTCP PCPAPELLGG PSVFLFPPKP KDTLMISRTP   60
EVTCVVLDVS HEDPEVKFNW YVDGVEVHNA KTKPREEQYN STYRVVSVLT VLHQDWLNGK   120
EYKCKVSNKA LPAPIEKTIS KAKGQPREPQ VYTLPPSREE MTKNQVSLTC LVKGFYPSDI   180
AVEWESNGQP ENNYKTTPPV LDSDGSFFLY SKLTVDKSRW QQGNVFSCSV MHEALHNHYT   240
QKSLSLSPGK                                                         250

SEQ ID NO: 18              moltype = AA   length = 246
FEATURE                    Location/Qualifiers
REGION                     1..246
                           note = IgG2 Fc-variant V264L
source                     1..246
                           mol_type = protein
                           organism = synthetic construct
SEQUENCE: 18
YTCNVDHKPS NTKVDKTVER KCCVECPPCP APPVAGPSVF LFPPKPKDTL MISRTPEVTC   60
VVLDVSHEDP EVQFNWYVDG VEVHNAKTKP REEQFNSTFR VVSVLTVVHQ DWLNGKEYKC   120
KVSNKGLPAP IEKTISKTKG QPREPQVYTL PPSREEMTKN QVSLTCLVKG FYPSDIAVEW   180
ESNGQPENNY KTTPPMLDSD GSFFLYSKLT VDKSRWQQGN VFSCSVMHEA LHNHYTQKSL   240
SLSPGK                                                             246

SEQ ID NO: 19              moltype = AA   length = 250
FEATURE                    Location/Qualifiers
REGION                     1..250
                           note = IgG1 Fc-variant V264A
source                     1..250
                           mol_type = protein
                           organism = synthetic construct
SEQUENCE: 19
YICNVNHKPS NTKVDKKVEP KSCDKTHTCP PCPAPELLGG PSVFLFPPKP KDTLMISRTP   60
EVTCVVAVDS HEDPEVKFNW YVDGVEVHNA KTKPREEQYN STYRVVSVLT VLHQDWLNGK   120
EYKCKVSNKA LPAPIEKTIS KAKGQPREPQ VYTLPPSREE MTKNQVSLTC LVKGFYPSDI   180
AVEWESNGQP ENNYKTTPPV LDSDGSFFLY SKLTVDKSRW QQGNVFSCSV MHEALHNHYT   240
QKSLSLSPGK                                                         250

SEQ ID NO: 20              moltype = AA   length = 246
FEATURE                    Location/Qualifiers
REGION                     1..246
                           note = IgG2 Fc-variant V264A
source                     1..246
```

-continued

```
                           mol_type = protein
                           organism = synthetic construct
SEQUENCE: 20
YTCNVDHKPS NTKVDKTVER KCCVECPPCP APPVAGPSVF LFPPKPKDTL MISRTPEVTC    60
VVADVSHEDP EVQFNWYVDG VEVHNAKTKP REEQFNSTFR VVSVLTVVHQ DWLNGKEYKC   120
KVSNKGLPAP IEKTISKTKG QPREPQVYTL PPSREEMTKN QVSLTCLVKG FYPSDIAVEW   180
ESNGQPENNY KTTPPMLDSD GSFFLYSKLT VDKSRWQQGN VFSCSVMHEA LHNHYTQKSL   240
SLSPGK                                                             246

SEQ ID NO: 21              moltype = AA   length = 250
FEATURE                    Location/Qualifiers
REGION                     1..250
                           note = IgG1 Fc-variant V264S
source                     1..250
                           mol_type = protein
                           organism = synthetic construct
SEQUENCE: 21
YICNVNHKPS NTKVDKKVEP KSCDKTHTCP PCPAPELLGG PSVFLFPPKP KDTLMISRTP    60
EVTCVVSDVS HEDPEVKFNW YVDGVEVHNA KTKPREEQYN STYRVVSVLT VLHQDWLNGK   120
EYKCKVSNKA LPAPIEKTIS KAKGQPREPQ VYTLPPSREE MTKNQVSLTC LVKGFYPSDI   180
AVEWESNGQP ENNYKTTPPV LDSDGSFFLY SKLTVDKSRW QQGNVFSCSV MHEALHNHYT   240
QKSLSLSPGK                                                         250

SEQ ID NO: 22              moltype = AA   length = 246
FEATURE                    Location/Qualifiers
REGION                     1..246
                           note = IgG2 Fc-variant V264S
source                     1..246
                           mol_type = protein
                           organism = synthetic construct
SEQUENCE: 22
YTCNVDHKPS NTKVDKTVER KCCVECPPCP APPVAGPSVF LFPPKPKDTL MISRTPEVTC    60
VVSDVSHEDP EVQFNWYVDG VEVHNAKTKP REEQFNSTFR VVSVLTVVHQ DWLNGKEYKC   120
KVSNKGLPAP IEKTISKTKG QPREPQVYTL PPSREEMTKN QVSLTCLVKG FYPSDIAVEW   180
ESNGQPENNY KTTPPMLDSD GSFFLYSKLT VDKSRWQQGN VFSCSVMHEA LHNHYTQKSL   240
SLSPGK                                                             246

SEQ ID NO: 23              moltype = AA   length = 250
FEATURE                    Location/Qualifiers
REGION                     1..250
                           note = IgG1 Fc-variant D265A
source                     1..250
                           mol_type = protein
                           organism = synthetic construct
SEQUENCE: 23
YICNVNHKPS NTKVDKKVEP KSCDKTHTCP PCPAPELLGG PSVFLFPPKP KDTLMISRTP    60
EVTCVVVAVS HEDPEVKFNW YVDGVEVHNA KTKPREEQYN STYRVVSVLT VLHQDWLNGK   120
EYKCKVSNKA LPAPIEKTIS KAKGQPREPQ VYTLPPSREE MTKNQVSLTC LVKGFYPSDI   180
AVEWESNGQP ENNYKTTPPV LDSDGSFFLY SKLTVDKSRW QQGNVFSCSV MHEALHNHYT   240
QKSLSLSPGK                                                         250

SEQ ID NO: 24              moltype = AA   length = 246
FEATURE                    Location/Qualifiers
REGION                     1..246
                           note = IgG2 Fc-variant D265A
source                     1..246
                           mol_type = protein
                           organism = synthetic construct
SEQUENCE: 24
YTCNVDHKPS NTKVDKTVER KCCVECPPCP APPVAGPSVF LFPPKPKDTL MISRTPEVTC    60
VVVAVSHEDP EVQFNWYVDG VEVHNAKTKP REEQFNSTFR VVSVLTVVHQ DWLNGKEYKC   120
KVSNKGLPAP IEKTISKTKG QPREPQVYTL PPSREEMTKN QVSLTCLVKG FYPSDIAVEW   180
ESNGQPENNY KTTPPMLDSD GSFFLYSKLT VDKSRWQQGN VFSCSVMHEA LHNHYTQKSL   240
SLSPGK                                                             246

SEQ ID NO: 25              moltype = AA   length = 250
FEATURE                    Location/Qualifiers
REGION                     1..250
                           note = IgG1 Fc-variant D265S
source                     1..250
                           mol_type = protein
                           organism = synthetic construct
SEQUENCE: 25
YICNVNHKPS NTKVDKKVEP KSCDKTHTCP PCPAPELLGG PSVFLFPPKP KDTLMISRTP    60
EVTCVVVSVS HEDPEVKFNW YVDGVEVHNA KTKPREEQYN STYRVVSVLT VLHQDWLNGK   120
EYKCKVSNKA LPAPIEKTIS KAKGQPREPQ VYTLPPSREE MTKNQVSLTC LVKGFYPSDI   180
AVEWESNGQP ENNYKTTPPV LDSDGSFFLY SKLTVDKSRW QQGNVFSCSV MHEALHNHYT   240
QKSLSLSPGK                                                         250
```

-continued

```
SEQ ID NO: 26              moltype = AA   length = 246
FEATURE                    Location/Qualifiers
REGION                     1..246
                           note = IgG2 Fc-variant D265S
source                     1..246
                           mol_type = protein
                           organism = synthetic construct
SEQUENCE: 26
YTCNVDHKPS NTKVDKTVER KCCVECPPCP APPVAGPSVF LFPPKPKDTL MISRTPEVTC   60
VVVSVSHEDP EVQFNWYVDG VEVHNAKTKP REEQFNSTFR VVSVLTVVHQ DWLNGKEYKC  120
KVSNKGLPAP IEKTISKTKG QPREPQVYTL PPSREEMTKN QVSLTCLVKG FYPSDIAVEW  180
ESNGQPENNY KTTPPMLDSD GSFFLYSKLT VDKSRWQQGN VFSCSVMHEA LHNHYTQKSL  240
SLSPGK                                                             246

SEQ ID NO: 27              moltype = AA   length = 250
FEATURE                    Location/Qualifiers
REGION                     1..250
                           note = IgG1 Fc-variant Y296A
source                     1..250
                           mol_type = protein
                           organism = synthetic construct
SEQUENCE: 27
YICNVNHKPS NTKVDKKVEP KSCDKTHTCP PCPAPELLGG PSVFLFPPKP KDTLMISRTP   60
EVTCVVVDVS HEDPEVKFNW YVDGVEVHNA KTKPREEQYN STARVVSVLT VLHQDWLNGK  120
EYKCKVSNKA LPAPIEKTIS KAKGQPREPQ VYTLPPSREE MTKNQVSLTC LVKGFYPSDI  180
AVEWESNGQP ENNYKTTPPV LDSDGSFFLY SKLTVDKSRW QQGNVFSCSV MHEALHNHYT  240
QKSLSLSPGK                                                         250

SEQ ID NO: 28              moltype = AA   length = 246
FEATURE                    Location/Qualifiers
REGION                     1..246
                           note = IgG2 Fc-variant F296A
source                     1..246
                           mol_type = protein
                           organism = synthetic construct
SEQUENCE: 28
YTCNVDHKPS NTKVDKTVER KCCVECPPCP APPVAGPSVF LFPPKPKDTL MISRTPEVTC   60
VVVSVSHEDP EVQFNWYVDG VEVHNAKTKP REEQFNSTAR VVSVLTVVHQ DWLNGKEYKC  120
KVSNKGLPAP IEKTISKTKG QPREPQVYTL PPSREEMTKN QVSLTCLVKG FYPSDIAVEW  180
ESNGQPENNY KTTPPMLDSD GSFFLYSKLT VDKSRWQQGN VFSCSVMHEA LHNHYTQKSL  240
SLSPGK                                                             246

SEQ ID NO: 29              moltype = AA   length = 250
FEATURE                    Location/Qualifiers
REGION                     1..250
                           note = IgG1 Fc-variant S239D and V264D
source                     1..250
                           mol_type = protein
                           organism = synthetic construct
SEQUENCE: 29
YICNVNHKPS NTKVDKKVEP KSCDKTHTCP PCPAPELLGG PDVFLFPPKP KDTLMISRTP   60
EVTCVVDDVS HEDPEVKFNW YVDGVEVHNA KTKPREEQYN STYRVVSVLT VLHQDWLNGK  120
EYKCKVSNKA LPAPIEKTIS KAKGQPREPQ VYTLPPSREE MTKNQVSLTC LVKGFYPSDI  180
AVEWESNGQP ENNYKTTPPV LDSDGSFFLY SKLTVDKSRW QQGNVFSCSV MHEALHNHYT  240
QKSLSLSPGK                                                         250

SEQ ID NO: 30              moltype = AA   length = 246
FEATURE                    Location/Qualifiers
REGION                     1..246
                           note = IgG2 Fc-variant S239D and V264D
source                     1..246
                           mol_type = protein
                           organism = synthetic construct
SEQUENCE: 30
YTCNVDHKPS NTKVDKTVER KCCVECPPCP APPVAGPDVF LFPPKPKDTL MISRTPEVTC   60
VVDDVSHEDP EVQFNWYVDG VEVHNAKTKP REEQFNSTFR VVSVLTVVHQ DWLNGKEYKC  120
KVSNKGLPAP IEKTISKTKG QPREPQVYTL PPSREEMTKN QVSLTCLVKG FYPSDIAVEW  180
ESNGQPENNY KTTPPMLDSD GSFFLYSKLT VDKSRWQQGN VFSCSVMHEA LHNHYTQKSL  240
SLSPGK                                                             246

SEQ ID NO: 31              moltype = AA   length = 250
FEATURE                    Location/Qualifiers
REGION                     1..250
                           note = IgG1 Fc-variant S239D and V264L
source                     1..250
                           mol_type = protein
                           organism = synthetic construct
SEQUENCE: 31
YICNVNHKPS NTKVDKKVEP KSCDKTHTCP PCPAPELLGG PDVFLFPPKP KDTLMISRTP   60
```

```
EVTCVVLDVS HEDPEVKFNW YVDGVEVHNA KTKPREEQYN STYRVVSVLT VLHQDWLNGK    120
EYKCKVSNKA LPAPIEKTIS KAKGQPREPQ VYTLPPSREE MTKNQVSLTC LVKGFYPSDI    180
AVEWESNGQP ENNYKTTPPV LDSDGSFFLY SKLTVDKSRW QQGNVFSCSV MHEALHNHYT    240
QKSLSLSPGK                                                          250

SEQ ID NO: 32              moltype = AA   length = 246
FEATURE                    Location/Qualifiers
REGION                     1..246
                           note = IgG2 Fc-variant S239D and V264L
source                     1..246
                           mol_type = protein
                           organism = synthetic construct
SEQUENCE: 32
YTCNVDHKPS NTKVDKTVER KCCVECPPCP APPVAGPDVF LFPPKPKDTL MISRTPEVTC     60
VVLDVSHEDP EVQFNWYVDG VEVHNAKTKP REEQFNSTFR VVSVLTVVHQ DWLNGKEYKC    120
KVSNKGLPAP IEKTISKTKG QPREPQVYTL PPSREEMTKN QVSLTCLVKG FYPSDIAVEW    180
ESNGQPENNY KTTPPMLDSD GSFFLYSKLT VDKSRWQQGN VFSCSVMHEA LHNHYTQKSL    240
SLSPGK                                                              246

SEQ ID NO: 33              moltype = AA   length = 250
FEATURE                    Location/Qualifiers
REGION                     1..250
                           note = IgG1 Fc-variant S239D and D265A
source                     1..250
                           mol_type = protein
                           organism = synthetic construct
SEQUENCE: 33
YICNVNHKPS NTKVDKKVEP KSCDKTHTCP PCPAPELLGG PDVFLFPPKP KDTLMISRTP     60
EVTCVVVAVS HEDPEVKFNW YVDGVEVHNA KTKPREEQYN STYRVVSVLT VLHQDWLNGK    120
EYKCKVSNKA LPAPIEKTIS KAKGQPREPQ VYTLPPSREE MTKNQVSLTC LVKGFYPSDI    180
AVEWESNGQP ENNYKTTPPV LDSDGSFFLY SKLTVDKSRW QQGNVFSCSV MHEALHNHYT    240
QKSLSLSPGK                                                          250

SEQ ID NO: 34              moltype = AA   length = 246
FEATURE                    Location/Qualifiers
REGION                     1..246
                           note = IgG2 Fc-variant S239D and D265A
source                     1..246
                           mol_type = protein
                           organism = synthetic construct
SEQUENCE: 34
YTCNVDHKPS NTKVDKTVER KCCVECPPCP APPVAGPDVF LFPPKPKDTL MISRTPEVTC     60
VVVAVSHEDP EVQFNWYVDG VEVHNAKTKP REEQFNSTFR VVSVLTVVHQ DWLNGKEYKC    120
KVSNKGLPAP IEKTISKTKG QPREPQVYTL PPSREEMTKN QVSLTCLVKG FYPSDIAVEW    180
ESNGQPENNY KTTPPMLDSD GSFFLYSKLT VDKSRWQQGN VFSCSVMHEA LHNHYTQKSL    240
SLSPGK                                                              246

SEQ ID NO: 35              moltype = AA   length = 250
FEATURE                    Location/Qualifiers
REGION                     1..250
                           note = IgG1 Fc-variant V264D and Y296A
source                     1..250
                           mol_type = protein
                           organism = synthetic construct
SEQUENCE: 35
YICNVNHKPS NTKVDKKVEP KSCDKTHTCP PCPAPELLGG PSVFLFPPKP KDTLMISRTP     60
EVTCVVDDVS HEDPEVKFNW YVDGVEVHNA KTKPREEQAN STYRVVSVLT VLHQDWLNGK    120
EYKCKVSNKA LPAPIEKTIS KAKGQPREPQ VYTLPPSREE MTKNQVSLTC LVKGFYPSDI    180
AVEWESNGQP ENNYKTTPPV LDSDGSFFLY SKLTVDKSRW QQGNVFSCSV MHEALHNHYT    240
QKSLSLSPGK                                                          250

SEQ ID NO: 36              moltype = AA   length = 246
FEATURE                    Location/Qualifiers
REGION                     1..246
                           note = IgG2 Fc-variant V264D and F296A
source                     1..246
                           mol_type = protein
                           organism = synthetic construct
SEQUENCE: 36
YTCNVDHKPS NTKVDKTVER KCCVECPPCP APPVAGPSVF LFPPKPKDTL MISRTPEVTC     60
VVDDVSHEDP EVQFNWYVDG VEVHNAKTKP REEQANSTFR VVSVLTVVHQ DWLNGKEYKC    120
KVSNKGLPAP IEKTISKTKG QPREPQVYTL PPSREEMTKN QVSLTCLVKG FYPSDIAVEW    180
ESNGQPENNY KTTPPMLDSD GSFFLYSKLT VDKSRWQQGN VFSCSVMHEA LHNHYTQKSL    240
SLSPGK                                                              246

SEQ ID NO: 37              moltype = DNA   length = 33
FEATURE                    Location/Qualifiers
misc_feature               1..33
                           note = Primer
```

```
source                 1..33
                       mol_type = other DNA
                       organism = synthetic construct
SEQUENCE: 37
cctgtggcag gaccggacgt cttcctcttc ccc                              33

SEQ ID NO: 38          moltype = DNA   length = 34
FEATURE                Location/Qualifiers
misc_feature           1..34
                       note = Primer
source                 1..34
                       mol_type = other DNA
                       organism = synthetic construct
SEQUENCE: 38
cacctgtggc aggaccgcag gtcttcctct tccc                             34

SEQ ID NO: 39          moltype = DNA   length = 34
FEATURE                Location/Qualifiers
misc_feature           1..34
                       note = Primer
source                 1..34
                       mol_type = other DNA
                       organism = synthetic construct
SEQUENCE: 39
cacctgtggc aggaccgcag gtcttcctct tcc                              34

SEQ ID NO: 40          moltype = DNA   length = 32
FEATURE                Location/Qualifiers
misc_feature           1..32
                       note = Primer
source                 1..32
                       mol_type = other DNA
                       organism = synthetic construct
SEQUENCE: 40
cacgtgcgtg gtggacgacg tgagccacga ag                               32

SEQ ID NO: 41          moltype = DNA   length = 28
FEATURE                Location/Qualifiers
misc_feature           1..28
                       note = Primer
source                 1..28
                       mol_type = other DNA
                       organism = synthetic construct
SEQUENCE: 41
cacgtgcgtg gtgctggacg tgagccac                                    28

SEQ ID NO: 42          moltype = DNA   length = 32
FEATURE                Location/Qualifiers
misc_feature           1..32
                       note = Primer
source                 1..32
                       mol_type = other DNA
                       organism = synthetic construct
SEQUENCE: 42
cgtgcgtggt ggtggcagtg agccacgaag ac                               32

SEQ ID NO: 43          moltype = DNA   length = 34
FEATURE                Location/Qualifiers
misc_feature           1..34
                       note = Primer
source                 1..34
                       mol_type = other DNA
                       organism = synthetic construct
SEQUENCE: 43
cacgtgcgtg gtggtgctcg tgagccacga agac                             34

SEQ ID NO: 44          moltype = DNA   length = 34
FEATURE                Location/Qualifiers
misc_feature           1..34
                       note = Primer
source                 1..34
                       mol_type = other DNA
                       organism = synthetic construct
SEQUENCE: 44
cacgtgcgtg gtggtgtccg tgagccacga agac                             34

SEQ ID NO: 45          moltype = DNA   length = 38
FEATURE                Location/Qualifiers
misc_feature           1..38
```

```
                        note = Primer
source                  1..38
                        mol_type = other DNA
                        organism = synthetic construct
SEQUENCE: 45
gaagaccccg aggtccaggc taactggtac gtggacgg                                38

SEQ ID NO: 46           moltype = DNA   length = 41
FEATURE                 Location/Qualifiers
misc_feature            1..41
                        note = Primer
source                  1..41
                        mol_type = other DNA
                        organism = synthetic construct
SEQUENCE: 46
gaggtcacgt gcgtggtgga cgctgtgagc cacgaagacc c                            41

SEQ ID NO: 47           moltype = AA   length = 5
FEATURE                 Location/Qualifiers
REGION                  1..5
                        note = Peptide
source                  1..5
                        mol_type = protein
                        organism = synthetic construct
SEQUENCE: 47
GGGGS                                                                     5

SEQ ID NO: 48           moltype = AA   length = 5
FEATURE                 Location/Qualifiers
REGION                  1..5
                        note = Peptide
source                  1..5
                        mol_type = protein
                        organism = synthetic construct
SEQUENCE: 48
GGNGT                                                                     5

SEQ ID NO: 49           moltype = AA   length = 5
FEATURE                 Location/Qualifiers
REGION                  1..5
                        note = Peptide
source                  1..5
                        mol_type = protein
                        organism = synthetic construct
SEQUENCE: 49
YGNGT                                                                     5

SEQ ID NO: 50           moltype = AA   length = 250
FEATURE                 Location/Qualifiers
REGION                  1..250
                        note = IgG1 Fc-variant F241A
source                  1..250
                        mol_type = protein
                        organism = synthetic construct
SEQUENCE: 50
YICNVNHKPS NTKVDKKVEP KSCDKTHTCP PCPAPELLGG PSVALFPPKP KDTLMISRTP  60
EVTCVVVDVS HEDPEVKFNW YVDGVEVHNA KTKPREEQYN STYRVVSVLT VLHQDWLNGK  120
EYKCKVSNKA LPAPIEKTIS KAKGQPREPQ VYTLPPSRDE LTKNQVSLTC LVKGFYPSDI  180
AVEWESNGQP ENNYKTTPPV LDSDGSFFLY SKLTVDKSRW QQGNVFSCSV MHEALHNHYT  240
QKSLSLSPGK                                                         250

SEQ ID NO: 51           moltype = AA   length = 246
FEATURE                 Location/Qualifiers
REGION                  1..246
                        note = IgG2 Fc-variant F241A
source                  1..246
                        mol_type = protein
                        organism = synthetic construct
SEQUENCE: 51
YTCNVDHKPS NTKVDKTVER KCCVECPPCP APPVAGPSVA LFPPKPKDTL MISRTPEVTC  60
VVVDVSHEDP EVQFNWYVDG VEVHNAKTKP REEQFNSTFR VVSVLTVVHQ DWLNGKEYKC  120
KVSNKGLPAP IEKTISKTKG QPREPQVYTL PPSREEMTKN QVSLTCLVKG FYPSDIAVEW  180
ESNGQPENNY KTTPPMLDSD GSFFLYSKLT VDKSRWQQGN VFSCSVMHEA LHNHYTQKSL  240
SLSPGK                                                             246

SEQ ID NO: 52           moltype = AA   length = 250
FEATURE                 Location/Qualifiers
REGION                  1..250
                        note = IgG1 Fc-variant V262A
```

-continued

```
source                   1..250
                         mol_type = protein
                         organism = synthetic construct
SEQUENCE: 52
YICNVNHKPS NTKVDKKVEP KSCDKTHTCP PCPAPELLGG PSVFLFPPKP KDTLMISRTP   60
EVTCAVVDVS HEDPEVKFNW YVDGVEVHNA KTKPREEQYN STYRVVSVLT VLHQDWLNGK  120
EYKCKVSNKA LPAPIEKTIS KAKGQPREPQ VYTLPPSRDE LTKNQVSLTC LVKGFYPSDI  180
AVEWESNGQP ENNYKTTPPV LDSDGSFFLY SKLTVDKSRW QQGNVFSCSV MHEALHNHYT  240
QKSLSLSPGK                                                        250

SEQ ID NO: 53            moltype = AA  length = 246
FEATURE                  Location/Qualifiers
REGION                   1..246
                         note = IgG2 Fc-variant V262A
source                   1..246
                         mol_type = protein
                         organism = synthetic construct
SEQUENCE: 53
YTCNVDHKPS NTKVDKTVER KCCVECPPCP APPVAGPSVF LFPPKPKDTL MISRTPEVTC   60
AVVDVSHEDP EVQFNWYVDG VEVHNAKTKP REEQFNSTFR VVSVLTVVHQ DWLNGKEYKC  120
KVSNKGLPAP IEKTISKTKG QPREPQVYTL PPSREEMTKN QVSLTCLVKG FYPSDIAVEW  180
ESNGQPENNY KTTPPMLDSD GSFFLYSKLT VDKSRWQQGN VFSCSVMHEA LHNHYTQKSL  240
SLSPGK                                                            246

SEQ ID NO: 54            moltype = AA  length = 250
FEATURE                  Location/Qualifiers
REGION                   1..250
                         note = IgG1 Fc-variant D265V
source                   1..250
                         mol_type = protein
                         organism = synthetic construct
SEQUENCE: 54
YICNVNHKPS NTKVDKKVEP KSCDKTHTCP PCPAPELLGG PSVFLFPPKP KDTLMISRTP   60
EVTCVVVDVS HEDPEVKFNW YVDGVEVHNA KTKPREEQYN STYRVVSVLT VLHQDWLNGK  120
EYKCKVSNKA LPAPIEKTIS KAKGQPREPQ VYTLPPSREE MTKNQVSLTC LVKGFYPSDI  180
AVEWESNGQP ENNYKTTPPV LDSDGSFFLY SKLTVDKSRW QQGNVFSCSV MHEALHNHYT  240
QKSLSLSPGK                                                        250

SEQ ID NO: 55            moltype = AA  length = 246
FEATURE                  Location/Qualifiers
REGION                   1..246
                         note = IgG2 Fc-variant D265V
source                   1..246
                         mol_type = protein
                         organism = synthetic construct
SEQUENCE: 55
YTCNVDHKPS NTKVDKTVER KCCVECPPCP APPVAGPSVF LFPPKPKDTL MISRTPEVTC   60
VVVVVSHEDP EVQFNWYVDG VEVHNAKTKP REEQFNSTFR VVSVLTVVHQ DWLNGKEYKC  120
KVSNKGLPAP IEKTISKTKG QPREPQVYTL PPSREEMTKN QVSLTCLVKG FYPSDIAVEW  180
ESNGQPENNY KTTPPMLDSD GSFFLYSKLT VDKSRWQQGN VFSCSVMHEA LHNHYTQKSL  240
SLSPGK                                                            246

SEQ ID NO: 56            moltype = AA  length = 250
FEATURE                  Location/Qualifiers
REGION                   1..250
                         note = IgG1 Fc-variant R301A
source                   1..250
                         mol_type = protein
                         organism = synthetic construct
SEQUENCE: 56
YICNVNHKPS NTKVDKKVEP KSCDKTHTCP PCPAPELLGG PSVFLFPPKP KDTLMISRTP   60
EVTCVVVDVS HEDPEVKFNW YVDGVEVHNA KTKPREEQYN STYAVVSVLT VLHQDWLNGK  120
EYKCKVSNKA LPAPIEKTIS KAKGQPREPQ VYTLPPSREE MTKNQVSLTC LVKGFYPSDI  180
AVEWESNGQP ENNYKTTPPV LDSDGSFFLY SKLTVDKSRW QQGNVFSCSV MHEALHNHYT  240
QKSLSLSPGK                                                        250

SEQ ID NO: 57            moltype = AA  length = 246
FEATURE                  Location/Qualifiers
REGION                   1..246
                         note = IgG2 Fc-variant R301A
source                   1..246
                         mol_type = protein
                         organism = synthetic construct
SEQUENCE: 57
YTCNVDHKPS NTKVDKTVER KCCVECPPCP APPVAGPSVF LFPPKPKDTL MISRTPEVTC   60
VVVDVSHEDP EVQFNWYVDG VEVHNAKTKP REEQFNSTFA VVSVLTVVHQ DWLNGKEYKC  120
KVSNKGLPAP IEKTISKTKG QPREPQVYTL PPSREEMTKN QVSLTCLVKG FYPSDIAVEW  180
ESNGQPENNY KTTPPMLDSD GSFFLYSKLT VDKSRWQQGN VFSCSVMHEA LHNHYTQKSL  240
SLSPGK                                                            246
```

-continued

```
SEQ ID NO: 58          moltype = AA  length = 250
FEATURE                Location/Qualifiers
REGION                 1..250
                       note = IgG1 Fc-variant V264L and D265A
source                 1..250
                       mol_type = protein
                       organism = synthetic construct
SEQUENCE: 58
YICNVNHKPS NTKVDKKVEP KSCDKTHTCP PCPAPELLGG PSVFLFPPKP KDTLMISRTP  60
EVTCVVLAVS HEDPEVKFNW YVDGVEVHNA KTKPREEQYN STYRVVSVLT VLHQDWLNGK  120
EYKCKVSNKA LPAPIEKTIS KAKGQPREPQ VYTLPPSREE MTKNQVSLTC LVKGFYPSDI  180
AVEWESNGQP ENNYKTTPPV LDSDGSFFLY SKLTVDKSRW QQGNVFSCSV MHEALHNHYT  240
QKSLSLSPGK                                                        250

SEQ ID NO: 59          moltype = AA  length = 246
FEATURE                Location/Qualifiers
REGION                 1..246
                       note = IgG2 Fc-variant V264L and D265A
source                 1..246
                       mol_type = protein
                       organism = synthetic construct
SEQUENCE: 59
YTCNVDHKPS NTKVDKTVER KCCVECPPCP APPVAGPSVF LFPPKPKDTL MISRTPEVTC  60
VVLAVSHEDP EVQFNWYVDG VEVHNAKTKP REEQFNSTFR VVSVLTVVHQ DWLNGKEYKC  120
KVSNKGLPAP IEKTISKTKG QPREPQVYTL PPSREEMTKN QVSLTCLVKG FYPSDIAVEW  180
ESNGQPENNY KTTPPMLDSD GSFFLYSKLT VDKSRWQQGN VFSCSVMHEA LHNHYTQKSL  240
SLSPGK                                                            246
```

What is claimed:

1. An Fc-containing molecule, wherein the Fc comprises the amino acid sequence set forth in SEQ ID NO:1 or SEQ ID NO:5, except two amino acid substitutions selected from the group consisting of: S239D/D265A, S239D/V264L, V264L/D265A, and V264D/F296A, according to the EU numbering scheme.

2. The Fc-containing molecule of claim 1, wherein the Fc comprises a S239D substitution and a D265A or V264L substitution.

3. The Fc-containing molecule of claim 2, wherein the Fc comprises a S239D substitution and a V264L substitution.

4. The Fc-containing molecule of claim 2, wherein the Fc comprises a S239D substitution and a D265A substitution.

5. The Fc-containing molecule of claim 1, wherein the Fc comprises a V264D substitution and a F296A substitution.

6. The Fc-containing molecule of claim 1, wherein the Fc comprises a V264L substitution and a D265A substitution.

7. The Fc-containing molecule of claim 1, wherein the Fc-containing molecule is an antibody or an Fc fusion protein.

8. The Fc-containing molecule of claim 1, wherein the Fc-containing molecule comprises N-linked glycosylation.

9. The Fc-containing molecule of claim 8, wherein the Fc-containing molecule is glycosylated by expression in a mammalian host cell.

10. The Fc-containing molecule of claim 9, wherein the mammalian host cell is a Chinese hamster ovary (CHO) cell line.

11. A composition comprising the Fc-containing molecule of claim 8, wherein greater than 40% of the Fc-containing molecules comprise mature N-linked glycosylation.

12. The composition of claim 11, wherein greater than 50% of the Fc-containing molecules comprise mature N-linked glycosylation.

13. The composition of claim 12, wherein greater than 70% of the Fc-containing molecules comprise mature N-linked glycosylation.

14. The composition of claim 11, wherein less than 5% of the Fc-containing molecules comprise mannose 5 (M5) N-linked glycosylation.

15. The composition of claim 14, wherein less than 2% of the Fc-containing molecules comprise mannose 5 (M5) N-linked glycosylation.

16. The composition of claim 15, wherein less than 1% of the Fc-containing molecules comprise mannose 5 (M5) N-linked glycosylation.

* * * * *